US009169281B2

(12) United States Patent
Fukuzumi et al.

(10) Patent No.: US 9,169,281 B2
(45) Date of Patent: Oct. 27, 2015

(54) MONONUCLEAR METAL COMPLEX, HYDROGENATION REDUCTION CATALYST, DEHYDROGENATION CATALYST, METHOD FOR PRODUCING HYDROGENATION REDUCTION PRODUCT, METHOD FOR PRODUCING HYDROGEN ($H_2$), AND METHOD FOR PRODUCING DEHYDROGENATION REACTION PRODUCT

(75) Inventors: Shunichi Fukuzumi, Suita (JP); Tomoyoshi Suenobu, Suita (JP); Yuta Maenaka, Suita (JP)

(73) Assignee: OSAKA UNIVERSITY, Osaka (JP)

( * ) Notice: Subject to any disclaimer, the term of this patent is extended or adjusted under 35 U.S.C. 154(b) by 357 days.

(21) Appl. No.: 13/582,653

(22) PCT Filed: Mar. 4, 2011

(86) PCT No.: PCT/JP2011/055148
§ 371 (c)(1),
(2), (4) Date: Sep. 4, 2012

(87) PCT Pub. No.: WO2011/108730
PCT Pub. Date: Sep. 9, 2011

(65) Prior Publication Data
US 2012/0321550 A1 Dec. 20, 2012

(30) Foreign Application Priority Data
Mar. 4, 2010 (JP) .................... 2010-048477

(51) Int. Cl.
C07F 15/00 (2006.01)
B01J 31/02 (2006.01)
B01J 31/22 (2006.01)
C07F 17/02 (2006.01)

(52) U.S. Cl.
CPC ......... *C07F 15/0033* (2013.01); *B01J 31/0252* (2013.01); *B01J 31/2295* (2013.01); *C07F 17/02* (2013.01); *B01J 2531/827* (2013.01); *B01J 2540/12* (2013.01); *B01J 2540/32* (2013.01)

(58) Field of Classification Search
CPC .................................................. C07F 15/0033
See application file for complete search history.

(56) References Cited

U.S. PATENT DOCUMENTS

2010/0034733 A1  2/2010  Fukuzumi et al.

FOREIGN PATENT DOCUMENTS

JP   2009-078200   4/2009
WO  2008/059630   5/2008

OTHER PUBLICATIONS

Ustynyuk et al. CAS Accession No. 1971:449297.*
Himeda et al., "Simultaneous Tuning of Activity and Water Solubility of Complex Catalysts by Acid-Base Equilibrium of Ligands for Conversion of Carbon Dioxide", Organometallics, 2007, vol. 26, No. 3, pp. 702-712.
Fujita et al., "Synthesis of Five-, Six-, and Seven-Membered Ring Lactams by Cp*Rh Complex-Catalyzed Oxidative N-Heterocyclization of Amino Alcohols", Organic Letters, 2004, vol. 6, No. 16, pp. 2785-2788.
Nutton et al., "Pentamethylcyclopentadienyl-rhodium and -iridium Complexes. Part 29. Syntheses and X-Ray Structure Determinations of [ {Rh ($C_5Me_5$)}$_2$(OH)$_3$] OH • 11$H_2$O and [ {Ir ($C_5Me_5$)}$_2$(OH)$_3$]O$_2$CMe • 14$H_2$O and Related Complexes", Journal of the Chemical Society, Dalton Transactions., 1981, vol. 9, pp. 1997-2002.
isen et al., "Aqueous Organometallic Chemistry: Structure and Dynamics in the Formation of ($\eta^5$-Pentamethylcyclopentadienyl)rhodium Aqua Complexes as a Function of pH", Organometallics, 1995, vol. 14, pp. 2806-2812.
Ogo et al., "Crystallographic report: Crystal structures of organometallic aqua complexes [Cp*Rh$^{III}$(bpy) (OH$_2$)]$^{2+}$ and [Cp*Rh$^{III}$(6,6'-Me$_2$bpy)(OH$_2$)]$^{2+}$ used as key catalysts in regioselective reduction of NAD+ analogues", Applied Organometallic Chemistry, 2005, vol. 19, pp. 639-643.

(Continued)

*Primary Examiner* — Joseph Kosack
(74) *Attorney, Agent, or Firm* — Hamre, Schumann, Mueller & Larson, P.C.

(57) ABSTRACT

The present invention provides: a mononuclear metal complex that has high catalytic activity and can be used as a hydrogenation reduction catalyst that allows efficient hydrogenation reduction of a substance to be reduced; a tautomer or stereoisomer thereof; or a salt thereof. Provided is the mononuclear metal complex represented by the following formula (1), a tautomer or stereoisomer thereof; or a salt thereof.

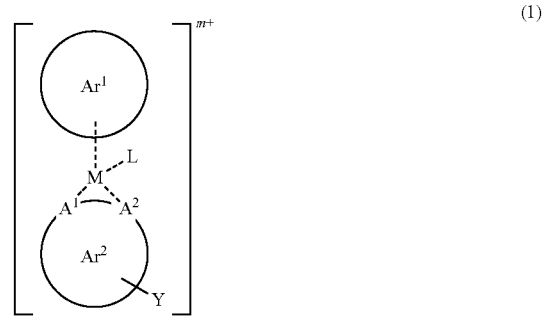

In the formula (1), $Ar^1$ is an aromatic anionic ligand or an aromatic ligand, or is not present, $Ar^2$ is a ligand having aromaticity and may or may not be substituted, and when $Ar^2$ is substituted, the number of substituents may be one or more, M is an atom or ion of a transition metal, $A^1$ and $A^2$ are both carbon atoms, or one of $A^1$ and $A^2$ is a carbon atom and the other is a nitrogen atom, Y is an anionic group or a cationic group, or is not present, L is any ligand or is not present, and m is a positive integer, 0, or a negative integer.

12 Claims, 32 Drawing Sheets

(56) References Cited

OTHER PUBLICATIONS

Lo et al., "Bioorganometallic Chemistry. 13. Regioselective Reduction of NAD+ Models, 1-benzylnicotinamde Triflate and β-Nicotinamide Ribose-5'-methyl Phosphate, with in Situ Generated [Cp*Rh(Bpy)II]+: Structure-Activity Relationships, Kinetics, and Mechanistic Aspects in the Formation of the 1,4-NADH Derivatives", Inorganic Chemistry, 2001, vol. 40, No. 26, pp. 6705-6716.

Grigg et al., "Cyclometallated Ir(III), Rh(III) and Ru(II) complexes as catalysts for the cyclotrimerisation of 1, 6-diynes with monoynes", ARKIVOC, 2007, No. 11, pp. 145-160.

Kashiwame et al., Metal-Pyrazole Bifunction in Half-Sandwich C-N Chelate Iridium Complexes: Pyrazole-Pyrazolato Interconversion and Application to Catalytic Intramolecular Hydroamination of Aminoalkene, Chemistry—A European Journal, 2010, vol. 16, No. 3, pp. 766-770.

Hull et al., "Highly Active and Robust Cp* Iridium Complexes for Catalytic Water Oxidation" Journal of the American Chemical Society, 2009, vol. 131, No. 25, pp. 8730-8731.

Li et al., "C—H Activation of Phenyl Imines and 2-Phenylpyridines with [Cp*MCl$_2$]$_2$ (M=Ir, Rh): Regioselectivity, Kinetics, and Mechanism", Organometallics, 2009, vol. 28, No. 12, pp. 3492-3500.

Fukuzumi et al., "Efficient Catalytic Decomposition of Formic Acid for the Selective Generation of $H_2$ and H/D Exchange with a Water Soluble Rhodium Complex in Aqueous Solution", ChemSusChem, 2008, vol. 1, No. 10, pp. 827-834.

Fukuzumi et al., "Unusually Large Tunneling Effect on Highly Efficient Generation of Hydrogen and Hydrogen Isotopes in pH-Selective Decomposition of Formic Acid Catalyzed by a Heterodinuclear Iridium-Ruthenium Complex in Water", Journal of the American Chemical Society, 2010, vol. 132, No. 5, pp. 1496-1497.

Hayashi et al., "Accelerating Effect of a Proton on the Reduction of $CO_2$ Dissolved in Water under Acidic Conditions. Isolation, Crystal Structure, and Reducing Ability of a Water-Soluble Ruthenium Hydride Complex", Journal of the American Chemical Society, 2003, vol. 125, No. 47, pp. 14266-14267.

Ogo et al., "Mechanistic investigation of $CO_2$ hydrogenation by Ru(II) and Ir(III) aqua complexes under acidic conditions: two catalytic systems differing in the nature of the rate determining step", Dalton Transactions, 2006, pp. 4657-4663.

Himeda, "Highly efficient hydrogen evolution by decomposition of formic acid using an iridium catalyst with 4,4'-dihydroxy-2,2'-bipyridine", Green Chemistry, 2009, vol. 11, No. 12, pp. 2018-2022.

Boddien et al., "Iron-Catalyed Hydrogen Production from Formic Acid", Journal of the American Chemical Society, 2010, vol. 132, No. 26, pp. 8924-8934.

* cited by examiner

MONONUCLEAR METAL COMPLEX, HYDROGENATION REDUCTION CATALYST, DEHYDROGENATION CATALYST, METHOD FOR PRODUCING HYDROGENATION REDUCTION PRODUCT, METHOD FOR PRODUCING HYDROGEN ($H_2$), AND METHOD FOR PRODUCING DEHYDROGENATION REACTION PRODUCT

TECHNICAL FIELD

The present invention relates to a mononuclear metal complex, a hydrogenation reduction catalyst (a catalyst for causing reduction by hydrogenation), a dehydrogenation catalyst, a method for producing a hydrogenation reduction product, a method for producing hydrogen ($H_2$), and a method for producing a dehydrogenation reaction product.

BACKGROUND ART

Hydrogen can be produced from various raw materials such as fossil fuel, biomass, and water. There are growing expectations for hydrogen to be used as an energy source for fuel cell cars and energy for home and business use, for example. Hydrogen is the ultimate clean energy source because only water is left after it is burned. If the use of hydrogen energy as automotive fuel etc. becomes more widespread in the future, it not only can reduce air pollution but also can serve as a fundamental countermeasure against global warming. In order to achieve 80% reduction in carbon dioxide ($CO_2$) emissions by 2050, it is necessary to spread such use of hydrogen energy.

Various studies have been made for hydrogen, and for example, an iridium metal complex is disclosed that causes carbon dioxide to be reduced (hydrogenated) by hydrogen to generate formic acid (see Non-Patent Document 1).

CITATION LIST

Non-Patent Document(s)

[Non-Patent Document 1] Himeda, Y. et al. Organometallics 2007, 26, pp. 702-712

BRIEF SUMMARY OF THE INVENTION

Problem to be Solved by the Invention

However, there are still many technical problems to be solved before the use of hydrogen energy can become widespread. For example, although the metal complex described in Non-Patent Document 1 can cause carbon dioxide to be reduced by hydrogen to generate formic acid in an aqueous solution at ordinary temperature and ordinary pressure, the catalytic activity of the metal complex is low. If efficient formic acid production from hydrogen and carbon dioxide becomes possible, it is expected that it can contribute to the fixation (storage) of both hydrogen and carbon dioxide.

Also, if hydrogenation reduction of not only carbon dioxide but also various substances to be reduced becomes possible, it is expected that it can contribute to the storage of hydrogen. Furthermore, if the generation of hydrogen ($H_2$) by decomposing not only formic acid but also any other substance that can serve as a hydrogen source (e.g., a product obtained through the above-described hydrogenation reduction) becomes possible, it is expected that it can contribute to more efficient utilization of hydrogen energy.

With the foregoing in mind, it is an object of the present invention to provide: a mononuclear metal complex that has high catalytic activity and can be used as a hydrogenation reduction catalyst that allows efficient hydrogenation reduction of a substance to be reduced; a hydrogenation reduction catalyst; a dehydrogenation catalyst; a method for producing a hydrogenation reduction product; a method for producing hydrogen ($H_2$); and a method for producing a dehydrogenation reaction product.

Means for Solving Problem

In order to achieve the above object, the present invention provides a mononuclear metal complex represented by the following formula (1); a tautomer or stereoisomer of the mononuclear metal complex; or a salt of the mononuclear metal complex, the tautomer, or the stereoisomer.

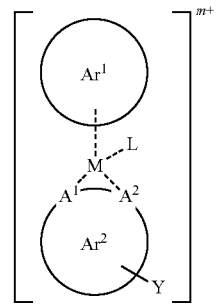

In the formula (1),
$Ar^1$ is an aromatic anionic ligand or an aromatic ligand, or is not present,
$Ar^2$ is a ligand having aromaticity and may or may not be substituted, and when $Ar^2$ is substituted, the number of substituents may be one or more,
M is an atom or ion of a transition metal,
$A^1$ and $A^2$ are both carbon atoms, or one of $A^1$ and $A^2$ is a carbon atom and the other is a nitrogen atom,
Y is an anionic group or a cationic group, or is not present,
L is any ligand or is not present, and
m is a positive integer, 0, or a negative integer.

The present invention also provides a hydrogenation reduction catalyst including the mononuclear metal complex according to the present invention, a tautomer or stereoisomer of the mononuclear metal complex, or a salt of the mononuclear metal complex, the tautomer, or the stereoisomer.

The present invention also provides a dehydrogenation catalyst including the mononuclear metal complex according to the present invention, a tautomer or stereoisomer of the mononuclear metal complex, or a salt of the mononuclear metal complex, the tautomer, or the stereoisomer.

The present invention also provides a method for producing a hydrogenation reduction product by causing hydrogenation reduction of a substance to be reduced. The method includes the step of: in a solution or disperse system that contains the hydrogenation reduction catalyst according to the present invention, the substance to be reduced, and hydrogen ($H_2$), reducing the substance to be reduced by a reaction between the substance to be reduced and the hydrogen ($H_2$).

The present invention also provides a method for producing hydrogen ($H_2$). The method includes the step of: in a solution or disperse system that contains the dehydrogenation catalyst according to the present invention and a hydrogen source, decomposing the hydrogen source to generate hydrogen ($H_2$). The present invention also provides a method for producing a dehydrogenation reaction product. The method includes the step of: in a solution or disperse system that contains the dehydrogenation catalyst according to the present invention and a hydrogen source, decomposing the hydrogen source to generate a dehydrogenation reaction product.

Effects of the Invention

According to the present invention, it is possible to provide a mononuclear metal complex that has high catalytic activity and can be used as a hydrogenation reduction catalyst that allows efficient hydrogenation reduction of a substance to be reduced; a hydrogenation reduction catalyst; a dehydrogenation catalyst; a method for producing a hydrogenation reduction product; a method for producing hydrogen ($H_2$); and a method for producing a dehydrogenation reaction product.

MODE FOR CARRYING OUT THE INVENTION

Figure 1A:
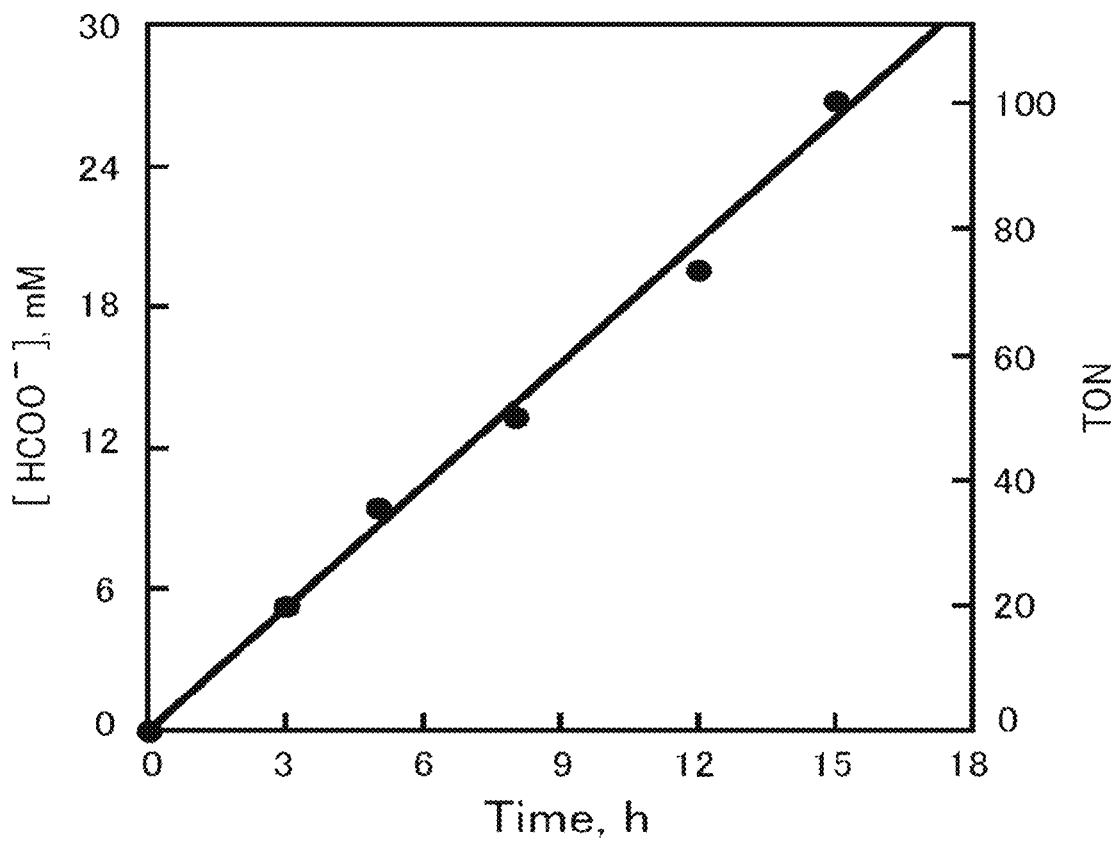
FIG. 1A is a graph showing, in Example 3, the relationship of the passage of reaction time in an aqueous solution of an iridium mononuclear aqua complex of Example 1 with the amount of the generated formic acid and with TON.

Embodiments of the present invention will be described below by way of illustrative example. It is to be noted, however, that the present invention is by no means limited by the following description. In the present invention, when the scope of the invention is limited by numerical values, the present invention encompasses not only the case of the exact range defined by the numerical values but also the case of an approximate range defined by the numerical values. For example, when it is specified that a temperature is in the range from "15° C. to 80° C.", the temperature may be exactly from 15° C. to 80° C., or may be from about 15° C. to about 80° C.

[Mononuclear Metal Complex]

The inventors of the present invention conducted a diligent study in order to solve the above-described problems, and as a result, they found out that the mononuclear metal complex represented by the formula (1) is useful for solving the problems. In the mononuclear metal complex represented by the formula (1), examples of $Ar^1$, which is an aromatic anionic ligand or an aromatic ligand, include a cyclopentadienyl group, a pentamethylcyclopentadienyl group, a hexamethylbenzene group, and a tetramethylcyclopentadienyl group.

In the mononuclear metal complex represented by the formula (1), the ligand $Ar^2$ is not limited as long as it is a ligand having aromaticity. Examples of the ligand having aromaticity include 2-(1-pyrazolyl)phenyl group, 1-phenylpyrazole, 2-phenylpyridine, and benzo[h]quinoline. When the ligand $Ar^2$ has one or more substituents in addition to Y, the one or more substituents preferably are each independently an alkyl group, a phenyl group, a cyclopentadienyl group, a carboxy group, a sulfo group, a hydroxyl group, an alkoxy group, an amino group, a hydroxymethyl group, or a phosphate group.

In the formula (1), M preferably is iridium, ruthenium, rhodium, cobalt, osmium, nickel, iron, manganese, chromium, cobalt, platinum, rhenium, palladium, or platinum. It is particularly preferable that M is iridium.

In the formula (1), as described above, $A^1$ and $A^2$ are both carbon atoms, or one of them is a carbon atom and the other is a nitrogen atom. Specifically, $A^1$ and $A^2$ both may be carbon atoms; $A^1$ may be a carbon atom and $A^2$ may be a nitrogen atom; or $A^2$ may be a carbon atom and $A^1$ may be a nitrogen atom. The inventors of the present invention found out that the complex of the formula (1) where at least one of $A^1$ and $A^2$ is a carbon atom as described above is useful as a carbon dioxide fixation catalyst, thereby achieving the present invention.

In the formula (1), Y preferably is an anionic group or a cationic group. With this configuration, it is possible to further improve the solubility of the complex in solvents such as water. This was found out by the inventors of the present invention on their own. In the formula (1), it is more preferable that Y is a carboxy group, a sulfo group, a phenolic hydroxyl group, a phosphate group, an amino group, or a hydroxymethyl group.

In the formula (1), L preferably is a water molecule, a hydrogen atom, an alkoxide ion, a hydroxide ion, a halide ion, a bicarbonate ion, a carbonate ion, a trifluoromethanesulfonate ion, a sulfate ion, a nitrate ion, a formate ion, an acetate ion, a hydrido ion, a hydroxide ion, a hexafluorophosphate ion, or a tetrafluoroborate ion, or is not present. The alkoxide ion is not particularly limited. Preferably, it is an alkoxide ion derived from a straight-chain or branched-chain alcohol having 1 to 6 carbon atoms. Examples of such an alkoxide ion include those derived from methanol, ethanol, n-propyl alcohol, isopropyl alcohol, n-butyl alcohol, sec-butyl alcohol, isobutyl alcohol, and tert-butyl alcohol.

Depending on the kind of the ligand L in the formula (1), it may be relatively easy to substitute or eliminate the ligand L, for example. For example, the ligand L may turn to: a hydroxide ion in a basic aqueous solution; a water molecule in a neutral, weakly acidic, or strongly acidic aqueous solution; and an alkoxide ion in an alcohol solvent. Also, the ligand L may be eliminated by light or heat. It is to be noted, however, that this description merely is directed to an illustrative example of a presumable mechanism and does not limit the present invention by any means.

In the formula (1), m is determined depending on the electric charge of the atom or ion of the transition metal and the electric charges of the respective ligands present in the formula (1). For example, m preferably is −4 to +4, more preferably −2 to +2.

It is preferable that the mononuclear metal complex represented by the formula (1) is a mononuclear metal complex represented by the following formula (2).

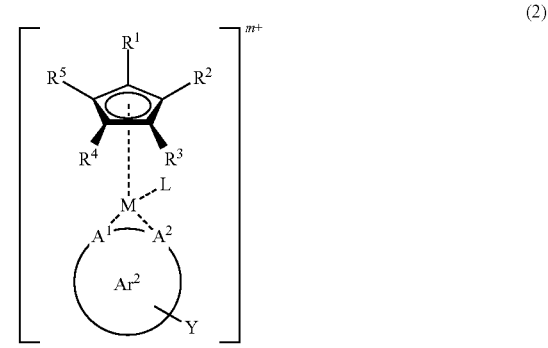

In the formula (2), $R^1$ to $R^5$ are each independently a hydrogen atom or any substituent, and $Ar^2$, M, $A^1$, $A^2$, Y, L, and m are the same as those in the formula (1).

In the formula (2), $R^1$ to $R^5$ preferably are each independently a hydrogen atom, an alkyl group, a phenyl group, a cyclopentadienyl group, an alkoxy group, an amino group, a carboxylic acid group (carboxy group), a hydroxy group, a hydroxymethyl group, or a phosphate group. The alkyl group preferably is a straight-chain or branched alkyl group having 1 to 6 carbon atoms, more preferably a methyl group, an ethyl group, a propyl group, a butyl group, an isopropyl group, or a tertiary butyl group. It is particularly preferable that $R^1$ to $R^5$ are all methyl groups. It is also preferable that, for example, $R^1$ to $R^5$ are all hydrogen atoms.

It is also preferable that the mononuclear metal complex represented by the formula (1) is a mononuclear metal complex represented by the following formula (3).

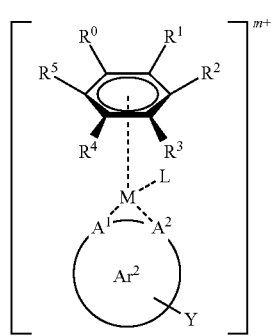
(3)

In the formula (3), $R^0$ to $R^5$ are each independently a hydrogen atom or any substituent, and $Ar^2$, M, $A^1$, $A^2$, Y, L, and m are the same as those in the formula (1).

In the formula (3), $R^0$ to $R^5$ preferably are each independently a hydrogen atom, an alkyl group, a phenyl group, a cyclopentadienyl group, an alkoxy group, an amino group, a carboxylic acid group (carboxy group), a hydroxy group, a hydroxymethyl group, or a phosphate group. The alkyl group preferably is a straight-chain or branched alkyl group having 1 to 6 carbon atoms, more preferably a methyl group, an ethyl group, a propyl group, a butyl group, an isopropyl group, or a tertiary butyl group. It is particularly preferable that $R^0$ to $R^5$ are all methyl groups. It is also preferable that, for example, $R^0$ to $R^5$ are all hydrogen atoms.

In the mononuclear metal complex according to the present invention, a tautomer or stereoisomer thereof, or a salt thereof, it is more preferable that the mononuclear metal complex represented by the formula (2) is a mononuclear metal complex represented by the following formula (4).

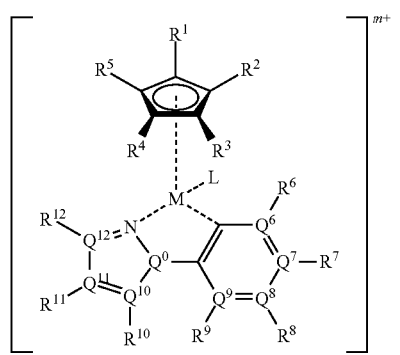
(4)

In the formula (4), $R^6$ to $R^{12}$ are each independently a hydrogen atom or any substituent, or $R^9$ and $R^{10}$ may together form —CH=CH— where the Hs may each independently be substituted with any substituent, $Q^0$ is C or N, $Q^6$ to $Q^{12}$ are each independently C or N$^+$, or at least one pair of $Q^X$ and $R^X$ with the same X (X is any integer from 6 to 12) may together form N, and M, L, m, and $R^1$ to $R^5$ are the same as those in the formula (2).

In the formula (4), it is more preferable that $R^6$ to $R^{12}$ are each independently a hydrogen atom, an alkyl group, a phenyl group, a benzyl group, a nitro group, a halogen group, a sulfonate group (sulfo group), an amino group, a carboxylic acid group (carboxy group), a hydroxyl group, an alkoxy group, an isopropyl group, a tertiary butyl group, a benzyl group, a phosphate group, or a hydroxymethyl group. The alkyl group preferably is a straight-chain or branched alkyl group having 1 to 6 carbon atoms, more preferably a methyl group, an ethyl group, a propyl group, a butyl group, an isopropyl group, or a tertiary butyl group. The alkoxy group preferably is a straight-chain or branched alkoxy group having 1 to 6 carbon atoms, particularly preferably a methoxy group. Alternatively, $R^9$ and $R^{10}$ may together form —CH=CH— where the Hs may each independently be substituted with an alkyl group, a phenyl group, a benzyl group, a nitro group, a halogen group, a sulfonate group (sulfo group), an amino group, a carboxylic acid group (carboxy group), a hydroxyl group, an alkoxy group, a phosphate group, or a hydroxymethyl group. The alkyl group preferably is a straight-chain or branched alkyl group having 1 to 6 carbon atoms, more preferably a methyl group, an ethyl group, a propyl group, a butyl group, an isopropyl group, or a tertiary butyl group. The alkoxy group preferably is a straight-chain or branched alkoxy group having 1 to 6 carbon atoms, particularly preferably a methoxy group.

In the formula (4), it is more preferable that at least one of $R^6$ to $R^{12}$ is an anionic group or a cationic group, and it is particularly preferable that $R^7$ is an anionic group or a cationic group. Also, it is particularly preferable that all $R^6$ to $R^{12}$ except for the one (or those) that is an anionic group or a cationic group are hydrogen atoms. For example, when $R^7$ is an anionic group or a cationic group, it is particularly preferable that $R^6$ and $R^8$ to $R^{12}$ are all hydrogen atoms. The anionic group or cationic group is as described above. It is particularly preferable that $Q^6$ to $Q^{12}$ are all Cs (carbon atoms). Alternatively, $G^0$ and $Q^6$ to $Q^9$ all may be Cs (carbon atoms), and $Q^{10}$ to $Q^{12}$ all may be Ns (nitrogen atoms).

Furthermore, in the mononuclear metal complex according to the present invention, a tautomer or stereoisomer thereof, or a salt thereof, it is more preferable that the mononuclear metal complex represented by the formula (2) is a mononuclear metal complex represented by the following formula (5).

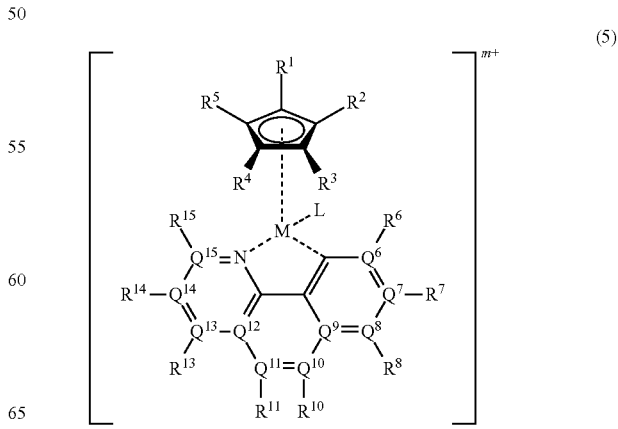
(5)

In the formula (5),

R$^6$ to R$^8$, R$^{10}$ to R$^{11}$, and R$^{13}$ to R$^{15}$ are each independently a hydrogen atom or any substituent, Q$^6$ to Q$^{15}$ are each independently C or N$^+$, or at least one pair of Q$^X$ and R$^X$ with the same X (X is any integer from 6 to 15) may together form N, and M, L, m, and R$^1$ to R$^5$ are the same as those in the formula (2).

In the formula (5), it is more preferable that R$^6$ to R$^8$, R$^{10}$ to R$^{11}$, and R$^{13}$ to R$^{15}$ are each independently a hydrogen atom, an alkyl group, a phenyl group, a benzyl group, a nitro group, a halogen group, a sulfonate group (sulfo group), an amino group, a carboxylic acid group (carboxy group), a hydroxyl group, an alkoxy group, a phosphate group, or a hydroxymethyl group. The alkyl group preferably is a straight-chain or branched alkyl group having 1 to 6 carbon atoms, more preferably a methyl group, an ethyl group, a propyl group, a butyl group, an isopropyl group, or a tertiary butyl group. The alkoxy group preferably is a straight-chain or branched alkoxy group having 1 to 6 carbon atoms, particularly preferably a methoxy group.

In the formula (5), it is more preferable that at least one of R$^6$ to R$^8$, R$^{10}$ to R$^{11}$, and R$^{13}$ to R$^{15}$ is an anionic group or a cationic group, and it is particularly preferable that R$^7$ is an anionic group or a cationic group. Also, it is particularly preferable that all R$^6$ to R$^8$, R$^{10}$ to R$^{11}$, and R$^{13}$ to R$^{15}$ except for the one (or those) that is an anionic group or a cationic group are hydrogen atoms. For example, when R$^7$ is an anionic group or a cationic group, it is particularly preferable that R$^6$, R$^8$, R$^{10}$ to R$^{11}$, and R$^{13}$ to R$^{15}$ are all hydrogen atoms. The anionic group or cationic group is as described above. Also, it is particularly preferable that Q$^6$ to Q$^{15}$ are all Cs (carbon atoms).

Furthermore, in the mononuclear metal complex according to the present invention, a tautomer or stereoisomer thereof, or a salt thereof, it is more preferable that the mononuclear metal complex represented by the formula (2) is a mononuclear metal complex represented by the following formula (6).

In the formula (6), it is more preferable that R$^6$ to R$^{13}$ are each independently a hydrogen atom, an alkyl group, a phenyl group, a benzyl group, a nitro group, a halogen group, a sulfonate group (sulfo group), an amino group, a carboxylic acid group (carboxy group), a hydroxyl group, an alkoxy group, a phosphate group, or a hydroxymethyl group. The alkyl group preferably is a straight-chain or branched alkyl group having 1 to 6 carbon atoms, more preferably a methyl group, an ethyl group, a propyl group, a butyl group, an isopropyl group, or a tertiary butyl group. The alkoxy group preferably is a straight-chain or branched alkoxy group having 1 to 6 carbon atoms, particularly preferably a methoxy group. Alternatively, R$^9$ and R$^{19}$ may together form —CH=CH— where the Hs may each independently be substituted with an alkyl group, a phenyl group, a benzyl group, a nitro group, a halogen group, a sulfonate group (sulfo group), an amino group, a carboxylic acid group (carboxy group), a hydroxyl group, an alkoxy group, or a phosphate group. The alkyl group preferably is a straight-chain or branched alkyl group having 1 to 6 carbon atoms, more preferably a methyl group, an ethyl group, a propyl group, a butyl group, an isopropyl group, or a tertiary butyl group. The alkoxy group preferably is a straight-chain or branched alkoxy group having 1 to 6 carbon atoms, particularly preferably a methoxy group.

In the formula (6), it is more preferable that at least one of R$^6$ to R$^{13}$ is an anionic group or a cationic group, and it is particularly preferable that R$^7$ is an anionic group or a cationic group. Also, it is particularly preferable that all R$^6$ to R$^{13}$ except for the one (or those) that is an anionic group or a cationic group are hydrogen atoms. For example, when R$^7$ is an anionic group or a cationic group, it is particularly preferable that R$^6$ and R$^8$ to R$^{13}$ are all hydrogen atoms. The anionic group or cationic group is as described above. It is particularly preferable that Q$^6$ to Q$^{13}$ are all Cs (carbon atoms).

In the mononuclear metal complex of the present invention, the tautomer or stereoisomer thereof, or the salt thereof, it is more preferable that the mononuclear metal complex represented by the formula (3) is a mononuclear metal complex represented by the following formula (7).

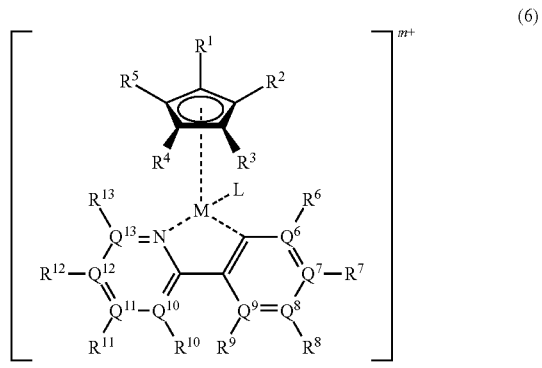

(6)

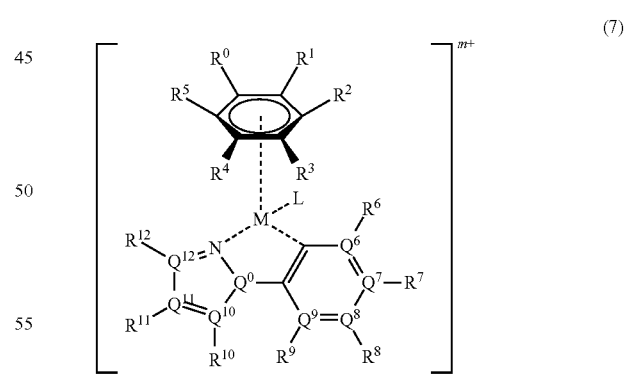

(7)

In the formula (6),

R$^6$ to R$^{13}$ are each independently a hydrogen atom or any substituent, or R$^9$ and R$^{10}$ may together form —CH=CH— where the Hs may each independently be substituted with any substituent, Q$^6$ to Q$^{13}$ are each independently C or N$^+$, or at least one pair of Q$^X$ and R$^X$ with the same X (X is any integer from 6 to 13) may together form N, and M, L, m, and R$^1$ to R$^5$ are the same as those in the formula (2).

In the formula (7),

R$^6$ to R$^{12}$ are each independently a hydrogen atom or any substituent, or R$^9$ and R$^{10}$ may together form —CH=CH— where the Hs may each independently be substituted with any substituent, G$^0$ is C or N, Q$^6$ to Q$^{12}$ are each independently C or N$^+$, or at least one pair of Q$^X$ and R$^X$ with the same X (X is any integer from 6 to 12) may together form N, and M, L, m, and $R^0$ to $R^5$ are the same as those in the formula (3).

In the formula (7), it is more preferable that $R^6$ to $R^{12}$ are each independently a hydrogen atom, an alkyl group, a phenyl group, a benzyl group, a nitro group, a halogen group, a sulfonate group (sulfo group), an amino group, a carboxylic acid group (carboxy group), a hydroxyl group, an alkoxy group, a phosphate group, or a hydroxymethyl group. The alkyl group preferably is a straight-chain or branched alkyl group having 1 to 6 carbon atoms, more preferably a methyl group, an ethyl group, a propyl group, a butyl group, an isopropyl group, or a tertiary butyl group. The alkoxy group preferably is a straight-chain or branched alkoxy group having 1 to 6 carbon atoms, particularly preferably a methoxy group. Alternatively, $R^9$ and $R^{10}$ may together form —CH=CH— where the Hs may each independently be substituted with an alkyl group, a phenyl group, a benzyl group, a nitro group, a halogen group, a sulfonate group (sulfo group), an amino group, a carboxylic acid group (carboxy group), a hydroxyl group, an alkoxy group, a phosphate group, or a hydroxymethyl group. The alkyl group preferably is a straight-chain or branched alkyl group having 1 to 6 carbon atoms, more preferably a methyl group, an ethyl group, a propyl group, a butyl group, an isopropyl group, or a tertiary butyl group. The alkoxy group preferably is a straight-chain or branched alkoxy group having 1 to 6 carbon atoms, particularly preferably a methoxy group.

In the formula (7), it is more preferable that at least one of $R^6$ to $R^{12}$ is an anionic group or a cationic group, and it is particularly preferable that $R^7$ is an anionic group or a cationic group. Also, it is particularly preferable that all $R^6$ to $R^{12}$ except for the one (or those) that is an anionic group or a cationic group are hydrogen atoms. For example, when $R^7$ is an anionic group or a cationic group, it is particularly preferable that $R^6$ and $R^8$ to $R^{12}$ are all hydrogen atoms. The anionic group or cationic group is as described above. It is particularly preferable that $Q^6$ to $Q^{12}$ are all Cs (carbon atoms). Alternatively, $G^0$ and $Q^6$ to $Q^9$ all may be Cs (carbon atoms), and $Q^{10}$ to $Q^{12}$ all may be Ns (nitrogen atoms).

Furthermore, in the mononuclear metal complex according to the present invention, a tautomer or stereoisomer thereof, or a salt thereof, it is more preferable that the mononuclear metal complex represented by the formula (3) is a mononuclear metal complex represented by the following formula (8).

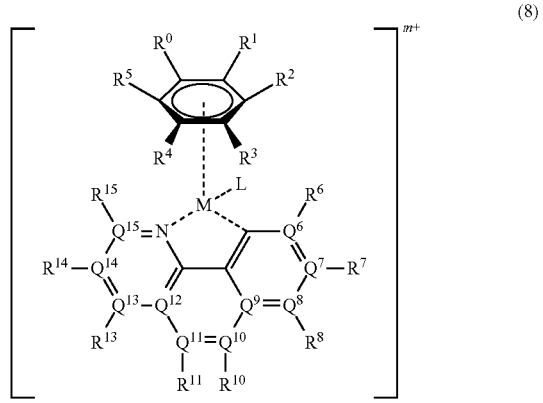

In the formula (8),
$R^6$ to $R^8$, $R^{10}$ to $R^{11}$, and $R^{13}$ to $R^{15}$ are each independently a hydrogen atom or any substituent, $Q^6$ to $Q^{15}$ are each independently C or $N^+$, or at least one pair of $Q^X$ and $R^X$ with the same X (X is any integer from 6 to 15) may together form N, and M, L, m, and $R^0$ to $R^5$ are the same as those in the formula (3).

In the formula (8), it is more preferable that $R^6$ to $R^8$, $R^{10}$ to $R^{11}$, and $R^{13}$ to $R^{15}$ are each independently a hydrogen atom, an alkyl group, a phenyl group, a benzyl group, a nitro group, a halogen group, a sulfonate group (sulfo group), an amino group, a carboxylic acid group (carboxy group), a hydroxyl group, an alkoxy group, a phosphate group, or a hydroxymethyl group. The alkyl group preferably is a straight-chain or branched alkyl group having 1 to 6 carbon atoms, more preferably a methyl group, an ethyl group, a propyl group, a butyl group, an isopropyl group, or a tertiary butyl group. The alkoxy group preferably is a straight-chain or branched alkoxy group having 1 to 6 carbon atoms, particularly preferably a methoxy group.

In the formula (8), it is more preferable that at least one of $R^6$ to $R^8$, $R^{10}$ to $R^{11}$, and $R^{13}$ to $R^{15}$ is an anionic group or a cationic group, and it is particularly preferable that $R^7$ is an anionic group or a cationic group. Also, it is particularly preferable that all $R^6$ to $R^8$, $R^{10}$ to $R^{11}$, and $R^{13}$ to $R^{15}$ except for the one (or those) that is an anionic group or a cationic group are hydrogen atoms. For example, when $R^7$ is an anionic group or a cationic group, it is particularly preferable that $R^6$, $R^8$, $R^{10}$ to $R^{11}$, and $R^{13}$ to $R^{15}$ are all hydrogen atoms. The anionic group or cationic group is as described above. It is particularly preferable that $Q^6$ to $Q^{15}$ are all Cs (carbon atoms).

Furthermore, in the mononuclear metal complex according to the present invention, a tautomer or stereoisomer thereof, or a salt thereof, it is more preferable that the mononuclear metal complex represented by the formula (3) is a mononuclear metal complex represented by the following formula (9).

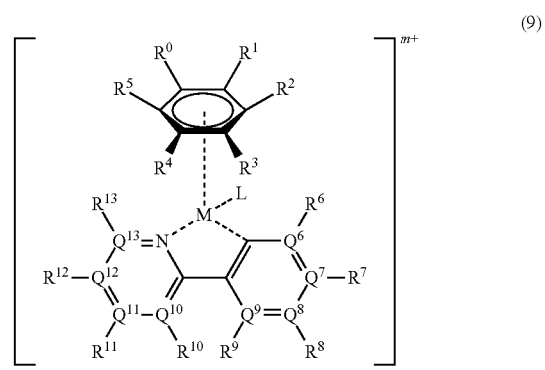

In the formula (9), $R^6$ to $R^{13}$ are each independently a hydrogen atom or any substituent, or $R^9$ and $R^{10}$ may together form —CH=CH— where the Hs may each independently be substituted with any substituent, $Q^6$ to $Q^{13}$ are each independently C or $N^+$, or at least one pair of $Q^X$ and $R^X$ with the same X (X is any integer from 6 to 13) may together form N, and M, L, m, and $R^0$ to $R^5$ are the same as those in the formula (3).

In the formula (9), it is more preferable $R^6$ to $R^{13}$ are each independently a hydrogen atom, an alkyl group, a phenyl group, a benzyl group, a nitro group, a halogen group, a sulfonate group (sulfo group), an amino group, a carboxylic acid group (carboxy group), a hydroxyl group, an alkoxy group, a phosphate group, or a hydroxymethyl group. The alkyl group preferably is a straight-chain or branched alkyl group having 1 to 6 carbon atoms, more preferably a methyl group, an ethyl group, a propyl group, a butyl group, an isopropyl group, or a tertiary butyl group. The alkoxy group preferably is a straight-chain or branched alkoxy group having 1 to 6 carbon atoms, particularly preferably a methoxy group. Alternatively, $R^9$ and $R^{10}$ may together form —CH═CH—, and as described above, the Hs in —CH═CH— may each independently be substituted with an alkyl group, a phenyl group, a benzyl group, a nitro group, a halogen group, a sulfonate group (sulfo group), an amino group, a carboxylic acid group (carboxy group), a hydroxyl group, an alkoxy group, a phosphate group, or a hydroxymethyl group. The alkyl group preferably is a straight-chain or branched alkyl group having 1 to 6 carbon atoms, more preferably a methyl group, an ethyl group, a propyl group, a butyl group, an isopropyl group, or a tertiary butyl group. The alkoxy group preferably is a straight-chain or branched alkoxy group having 1 to 6 carbon atoms, particularly preferably a methoxy group.

In the formula (9), it is more preferable that at least one of $R^6$ to $R^{13}$ is an anionic group or a cationic group, and it is particularly preferable that $R^7$ is an anionic group or a cationic group. It is particularly preferable that all $R^6$ to $R^{13}$ except for the one (or those) that is an anionic group or a cationic group are hydrogen atoms. For example, when $R^7$ is an anionic group or a cationic group, it is particularly preferable that $R^6$ and $R^8$ to $R^{13}$ are all hydrogen atoms. The anionic group or cationic group is as described above. It is particularly preferable that $Q^6$ to $Q^{13}$ are all Cs (carbon atoms).

In the mononuclear metal complex according to the present invention, a tautomer or stereoisomer thereof, or a salt thereof, it is more preferable that the mononuclear metal complex represented by the formula (4) is an iridium mononuclear metal complex represented by the following formula (10).

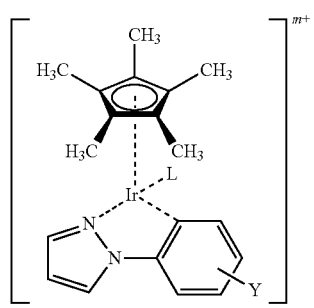

In the formula (10),
Ir is an atom or ion of iridium, and
L, m, and Y are the same as those in the formula (2).
In the formula (10), it is particularly preferable that Y is an anionic group or a cationic group.

In the mononuclear metal complex according to the present invention, a tautomer or stereoisomer thereof, or a salt thereof, it is particularly preferable that the iridium mononuclear metal complex represented by the formula (10) is an iridium mononuclear metal complex represented by the following formula (11).

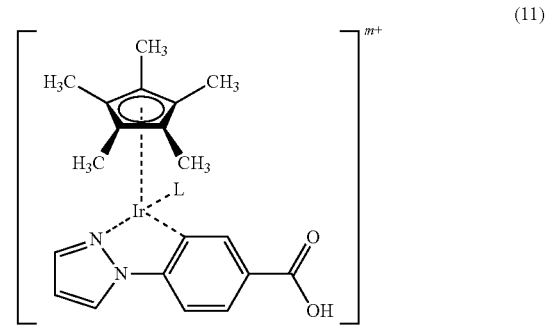

In the formula (11),
L, m, and Ir are the same as those in the formula (10).

In the mononuclear metal complex according to the present invention, a tautomer or stereoisomer thereof, or a salt thereof, it is particularly preferable that the iridium mononuclear metal complex represented by the formula (10) is an iridium mononuclear metal complex represented by the following formula (12).

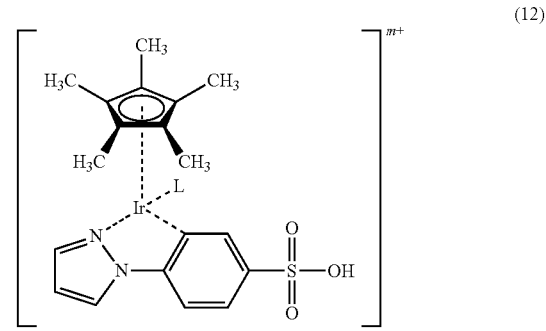

In the formula (12),
L, m, and Ir are the same as those in the formula (10).

In the mononuclear metal complex according to the present invention, a tautomer or stereoisomer thereof, or a salt thereof, it is most preferable that the iridium mononuclear metal complex represented by the formula (11) is an iridium mononuclear metal complex represented by any one of the following formulae (13) to (15), (15A), and (15B). In other words, the ligand L in the iridium mononuclear metal complex represented by the formula (11) preferably is a water molecule (the iridium mononuclear metal complexes (13) and (14)), a hydroxide ion (the iridium mononuclear metal complex (15)), or a hydrido ion (the iridium mononuclear metal complexes (15A) and (15B)). The ligand L in the iridium mononuclear metal complex represented by the formula (11) is not limited thereto. For example, it is also preferable that the ligand L is a methoxide ion, a carbonate ion, a sulfate ion, a nitrate ion, or a formate ion. Also, the ligand L may be any of the above-described ligands, for example.

(13)
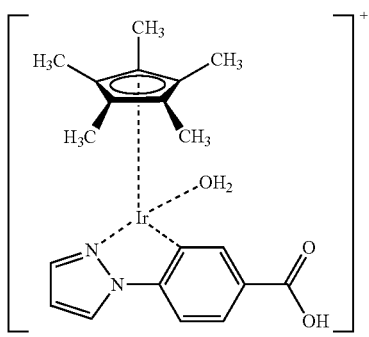

(14)
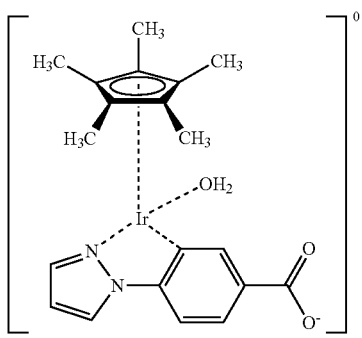

(15)
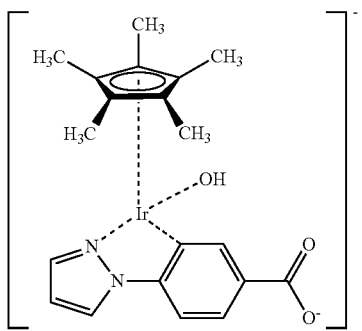

(15A)
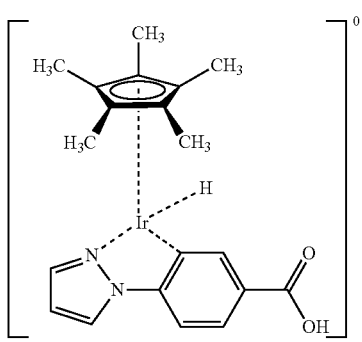

(15B)
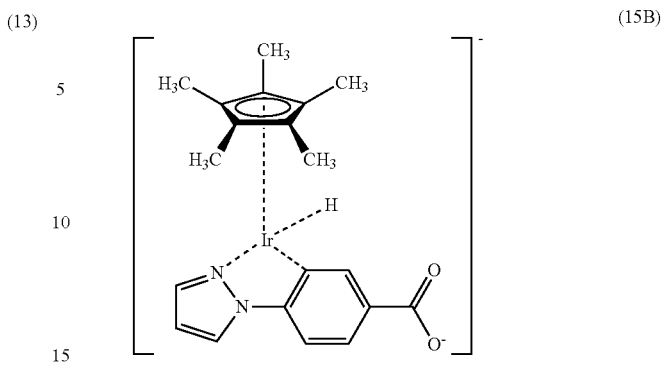

Furthermore, in the mononuclear metal complex according to the present invention, a tautomer or stereoisomer thereof, or a salt thereof, it is most preferable that the iridium mononuclear metal complex represented by the formula (12) is an iridium mononuclear metal complex represented by any of the following formulae (16) to (18), (18A), and (18B). In other words, the ligand L in the iridium mononuclear metal complex represented by the formula (12) preferably is a water molecule (the iridium mononuclear metal complexes (16) and (17)), a hydroxide ion (the iridium mononuclear metal complex (18)), or a hydrido ion (the iridium mononuclear metal complexes (18A) and (18B)). The ligand L in the iridium mononuclear metal complex represented by the formula (12) is not limited thereto. For example, it is also preferable that the ligand L is a methoxide ion, a carbonate ion, a sulfate ion, a nitrate ion, or a formate ion. Also, the ligand L may be any of the above-described ligands, for example.

(16)
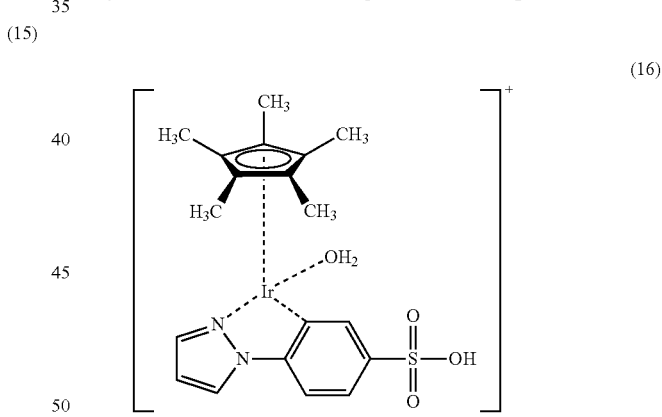

(17)
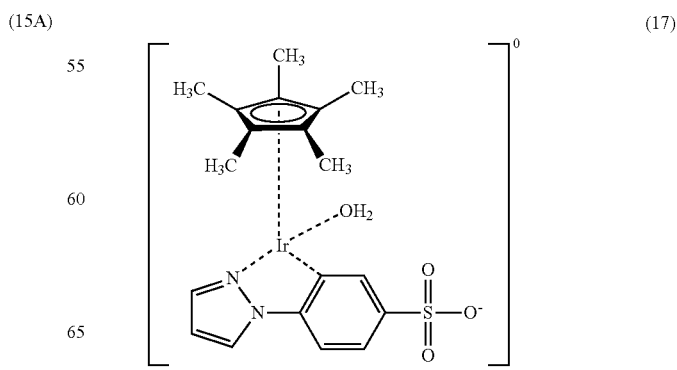

-continued

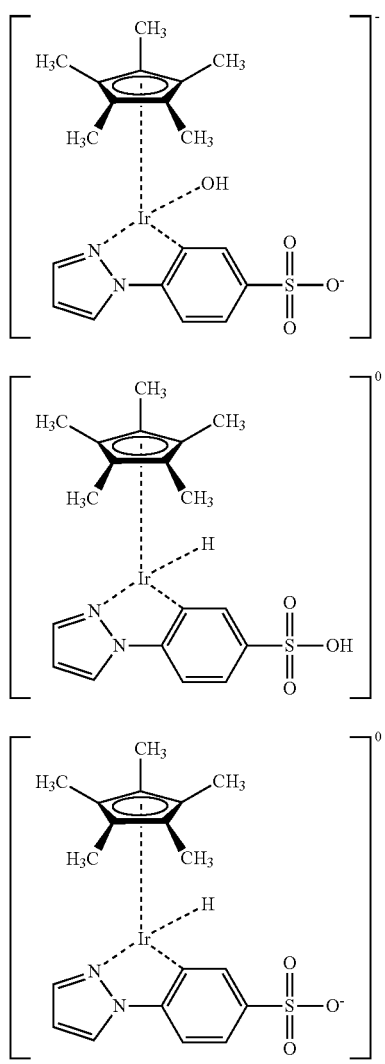

Examples of preferable mononuclear metal complexes represented by the formula (1) include, in addition to the formulae (11) and (12): mononuclear metal complexes shows as Compound Nos. (401) to (457), (501) to (516), (601) to (616), (701) to (758), (801) to (816), and (901) to (916) in the following tables. The structure of each of these mononuclear metal complexes is shown by the combination of M, $Q^X$, and $R^X$ in the formulae (4) to (9) (X is an integer assigned to Q or X in the formulae (4) to (9)). Among these compounds, regarding those that can be represented by the formula (2), $R^1$ to $R^5$ also are shown, and regarding those that can be represented by the formula (4), $R^6$ to $R^{12}$ also are shown. The ligand L in these mononuclear metal complexes is not particularly limited, similarly to the ligand L in the formulae (4) to (9). Preferably, the ligand L is, for example, a water molecule, a hydrogen atom, a hydrido ion, a methoxide ion, or a hydroxide ion, or is not present. m is determined depending on the valence of M and the valence of each ligand, and preferably is 0 to 5, for example. The compounds shown in the following tables all can be produced easily by those skilled in the art without undue experimentation, based on the descriptions in the present specification and common general technical knowledge in the technical field to which the present invention pertains.

TABLE 1

(Examples of the complex represented by the formula (4) ($Q^0$ in each compound is a nitrogen atom or a carbon atom))

| Compound No. | M | $Q^6$ to $Q^{12}$ | $R^1$ to $R^5$ | $R^6$ to $R^{12}$ |
|---|---|---|---|---|
| (401) | iridium | all Cs | all methyl groups | $R^7$ is a phenolic hydroxyl group, and $R^6$ and $R^8$ to $R^{12}$a are all hydrogen atoms |
| (402) | iridium | all Cs | $R^1$ is a hydrogen atom, and $R^2$ to $R^5$ are methyl groups | $R^7$ is a phenolic hydroxyl group, and $R^6$ and $R^8$ to $R^{12}$ are all hydrogen atoms |
| (403) | iridium | all Cs | all hydrogen atoms | $R^7$ is a phenolic hydroxyl group, and $R^6$ and $R^8$ to $R^{12}$ are all hydrogen atoms |
| (404) | iridium | all Cs | all methyl groups | $R^7$ is a phenolic hydroxyl group, $R^{10}$ and $R^{12}$ are methyl groups, and $R^5$ to $R^6$, $R^8$ to $R^9$, and $R^{11}$ are all hydrogen atoms |
| (405) | iridium | all Cs | $R^1$ is a hydrogen atom, and $R^2$ to $R^5$ are methyl groups | $R^7$ is a phenolic hydroxyl group, $R^{10}$ and $R^{12}$ are methyl groups, and $R^5$ to $R^6$, $R^8$ to $R^9$, and $R^{11}$ are all hydrogen atoms |

TABLE 2

(Examples of the complex represented by the formula (4) ($Q^0$ in each compound is a nitrogen atom or a carbon atom))

| Compound No. | M | $Q^6$ to $Q^{12}$ | $R^1$ to $R^5$ | $R^6$ to $R^{12}$ |
|---|---|---|---|---|
| (406) | iridium | all Cs | all hydrogen atoms | $R^7$ is a phenolic hydroxyl group, $R^{10}$ and $R^{12}$ are methyl groups, and $R^5$ to $R^6$, $R^8$ to $R^9$, and $R^{11}$ are all hydrogen atoms |
| (407) | iridium | all Cs | all methyl groups | $R^7$ is a phenolic hydroxyl group, $R^{10}$ is a methyl group, and $R^5$ to $R^6$, $R^8$ to $R^9$, and $R^{11}$ to $R^{12}$ are all hydrogen atoms |
| (408) | iridium | all Cs | $R^1$ is a hydrogen atom, and $R^2$ to $R^5$ are methyl groups | $R^7$ is a phenolic hydroxyl group, $R^{10}$ is a methyl group, and $R^5$ to $R^6$, $R^8$ to $R^9$, and $R^{11}$ to $R^{12}$ are all hydrogen atoms |
| (409) | iridium | all Cs | all hydrogen atoms | $R^7$ is a phenolic hydroxyl group, $R^{10}$ is a methyl group, and $R^5$ to $R^6$, $R^8$ to $R^9$, and $R^{11}$ to $R^{12}$ are all hydrogen atoms |

TABLE 3

(Examples of the complex represented by the formula (4) ($Q^0$ in each compound is a nitrogen atom or a carbon atom))

| Compound No. | M | $Q^6$ to $Q^{12}$ | $R^1$ to $R^5$ | $R^6$ to $R^{12}$ |
|---|---|---|---|---|
| (410) | rhodium | all Cs | all methyl groups | $R^7$ is a phenolic hydroxyl group, and $R^6$ and $R^8$ to $R^{12}$ are all hydrogen atoms |
| (411) | rhodium | all Cs | $R^1$ is a hydrogen atom, and $R^2$ to $R^5$ are methyl groups | $R^7$ is a phenolic hydroxyl group, and $R^6$ and $R^8$ to $R^{12}$ are all hydrogen atoms |
| (412) | rhodium | all Cs | all hydrogen atoms | $R^7$ is a phenolic hydroxyl group, and $R^6$ and $R^8$ to $R^{12}$ are all hydrogen atoms |
| (413) | rhodium | all Cs | all methyl groups | $R^7$ is a phenolic hydroxyl group, $R^{10}$ and $R^{12}$ are methyl groups, and $R^5$ to $R^6$, $R^8$ to $R^9$, and $R^{11}$ are all hydrogen atoms |
| (414) | rhodium | all Cs | $R^1$ is a hydrogen atom, and $R^2$ to $R^5$ are methyl groups | $R^7$ is a phenolic hydroxyl group, $R^{10}$ and $R^{12}$ are methyl groups, $R^5$ to $R^6$, $R^8$ to $R^9$, and $R^{11}$ are all hydrogen atoms |

TABLE 4

(Examples of the complex represented by the formula (4) ($Q^0$ in each compound is a nitrogen atom or a carbon atom))

| Compound No. | M | $Q^6$ to $Q^{12}$ | $R^1$ to $R^5$ | $R^6$ to $R^{12}$ |
|---|---|---|---|---|
| (415) | rhodium | all Cs | all hydrogen atoms | $R^7$ is a phenolic hydroxyl group, $R^{10}$ and $R^{12}$ are methyl groups, and $R^5$ to $R^6$, $R^8$ to $R^9$, and $R^{11}$ are all hydrogen atoms |
| (416) | rhodium | all Cs | all methyl groups | $R^7$ is a phenolic hydroxyl group, $R^{10}$ is a methyl group, and $R^5$ to $R^6$, $R^8$ to $R^9$, and $R^{11}$ to $R^{12}$ are all hydrogen atoms |
| (417) | rhodium | all Cs | $R^1$ is a hydrogen atom, and $R^2$ to $R^5$ are methyl groups | $R^7$ is a phenolic hydroxyl group, $R^{10}$ is a methyl group, and $R^5$ to $R^6$, $R^8$ to $R^9$, and $R^{11}$ to $R^{12}$ are all hydrogen atoms |
| (418) | rhodium | all Cs | all hydrogen atoms | $R^7$ is a phenolic hydroxyl group, $R^{10}$ is a methyl group, and $R^5$ to $R^6$, $R^8$ to $R^9$, and $R^{11}$ to $R^{12}$ are all hydrogen atoms |

TABLE 5

(Examples of the complex represented by the formula (4) ($Q^0$ in each compound is a nitrogen atom or a carbon atom))

| Compound No. | M | $Q^6$ to $Q^{12}$ | $R^1$ to $R^5$ | $R^6$ to $R^{12}$ |
|---|---|---|---|---|
| (419) | rhodium | all Cs | all methyl groups | $R^7$ is a phenolic hydroxyl group, and $R^6$ and $R^8$ to $R^{12}$ are all hydrogen atoms |
| (420) | cobalt | all Cs | all methyl groups | $R^7$ is a phenolic hydroxyl group, and $R^6$ and $R^8$ to $R^{12}$ are all hydrogen atoms |
| (421) | cobalt | all Cs | $R^1$ is a hydrogen atom, and $R^2$ to $R^5$ are methyl groups | $R^7$ is a phenolic hydroxyl group, and $R^6$ and $R^8$ to $R^{12}$ are all hydrogen atoms |
| (422) | cobalt | all Cs | all hydrogen atoms | $R^7$ is a phenolic hydroxyl group, and $R^6$ and $R^8$ to $R^{12}$ are all hydrogen atoms |
| (423) | cobalt | all Cs | all methyl groups | $R^7$ is a phenolic hydroxyl group, $R^{10}$ and $R^{12}$ are methyl groups, and $R^5$ to $R^6$, $R^8$ to $R^9$, and $R^{11}$ are all hydrogen atoms |

TABLE 6

(Examples of the complex represented by the formula (4) ($Q^0$ in each compound is a nitrogen atom or a carbon atom))

| Compound No. | M | $Q^6$ to $Q^{12}$ | $R^1$ to $R^5$ | $R^6$ to $R^{12}$ |
|---|---|---|---|---|
| (424) | cobalt | all Cs | $R^1$ is a hydrogen atom, and $R^2$ to $R^5$ are methyl groups | $R^7$ is a phenolic hydroxyl group, $R^{10}$ and $R^{12}$ are methyl groups, and $R^5$ to $R^6$, $R^8$ to $R^9$, and $R^{11}$ are all hydrogen atoms |
| (425) | cobalt | all Cs | all hydrogen atoms | $R^7$ is a phenolic hydroxyl group, $R^{10}$ and $R^{12}$ are methyl groups, and $R^5$ to $R^6$, $R^8$ to $R^9$, and $R^{11}$ are all hydrogen atoms |
| (426) | cobalt | all Cs | all methyl groups | $R^7$ is a phenolic hydroxyl group, $R^{10}$ is a methyl group, and $R^5$ to $R^6$, $R^8$ to $R^9$, and $R^{11}$ to $R^{12}$ are all hydrogen atoms |
| (427) | cobalt | all Cs | $R^1$ is a hydrogen atom, $R^2$ to $R^5$ are methyl groups | $R^7$ is a phenolic hydroxyl group, $R^{10}$ is a methyl group, $R^5$ to $R^6$, $R^8$ to $R^9$, and $R^{11}$ to $R^{12}$ are all hydrogen atoms |

TABLE 7

(Examples of the complex represented by the formula (4) ($Q^0$ in each compound is a nitrogen atom or a carbon atom))

| Compound No. | M | $Q^6$ to $Q^{12}$ | atom or atomic group | |
|---|---|---|---|---|
| | | | $R^1$ to $R^5$ | $R^6$ to $R^{12}$ |
| (428) | cobalt | all Cs | all hydrogen atoms | $R^7$ is a phenolic hydroxyl group, $R^{10}$ is a methyl group, and $R^5$ to $R^6$, $R^8$ to $R^9$, and $R^{11}$ to $R^{12}$ are all hydrogen atoms |
| (429) | iridium | all Cs | all methyl groups | $R^7$ is a sulfo group (sulfonate group), and $R^6$ and $R^8$ to $R^{12}$ are all hydrogen atoms |
| (430) | iridium | all Cs | $R^1$ is a hydrogen atom, and $R^2$ to $R^5$ are methyl groups | $R^7$ is a sulfo group (sulfonate group), and $R^6$ and $R^8$ to $R^{12}$ are all hydrogen atoms |
| (431) | iridium | all Cs | all hydrogen atoms | $R^7$ is a sulfo group (sulfonate group), and $R^6$ and $R^8$ to $R^{12}$ are all hydrogen atoms |
| (432) | iridium | all Cs | all methyl groups | $R^7$ is a sulfo group (sulfonate group), $R^{10}$ and $R^{12}$ are methyl groups, and $R^5$ to $R^6$, $R^8$ to $R^9$, and $R^{11}$ are all hydrogen atoms |

TABLE 8

(Examples of the complex represented by the formula (4) ($Q^0$ in each compound is a nitrogen atom or a carbon atom))

| Compound No. | M | $Q^6$ to $Q^{12}$ | atom or atomic group | |
|---|---|---|---|---|
| | | | $R^1$ to $R^5$ | $R^6$ to $R^{12}$ |
| (433) | iridium | all Cs | $R^1$ is a hydrogen atom, and $R^2$ to $R^5$ are methyl groups | $R^7$ is a sulfo group (sulfonate group), $R^{10}$ and $R^{12}$ are methyl groups, and $R^5$ to $R^6$, $R^8$ to $R^9$, and $R^{11}$ are all hydrogen atoms |
| (434) | iridium | all Cs | all hydrogen atoms | $R^7$ is a sulfo group (sulfonate group), $R^{10}$ and $R^{12}$ are methyl groups, and $R^5$ to $R^6$, $R^8$ to $R^9$, and $R^{11}$ are all hydrogen atoms |
| (435) | iridium | all Cs | all methyl groups | $R^7$ is a sulfo group (sulfonate group), $R^{10}$ is a methyl group, and $R^5$ to $R^6$, $R^8$ to $R^9$, and $R^{11}$ to $R^{12}$ are all hydrogen atoms |
| (436) | iridium | all Cs | $R^1$ is a hydrogen atom, $R^2$ to $R^5$ are methyl groups | $R^7$ is a sulfo group (sulfonate group), $R^{10}$ is a methyl group, and $R^5$ to $R^6$, $R^8$ to $R^9$, and $R^{11}$ to $R^{12}$ are all hydrogen atoms |

TABLE 9

(Examples of the complex represented by the formula (4) ($Q^0$ in each compound is a nitrogen atom or a carbon atom))

| Compound No. | M | $Q^6$ to $Q^{12}$ | atom or atomic group | |
|---|---|---|---|---|
| | | | $R^1$ to $R^5$ | $R^6$ to $R^{12}$ |
| (437) | iridium | all Cs | all hydrogen atoms | $R^7$ is a sulfo group (sulfonate group), $R^{10}$ is a methyl group, and $R^5$ to $R^6$, $R^8$ to $R^9$, and $R^{11}$ to $R^{12}$ are all hydrogen atoms |
| (438) | rhodium | all Cs | all methyl groups | $R^7$ is a sulfo group (sulfonate group), and $R^6$ and $R^8$ to $R^{12}$ are all hydrogen atoms |
| (439) | rhodium | all Cs | $R^1$ is a hydrogen atom, and $R^2$ to $R^5$ are methyl groups | $R^7$ is a sulfo group (sulfonate group), and $R^6$ and $R^8$ to $R^{12}$ are all hydrogen atoms |
| (440) | rhodium | all Cs | all hydrogen atoms | $R^7$ is a sulfo group (sulfonate group), and $R^6$ and $R^8$ to $R^{12}$ are all hydrogen atoms |
| (441) | rhodium | all Cs | all methyl groups | $R^7$ is a sulfo group (sulfonate group), $R^{10}$ and $R^{12}$ are methyl groups, and $R^5$ to $R^6$, $R^8$ to $R^9$, and $R^{11}$ are all hydrogen atoms |

TABLE 10

(Examples of the complex represented by the formula (4) ($Q^0$ in each compound is a nitrogen atom or a carbon atom))

| Compound No. | M | $Q^6$ to $Q^{12}$ | atom or atomic group | |
|---|---|---|---|---|
| | | | $R^1$ to $R^5$ | $R^6$ to $R^{12}$ |
| (442) | rhodium | all Cs | $R^1$ is a hydrogen atom, and $R^2$ to $R^5$ are methyl groups | $R^7$ is a sulfo group (sulfonate group), $R^{10}$ and $R^{12}$ are methyl groups, and $R^5$ to $R^6$, $R^8$ to $R^9$, and $R^{11}$ are all hydrogen atoms |
| (443) | rhodium | all Cs | all hydrogen atoms | $R^7$ is a sulfo group (sulfonate group), $R^{10}$ and $R^{12}$ are methyl groups, and $R^5$ to $R^6$, $R^8$ to $R^9$, and $R^{11}$ are all hydrogen atoms |
| (444) | rhodium | all Cs | all methyl groups | $R^7$ is a sulfo group (sulfonate group), $R^{10}$ is a methyl group, and $R^5$ to $R^6$, $R^8$ to $R^9$, and $R^{11}$ to $R^{12}$ are all hydrogen atoms |
| (445) | rhodium | all Cs | $R^1$ is a hydrogen atom, $R^2$ to $R^5$ are methyl groups | $R^7$ is a sulfo group (sulfonate group), $R^{10}$ is a methyl group, and $R^5$ to $R^6$, $R^8$ to $R^9$, and $R^{11}$ to $R^{12}$ are all hydrogen atoms |

TABLE 11

(Examples of the complex represented by the formula (4) ($Q^0$ in each compound is a nitrogen atom or a carbon atom))

| Compound No. | M | $Q^6$ to $Q^{12}$ | $R^1$ to $R^5$ | $R^6$ to $R^{12}$ |
|---|---|---|---|---|
| (446) | rhodium | all Cs | all hydrogen atoms | $R^7$ is a sulfo group (sulfonate group), $R^{10}$ is a methyl group, and $R^5$ to $R^6$, $R^8$ to $R^9$, and $R^{11}$ to $R^{12}$ are all hydrogen atoms |
| (447) | rhodium | all Cs | all methyl groups | $R^7$ is a sulfo group (sulfonate group), and $R^6$ and $R^8$ to $R^{12}$ are all hydrogen atoms |
| (448) | cobalt | all Cs | all methyl groups | $R^7$ is a sulfo group (sulfonate group), and $R^6$ and $R^8$ to $R^{12}$ are all hydrogen atoms |
| (449) | cobalt | all Cs | $R^1$ is a hydrogen atom, and $R^2$ to $R^5$ are methyl groups | $R^7$ is a sulfo group (sulfonate group), and $R^6$ and $R^8$ to $R^{12}$ are all hydrogen atoms |
| (450) | cobalt | all Cs | all hydrogen atoms | $R^7$ is a sulfo group (sulfonate group), and $R^6$ and $R^8$ to $R^{12}$ are all hydrogen atoms |

TABLE 12

(Examples of the complex represented by the formula (4) ($Q^0$ in each compound is a nitrogen atom or a carbon atom))

| Compound No. | M | $Q^6$ to $Q^{12}$ | $R^1$ to $R^5$ | $R^6$ to $R^{12}$ |
|---|---|---|---|---|
| (451) | cobalt | all Cs | all methyl groups | $R^7$ is a sulfo group (sulfonate group), $R^{10}$ and $R^{12}$ are methyl groups, and $R^5$ to $R^6$, $R^8$ to $R^9$, and $R^{11}$ are all hydrogen atoms |
| (452) | cobalt | all Cs | $R^1$ is a hydrogen atom, and $R^2$ to $R^5$ are methyl groups | $R^7$ is a sulfo group (sulfonate group), $R^{10}$ and $R^{12}$ are methyl groups, and $R^5$ to $R^6$, $R^8$ to $R^9$, and $R^{11}$ are all hydrogen atoms |
| (453) | cobalt | all Cs | all hydrogen atoms | $R^7$ is a sulfo group (sulfonate group), $R^{10}$ and $R^{12}$ are methyl groups, and $R^5$ to $R^6$, $R^8$ to $R^9$, and $R^{11}$ are all hydrogen atoms |

TABLE 13

(Examples of the complex represented by the formula (4) ($Q^0$ in each compound is a nitrogen atom or a carbon atom))

| Compound No. | M | $Q^6$ to $Q^{12}$ | $R^1$ to $R^5$ | $R^6$ to $R^{12}$ |
|---|---|---|---|---|
| (454) | cobalt | all Cs | all methyl groups | $R^7$ is a sulfo group (sulfonate group), $R^{10}$ is a methyl group, and $R^5$ to $R^6$, $R^8$ to $R^9$, and $R^{11}$ to $R^{12}$ are all hydrogen atoms |
| (455) | cobalt | all Cs | $R^1$ is a hydrogen atom, and $R^2$ to $R^5$ are methyl groups | $R^7$ is a sulfo group (sulfonate group), $R^{10}$ is a methyl group, and $R^5$ to $R^6$, $R^8$ to $R^9$, and $R^{11}$ to $R^{12}$ are all hydrogen atoms |
| (456) | cobalt | all Cs | all hydrogen atoms | $R^7$ is a sulfo group (sulfonate group), $R^{10}$ is a methyl group, and $R^5$ to $R^6$, $R^8$ to $R^9$, and $R^{11}$ to $R^{12}$ are all hydrogen atoms |
| (457) | cobalt | all Cs | all methyl groups | $R^7$ is a sulfo group (sulfonate group), and $R^6$ and $R^8$ to $R^{12}$ are all hydrogen atoms |

TABLE 14

(Examples of the complex represented by the formula (5))

| Compound No. | M | $Q^6$ to $Q^{15}$ | $R^1$ to $R^5$ | $R^6$ to $R^{15}$ |
|---|---|---|---|---|
| (501) | iridium | all Cs | all methyl groups | $R^7$ is a phenolic hydroxyl group, And $R^6$ and $R^8$ to $R^{15}$ are all hydrogen atoms |
| (502) | iridium | all Cs | all methyl groups | $R^7$ is a sulfo group (sulfonate group), and $R^6$ and $R^8$ to $R^{15}$ are all hydrogen atoms |
| (503) | iridium | all Cs | all methyl groups | $R^7$ is a hydroxymethyl group, and $R^6$ and $R^8$ to $R^{15}$ are all hydrogen atoms |
| (504) | iridium | all Cs | all methyl groups | $R^7$ is a phosphate group, and $R^6$ and $R^8$ to $R^{15}$ are all hydrogen atoms |
| (505) | iridium | all Cs | all methyl groups | $R^8$ and $R^{13}$ are phenolic hydroxyl groups, and $R^6$ to $R^7$, $R^{10}$ to $R^{11}$, and $R^{14}$ to $R^{15}$ are hydrogen atoms |
| (506) | iridium | all Cs | $R^1$ is a hydrogen atom, and $R^2$ to $R^5$ are methyl groups | $R^8$ and $R^{13}$ are phenolic hydroxyl groups, and $R^6$ to $R^7$, $R^{10}$ to $R^{11}$, and $R^{14}$ to $R^{15}$ are hydrogen atoms |

TABLE 15

(Examples of the complex represented by the formula (5))

| Compound No. | M | $Q^6$ to $Q^{15}$ | $R^1$ to $R^5$ | $R^6$ to $R^{15}$ |
|---|---|---|---|---|
| (507) | rhodium | all Cs | all methyl groups | $R^8$ and $R^{13}$ are phenolic hydroxyl groups, and $R^6$ to $R^7$, $R^{10}$ to $R^{11}$, and $R^{14}$ to $R^{15}$ are hydrogen atoms |
| (508) | rhodium | all Cs | $R^1$ is a hydrogen atom, and $R^2$ to $R^5$ are methyl groups | $R^8$ and $R^{13}$ are phenolic hydroxyl groups, and $R^6$ to $R^7$, $R^{10}$ to $R^{11}$, and $R^{14}$ to $R^{15}$ are hydrogen atoms |
| (509) | cobalt | all Cs | all methyl groups | $R^8$ and $R^{13}$ are phenolic hydroxyl groups, and $R^6$ to $R^7$, $R^{10}$ to $R^{11}$, and $R^{14}$ to $R^{15}$ are hydrogen atoms |
| (510) | cobalt | all Cs | $R^1$ is a hydrogen atom, and $R^2$ to $R^5$ are methyl groups | $R^8$ and $R^{13}$ are phenolic hydroxyl groups, and $R^6$ to $R^7$, $R^{10}$ to $R^{11}$, and $R^{14}$ to $R^{15}$ are hydrogen atoms |
| (511) | iridium | all Cs | all methyl groups | $R^{10}$ and $R^{11}$ are phenolic hydroxyl groups, and $R^6$ to $R^8$ and $R^{13}$ to $R^{15}$ are hydrogen atoms |

TABLE 16

(Examples of the complex represented by the formula (5))

| Compound No. | M | $Q^6$ to $Q^{15}$ | $R^1$ to $R^5$ | $R^6$ to $R^{15}$ |
|---|---|---|---|---|
| (512) | iridium | all Cs | $R^1$ is a hydrogen atom, and $R^2$ to $R^5$ are methyl groups | $R^{10}$ and $R^{11}$ are phenolic hydroxyl groups, and $R^6$ to $R^8$ and $R^{13}$ to $R^{15}$ are hydrogen atoms |
| (513) | rhodium | all Cs | all methyl groups | $R^{10}$ and $R^{11}$ are phenolic hydroxyl groups and $R^6$ to $R^8$ and $R^{13}$ to $R^{15}$ are hydrogen atoms |
| (514) | rhodium | all Cs | $R^1$ is a hydrogen atom, and $R^2$ to $R^5$ are methyl groups | $R^{10}$ and $R^{11}$ are phenolic hydroxyl groups, and $R^6$ to $R^8$ and $R^{13}$ to $R^{15}$ are hydrogen atoms |
| (515) | cobalt | all Cs | all methyl groups | $R^{10}$ and $R^{11}$ are phenolic hydroxyl groups, and $R^6$ to $R^8$ and $R^{13}$ to $R^{15}$ are hydrogen atoms |
| (516) | cobalt | all Cs | $R^1$ is a hydrogen atom, and $R^2$ to $R^5$ are methyl groups | $R^{10}$ and $R^{11}$ are phenolic hydroxyl groups, and $R^6$ to $R^8$ and $R^{13}$ to $R^{15}$ are hydrogen atoms |

TABLE 17

(Examples of the complex represented by the formula (6))

| Compound No. | M | $Q^6$ to $Q^{13}$ | $R^1$ to $R^5$ | $R^6$ to $R^{13}$ |
|---|---|---|---|---|
| (601) | iridium | all Cs | all methyl groups | $R^7$ is a phenolic hydroxyl group, and $R^6$ and $R^8$ to $R^{13}$ are all hydrogen atoms |
| (602) | iridium | all Cs | all methyl groups | $R^7$ is a sulfo group (sulfonate group), and $R^6$ and $R^8$ to $R^{13}$ are all hydrogen atoms |
| (603) | iridium | all Cs | all methyl groups | $R^7$ is a hydroxymethyl group, and $R^6$ and $R^8$ to $R^{13}$ are all hydrogen atoms |
| (604) | iridium | all Cs | all methyl groups | $R^7$ is a phosphate group, and $R^6$ and $R^8$ to $R^{15}$ are all hydrogen atoms |
| (605) | iridium | all Cs | all methyl groups | $R^8$ and $R^{11}$ are phenolic hydroxyl groups, and $R^6$ to $R^7$, $R^9$ to $R^{10}$, $R^{12}$ to $R^{13}$ are hydrogen atoms |
| (606) | iridium | all Cs | $R^1$ is a hydrogen atom, and $R^2$ to $R^5$ are methyl groups | $R^8$ and $R^{11}$ are phenolic hydroxyl groups, and $R^6$ to $R^7$, $R^9$ to $R^{10}$, $R^{12}$ to $R^{13}$ are hydrogen atoms |

TABLE 18

(Examples of the complex represented by the formula (6))

| Compound No. | M | $Q^6$ to $Q^{13}$ | $R^1$ to $R^5$ | $R^6$ to $R^{13}$ |
|---|---|---|---|---|
| (607) | rhodium | all Cs | all methyl groups | $R^8$ and $R^{11}$ are phenolic hydroxyl groups, and $R^6$ to $R^7$, $R^9$ to $R^{10}$, and $R^{12}$ to $R^{13}$ are hydrogen atoms |
| (608) | rhodium | all Cs | $R^1$ is a hydrogen atom, and $R^2$ to $R^5$ are methyl groups | $R^8$ and $R^{11}$ are phenolic hydroxyl groups, and $R^6$ to $R^7$, $R^9$ to $R^{10}$, and $R^{12}$ to $R^{13}$ are hydrogen atoms |
| (609) | cobalt | all Cs | all methyl groups | $R^8$ and $R^{11}$ are phenolic hydroxyl groups, and $R^6$ to $R^7$, $R^9$ to $R^{10}$, and $R^{12}$ to $R^{13}$ are hydrogen atoms |
| (610) | cobalt | all Cs | $R^1$ is a hydrogen atom, and $R^2$ to $R^5$ are methyl groups | $R^8$ and $R^{11}$ are phenolic hydroxyl groups, and $R^6$ to $R^7$, $R^9$ to $R^{10}$, and $R^{12}$ to $R^{13}$ are hydrogen atoms |
| (611) | iridium | $Q^9$ and $Q^{10}$ are N atoms, and $Q^6$ to $Q^8$ and $Q^{11}$ to $Q^{13}$ are C atoms | all methyl groups | $R^8$ and $R^{11}$ are phenolic hydroxyl groups, and $R^6$ to $R^7$, $R^9$ to $R^{10}$, $R^{12}$ to $R^{13}$ are hydrogen atoms |

TABLE 19

(Examples of the complex represented by the formula (6))

| Compound No. | M | $Q^6$ to $Q^{13}$ | $R^1$ to $R^5$ | $R^6$ to $R^{13}$ |
|---|---|---|---|---|
| (612) | iridium | $Q^9$ and $Q^{10}$ are N atoms, and $Q^6$ to $Q^8$ and $Q^{11}$ to $Q^{13}$ are C atoms | $R^1$ is a hydrogen atom, and $R^2$ to $R^5$ are methyl groups | $R^8$ and $R^{11}$ are phenolic hydroxyl groups, and $R^6$ to $R^7$, $R^9$ to $R^{10}$, and $R^{12}$ to $R^{13}$ are hydrogen atoms |
| (613) | rhodium | $Q^9$ and $Q^{10}$ are N atoms, and $Q^6$ to $Q^8$ and $Q^{11}$ to $Q^{13}$ are C atoms | all methyl groups | $R^8$ and $R^{11}$ are phenolic hydroxyl groups, and $R^6$ to $R^7$, $R^9$ to $R^{10}$, and $R^{12}$ to $R^{13}$ are hydrogen atoms |
| (614) | rhodium | $Q^9$ and $Q^{10}$ are N atoms, and $Q^6$ to $Q^8$ and $Q^{11}$ to $Q^{13}$ are C atoms | $R^1$ is a hydrogen atom, and $R^2$ to $R^5$ are methyl groups | $R^8$ and $R^{11}$ are phenolic hydroxyl groups, and $R^6$ to $R^7$, $R^9$ to $R^{10}$, and $R^{12}$ to $R^{13}$ are hydrogen atoms |
| (615) | cobalt | $Q^9$ and $Q^{10}$ are N atoms, and $Q^6$ to $Q^8$ and $Q^{11}$ to $Q^{13}$ are C atoms | all methyl groups | $R^8$ and $R^{11}$ are phenolic hydroxyl groups, and $R^6$ to $R^7$, $R^9$ to $R^{10}$, and $R^{12}$ to $R^{13}$ are hydrogen atoms |
| (616) | cobalt | $Q^9$ and $Q^{10}$ are N atoms, and $Q^6$ to $Q^8$ and $Q^{11}$ to $Q^{13}$ are C atoms | $R^1$ is a hydrogen atom, and $R^2$ to $R^5$ are methyl groups | $R^8$ and $R^{11}$ are phenolic hydroxyl groups, and $R^6$ to $R^7$, $R^9$ to $R^{10}$, and $R^{12}$ to $R^{13}$ are hydrogen atoms |

TABLE 20

(Examples of the complex represented by the formula (7) ($Q^0$ in each compound is a nitrogen atom or a carbon atom))

| Compound No. | M | $Q^6$ to $Q^{12}$ | $R^0$ to $R^5$ | $R^6$ to $R^{12}$ |
|---|---|---|---|---|
| (701) | iridium | all Cs | all methyl groups | $R^7$ is a phenolic hydroxyl group, and $R^6$ and $R^8$ to $R^{12}$ are all hydrogen atoms |
| (702) | iridium | all Cs | all methyl groups | $R^7$ is a phenolic hydroxyl group, and $R^6$ and $R^8$ to $R^{12}$ are all hydrogen atoms |
| (703) | iridium | all Cs | $R^1$ is a hydrogen atom, and $R^2$ to $R^5$ are methyl groups | $R^7$ is a phenolic hydroxyl group, and $R^6$ and $R^8$ to $R^{12}$ are all hydrogen atoms |
| (704) | iridium | all Cs | all hydrogen atoms | $R^7$ is a phenolic hydroxyl group, and $R^6$ and $R^8$ to $R^{12}$ are all hydrogen atoms |
| (705) | iridium | all Cs | all methyl groups | $R^7$ is a phenolic hydroxyl group, $R^{10}$ and $R^{12}$ are methyl groups and $R^5$ to $R^6$, $R^8$ to $R^9$, and $R^{11}$ are all hydrogen atoms |

TABLE 21

(Examples of the complex represented by the formula (7) ($Q^0$ in each compound is a nitrogen atom or a carbon atom))

| Compound No. | M | $Q^6$ to $Q^{12}$ | $R^0$ to $R^5$ | $R^6$ to $R^{12}$ |
|---|---|---|---|---|
| (706) | iridium | all Cs | $R^1$ is a hydrogen atom, and $R^2$ to $R^5$ are methyl groups | $R^7$ is a phenolic hydroxyl group, $R^{10}$ and $R^{12}$ are methyl groups, and $R^5$ to $R^6$, $R^8$ to $R^9$, and $R^{11}$ are all hydrogen atoms |
| (707) | iridium | all Cs | all hydrogen atoms | $R^7$ is a phenolic hydroxyl group, $R^{10}$ and $R^{12}$ are methyl groups, and $R^5$ to $R^6$, $R^8$ to $R^9$, and $R^{11}$ are all hydrogen atoms |
| (708) | iridium | all Cs | all methyl groups | $R^7$ is a phenolic hydroxyl group, $R^{10}$ is a methyl group, and $R^5$ to $R^6$, $R^8$ to $R^9$, and $R^{11}$ to $R^{12}$ are all hydrogen atoms |
| (709) | iridium | all Cs | $R^1$ is a hydrogen atom, and $R^2$ to $R^5$ are methyl groups | $R^7$ is a phenolic hydroxyl group, $R^{10}$ is a methyl group, and $R^5$ to $R^6$, $R^8$ to $R^9$, and $R^{11}$ to $R^{12}$ are all hydrogen atoms |

TABLE 22

(Examples of the complex represented by the formula (7) ($Q^0$ in each compound is a nitrogen atom or a carbon atom))

| Compound No. | M | $Q^6$ to $Q^{12}$ | $R^0$ to $R^5$ | $R^6$ to $R^{12}$ |
|---|---|---|---|---|
| (710) | iridium | all Cs | all hydrogen atoms | $R^7$ is a phenolic hydroxyl group, $R^{10}$ is a methyl group, and $R^5$ to $R^6$, $R^8$ to $R^9$, and $R^{11}$ to $R^{12}$ are all hydrogen atoms |
| (711) | rhodium | all Cs | all methyl groups | $R^7$ is a phenolic hydroxyl group, and $R^6$ and $R^8$ to $R^{12}$ are all hydrogen atoms |
| (712) | rhodium | all Cs | $R^1$ is a hydrogen atom, and $R^2$ to $R^5$ are methyl groups | $R^7$ is a phenolic hydroxyl group, and $R^6$ and $R^8$ to $R^{12}$ are all hydrogen atoms |
| (713) | rhodium | all Cs | all hydrogen atoms | $R^7$ is a phenolic hydroxyl group, and $R^6$ and $R^8$ to $R^{12}$ are all hydrogen atoms |
| (714) | rhodium | all Cs | all methyl groups | $R^7$ is a phenolic hydroxyl group, $R^{10}$ and $R^{12}$ are methyl groups, and $R^5$ to $R^6$, $R^8$ to $R^9$, and $R^{11}$ are all hydrogen atoms |

TABLE 23

(Examples of the complex represented by the formula (7) ($Q^0$ in each compound is a nitrogen atom or a carbon atom))

| Compound No. | M | $Q^6$ to $Q^{12}$ | atom or atomic group $R^0$ to $R^5$ | $R^6$ to $R^{12}$ |
|---|---|---|---|---|
| (715) | rhodium | all Cs | $R^1$ is a hydrogen atom, and $R^2$ to $R^5$ are methyl groups | $R^7$ is a phenolic hydroxyl group, $R^{10}$ and $R^{12}$ are methyl groups, and $R^5$ to $R^6$, $R^8$ to $R^9$, and $R^{11}$ are all hydrogen atoms |
| (716) | rhodium | all Cs | all hydrogen atoms | $R^7$ is a phenolic hydroxyl group, $R^{10}$ and $R^{12}$ are methyl groups, and $R^5$ to $R^6$, $R^8$ to $R^9$, and $R^{11}$ are all hydrogen atoms |
| (717) | rhodium | all Cs | all methyl groups | $R^7$ is a phenolic hydroxyl group, $R^{10}$ is a methyl group, and $R^5$ to $R^6$, $R^8$ to $R^9$, and $R^{11}$ to $R^{12}$ are all hydrogen atoms |
| (718) | rhodium | all Cs | $R^1$ is a hydrogen atom, and $R^2$ to $R^5$ are methyl groups | $R^7$ is a phenolic hydroxyl group, $R^{10}$ is a methyl group, and $R^5$ to $R^6$, $R^8$ to $R^9$, and $R^{11}$ to $R^{12}$ are all hydrogen atoms |

TABLE 24

(Examples of the complex represented by the formula (7) ($Q^0$ in each compound is a nitrogen atom or a carbon atom))

| Compound No. | M | $Q^6$ to $Q^{12}$ | atom or atomic group $R^0$ to $R^5$ | $R^6$ to $R^{12}$ |
|---|---|---|---|---|
| (719) | rhodium | all Cs | all hydrogen atoms | $R^7$ is a phenolic hydroxyl group, $R^{10}$ is a methyl group, and $R^5$ to $R^6$, $R^8$ to $R^9$, and $R^{11}$ to $R^{12}$ are all hydrogen atoms |
| (720) | rhodium | all Cs | all methyl groups | $R^7$ is a phenolic hydroxyl group, and $R^6$ and $R^8$ to $R^{12}$ are all hydrogen atoms |
| (721) | cobalt | all Cs | all methyl groups | $R^7$ is a phenolic hydroxyl group, and $R^6$ and $R^8$ to $R^{12}$ are all hydrogen atoms |
| (722) | cobalt | all Cs | $R^1$ is a hydrogen atom, and $R^2$ to $R^5$ are methyl groups | $R^7$ is a phenolic hydroxyl group, and $R^6$ and $R^8$ to $R^{12}$ are all hydrogen atoms |
| (723) | cobalt | all Cs | all hydrogen atoms | $R^7$ is a phenolic hydroxyl group, and $R^6$ and $R^8$ to $R^{12}$ are all hydrogen atoms |

TABLE 25

(Examples of the complex represented by the formula (7) ($Q^0$ in each compound is a nitrogen atom or a carbon atom))

| Compound No. | M | $Q^6$ to $Q^{12}$ | atom or atomic group $R^0$ to $R^5$ | $R^6$ to $R^{12}$ |
|---|---|---|---|---|
| (724) | cobalt | all Cs | all methyl groups | $R^7$ is a phenolic hydroxyl group, $R^{10}$ and $R^{12}$ are methyl groups, and $R^5$ to $R^6$, $R^8$ to $R^9$, and $R^{11}$ are all hydrogen atoms |
| (725) | cobalt | all Cs | $R^1$ is a hydrogen atom, and $R^2$ to $R^5$ are methyl groups | $R^7$ is a phenolic hydroxyl group, $R^{10}$ and $R^{12}$ are methyl groups, and $R^5$ to $R^6$, $R^8$ to $R^9$, and $R^{11}$ are all hydrogen atoms |
| (726) | cobalt | all Cs | all hydrogen atoms | $R^7$ is a phenolic hydroxyl group, $R^{10}$ and $R^{12}$ are methyl groups, and $R^5$ to $R^6$, $R^8$ to $R^9$, and $R^{11}$ are all hydrogen atoms |
| (727) | cobalt | all Cs | all methyl groups | $R^7$ is a phenolic hydroxyl group, $R^{10}$ is a methyl group, and $R^5$ to $R^6$, $R^8$ to $R^9$, and $R^{11}$ to $R^{12}$ are all hydrogen atoms |

TABLE 26

(Examples of the complex represented by the formula (7) ($Q^0$ in each compound is a nitrogen atom or a carbon atom))

| Compound No. | M | $Q^6$ to $Q^{12}$ | atom or atomic group $R^0$ to $R^5$ | $R^6$ to $R^{12}$ |
|---|---|---|---|---|
| (728) | cobalt | all Cs | $R^1$ is a hydrogen atom, and $R^2$ to $R^5$ are methyl groups | $R^7$ is a phenolic hydroxyl group, $R^{10}$ is a methyl group, $R^5$ to $R^6$, $R^8$ to $R^9$, and $R^{11}$ to $R^{12}$ are all hydrogen atoms |
| (729) | cobalt | all Cs | all hydrogen atoms | $R^7$ is a phenolic hydroxyl group, $R^{10}$ is a methyl group, $R^5$ to $R^6$, $R^8$ to $R^9$, and $R^{11}$ to $R^{12}$ are all hydrogen atoms |
| (730) | iridium | all Cs | all methyl groups | $R^7$ is a sulfo group (sulfonate group), and $R^6$ and $R^8$ to $R^{12}$ are all hydrogen atoms |
| (731) | iridium | all Cs | $R^1$ is a hydrogen atom, and $R^2$ to $R^5$ are methyl groups | $R^7$ is a sulfo group (sulfonate group), and $R^6$ and $R^8$ to $R^{12}$ are all hydrogen atoms |
| (732) | iridium | all Cs | all hydrogen atoms | $R^7$ is a sulfo group (sulfonate group), and $R^6$ and $R^8$ to $R^{12}$ are all hydrogen atoms |

TABLE 27

(Examples of the complex represented by the formula (7)
($Q^0$ in each compound is a nitrogen atom or a carbon atom))

| Compound No. | M | $Q^6$ to $Q^{12}$ | $R^0$ to $R^5$ | $R^6$ to $R^{12}$ |
|---|---|---|---|---|
| (733) | iridium | all Cs | all methyl groups | $R^7$ is a sulfo group (sulfonate group), $R^{10}$ and $R^{12}$ are methyl groups, and $R^5$ to $R^6$, $R^8$ to $R^9$, and $R^{11}$ are all hydrogen atoms |
| (734) | iridium | all Cs | $R^1$ is a hydrogen atom, and $R^2$ to $R^5$ are methyl groups | $R^7$ is a sulfo group (sulfonate group), $R^{10}$ and $R^{12}$ are methyl groups, and $R^5$ to $R^6$, $R^8$ to $R^9$, and $R^{11}$ are all hydrogen atoms |
| (735) | iridium | all Cs | all hydrogen atoms | $R^7$ is a sulfo group (sulfonate group), $R^{10}$ and $R^{12}$ are methyl groups, and $R^5$ to $R^6$, $R^8$ to $R^9$, and $R^{11}$ are all hydrogen atoms |

TABLE 28

(Examples of the complex represented by the formula (7)
($Q^0$ in each compound is a nitrogen atom or a carbon atom))

| Compound No. | M | $Q^6$ to $Q^{12}$ | $R^0$ to $R^5$ | $R^6$ to $R^{12}$ |
|---|---|---|---|---|
| (736) | iridium | all Cs | all methyl groups | $R^7$ is a sulfo group (sulfonate group), $R^{10}$ is a methyl group, and $R^5$ to $R^6$, $R^8$ to $R^9$, and $R^{11}$ to $R^{12}$ are all hydrogen atoms |
| (737) | iridium | all Cs | $R^1$ is a hydrogen atom, and $R^2$ to $R^5$ are methyl groups | $R^7$ is a sulfo group (sulfonate group), $R^{10}$ is a methyl group, and $R^5$ to $R^6$, $R^8$ to $R^9$, and $R^{11}$ to $R^{12}$ are all hydrogen atoms |
| (738) | iridium | all Cs | all hydrogen atoms | $R^7$ is a sulfo group (sulfonate group), $R^{10}$ is a methyl group, and $R^5$ to $R^6$, $R^8$ to $R^9$, and $R^{11}$ to $R^{12}$ are all hydrogen atoms |
| (739) | rhodium | all Cs | all methyl groups | $R^7$ is a sulfo group (sulfonate group), and $R^6$ and $R^8$ to $R^{12}$ are all hydrogen atoms |

TABLE 29

(Examples of the complex represented by the formula (7)
($Q^0$ in each compound is a nitrogen atom or a carbon atom))

| Compound No. | M | $Q^6$ to $Q^{12}$ | $R^0$ to $R^5$ | $R^6$ to $R^{12}$ |
|---|---|---|---|---|
| (740) | rhodium | all Cs | $R^1$ is a hydrogen atom, and $R^2$ to $R^5$ are methyl groups | $R^7$ is a sulfo group (sulfonate group), and $R^6$ and $R^8$ to $R^{12}$ are all hydrogen atoms |
| (741) | rhodium | all Cs | all hydrogen atoms | $R^7$ is a sulfo group (sulfonate group), and $R^6$ and $R^8$ to $R^{12}$ are all hydrogen atoms |
| (742) | rhodium | all Cs | all methyl groups | $R^7$ is a sulfo group (sulfonate group), $R^{10}$ and $R^{12}$ are methyl groups, and $R^5$ to $R^6$, $R^8$ to $R^9$, and $R^{11}$ are all hydrogen atoms |
| (743) | rhodium | all Cs | $R^1$ is a hydrogen atom, and $R^2$ to $R^5$ are methyl groups | $R^7$ is a sulfo group (sulfonate group), $R^{10}$ and $R^{12}$ are methyl groups, and $R^5$ to $R^6$, $R^8$ to $R^9$, and $R^{11}$ are all hydrogen atoms |

TABLE 30

(Examples of the complex represented by the formula (7)
($Q^0$ in each compound is a nitrogen atom or a carbon atom))

| Compound No. | M | $Q^6$ to $Q^{12}$ | $R^0$ to $R^5$ | $R^6$ to $R^{12}$ |
|---|---|---|---|---|
| (744) | rhodium | all Cs | all hydrogen atoms | $R^7$ is a sulfo group (sulfonate group), $R^{10}$ and $R^{12}$ are methyl groups, and $R^5$ to $R^6$, $R^8$ to $R^9$, and $R^{11}$ are all hydrogen atoms |
| (745) | rhodium | all Cs | all methyl groups | $R^7$ is a sulfo group (sulfonate group), $R^{10}$ is a methyl group, and $R^5$ to $R^6$, $R^8$ to $R^9$, and $R^{11}$ to $R^{12}$ are all hydrogen atoms |
| (746) | rhodium | all Cs | $R^1$ is a hydrogen atom, and $R^2$ to $R^5$ are methyl groups | $R^7$ is a sulfo group (sulfonate group), $R^{10}$ is a methyl group, and $R^5$ to $R^6$, $R^8$ to $R^9$, and $R^{11}$ to $R^{12}$ are all hydrogen atoms |
| (747) | rhodium | all Cs | all hydrogen atoms | $R^7$ is a sulfo group (sulfonate group), $R^{10}$ is a methyl group, and $R^5$ to $R^6$, $R^8$ to $R^9$, and $R^{11}$ to $R^{12}$ are all hydrogen atoms |

TABLE 31

(Examples of the complex represented by the formula (7)
($Q^0$ in each compound is a nitrogen atom or a carbon atom))

| Compound No. | M | $Q^6$ to $Q^{12}$ | atom or atomic group $R^0$ to $R^5$ | $R^6$ to $R^{12}$ |
|---|---|---|---|---|
| (748) | rhodium | all Cs | all methyl groups | $R^7$ is a sulfo group (sulfonate group), and $R^6$ and $R^8$ to $R^{12}$ are all hydrogen atoms |
| (749) | cobalt | all Cs | all methyl groups | $R^7$ is a sulfo group (sulfonate group), and $R^6$ and $R^8$ to $R^{12}$ are all hydrogen atoms |
| (750) | cobalt | all Cs | $R^1$ is a hydrogen atom, and $R^2$ to $R^5$ are methyl groups | $R^7$ is a sulfo group (sulfonate group), and $R^6$ and $R^8$ to $R^{12}$ are all hydrogen atoms |
| (751) | cobalt | all Cs | all hydrogen atoms | $R^7$ is a sulfo group (sulfonate group), and $R^6$ and $R^8$ to $R^{12}$ are all hydrogen atoms |
| (752) | cobalt | all Cs | all methyl groups | $R^7$ is a sulfo group (sulfonate group), $R^{10}$ and $R^{12}$ are methyl groups, and $R^5$ to $R^6$, $R^8$ to $R^9$, and $R^{11}$ are all hydrogen atoms |

TABLE 32

(Examples of the complex represented by the formula (7)
($Q^0$ in each compound is a nitrogen atom or a carbon atom))

| Compound No. | M | $Q^6$ to $Q^{12}$ | atom or atomic group $R^0$ to $R^5$ | $R^6$ to $R^{12}$ |
|---|---|---|---|---|
| (753) | cobalt | all Cs | $R^1$ is a hydrogen atom, and $R^2$ to $R^5$ are methyl groups | $R^7$ is a sulfo group (sulfonate group), $R^{10}$ and $R^{12}$ are methyl groups, and $R^5$ to $R^6$, $R^8$ to $R^9$, and $R^{11}$ are all hydrogen atoms |
| (754) | cobalt | all Cs | all hydrogen atoms | $R^7$ is a sulfo group (sulfonate group), $R^{10}$ and $R^{12}$ are methyl groups, and $R^5$ to $R^6$, $R^8$ to $R^9$, and $R^{11}$ are all hydrogen atoms |
| (755) | cobalt | all Cs | all methyl groups | $R^7$ is a sulfo group (sulfonate group), $R^{10}$ is a methyl group, and $R^5$ to $R^6$, $R^8$ to $R^9$, and $R^{11}$ to $R^{12}$ are all hydrogen atoms |

TABLE 33

(Examples of the complex represented by the formula (7)
($Q^0$ in each compound is a nitrogen atom or a carbon atom))

| Compound No. | M | $Q^6$ to $Q^{12}$ | atom or atomic group $R^0$ to $R^5$ | $R^6$ to $R^{12}$ |
|---|---|---|---|---|
| (756) | cobalt | all Cs | $R^1$ is a hydrogen atom, and $R^2$ to $R^5$ are methyl groups | $R^7$ is a sulfo group (sulfonate group), $R^{10}$ is a methyl group, and $R^5$ to $R^6$, $R^8$ to $R^9$, and $R^{11}$ to $R^{12}$ are all hydrogen atoms |
| (757) | cobalt | all Cs | all hydrogen atoms | $R^7$ is a sulfo group (sulfonate group), $R^{10}$ is a methyl group, and $R^5$ to $R^6$, $R^8$ to $R^9$, and $R^{11}$ to $R^{12}$ are all hydrogen atoms |
| (758) | cobalt | all Cs | all methyl groups | $R^7$ is a sulfo group (sulfonate group), and $R^6$ and $R^8$ to $R^{12}$ are all hydrogen atoms |

TABLE 34

(Examples of the complex represented by the formula (8))

| Compound No. | M | $Q^6$ to $Q^{15}$ | atom or atomic group $R^0$ to $R^5$ | $R^6$ to $R^{15}$ |
|---|---|---|---|---|
| (801) | iridium | all Cs | all methyl groups | $R^7$ is a phenolic hydroxyl group, and $R^6$ and $R^8$ to $R^{15}$ are all hydrogen atoms |
| (802) | iridium | all Cs | all methyl groups | $R^7$ is a sulfo group (sulfonate group), and $R^6$ and $R^8$ to $R^{15}$ are all hydrogen atoms |
| (803) | iridium | all Cs | all methyl groups | $R^7$ is a hydroxymethyl group, and $R^6$ and $R^8$ to $R^{15}$ are all hydrogen atoms |
| (804) | iridium | all Cs | all methyl groups | $R^7$ is a phosphate group, and $R^6$ and $R^8$ to $R^{15}$ are all hydrogen atoms |
| (805) | iridium | all Cs | all methyl groups | $R^8$ and $R^{13}$ are phenolic hydroxyl groups, and $R^6$ to $R^7$, $R^{10}$ to $R^{11}$, and $R^{14}$ to $R^{15}$ are hydrogen atoms |
| (806) | iridium | all Cs | $R^1$ is a hydrogen atom, and $R^2$ to $R^5$ are methyl groups | $R^8$ and $R^{13}$ are phenolic hydroxyl groups, and $R^6$ to $R^7$, $R^{10}$ to $R^{11}$, and $R^{14}$ to $R^{15}$ are hydrogen atoms |

TABLE 35

(Examples of the complex represented by the formula (8))

| Compound No. | M | $Q^6$ to $Q^{15}$ | $R^0$ to $R^5$ | $R^6$ to $R^{15}$ |
|---|---|---|---|---|
| (807) | rhodium | all Cs | all methyl groups | $R^8$ and $R^{13}$ are phenolic hydroxyl groups, and $R^6$ to $R^7$, $R^{10}$ to $R^{11}$, and $R^{14}$ to $R^{15}$ are hydrogen atoms |
| (808) | rhodium | all Cs | $R^1$ is a hydrogen atom, and $R^2$ to $R^5$ are methyl groups | $R^8$ and $R^{13}$ are phenolic hydroxyl groups, and $R^6$ to $R^7$, $R^{10}$ to $R^{11}$, and $R^{14}$ to $R^{15}$ are hydrogen atoms |
| (809) | cobalt | all Cs | all methyl groups | $R^8$ and $R^{13}$ are phenolic hydroxyl groups, and $R^6$ to $R^7$, $R^{10}$ to $R^{11}$, and $R^{14}$ to $R^{15}$ are hydrogen atoms |
| (810) | cobalt | all Cs | $R^1$ is a hydrogen atom, and $R^2$ to $R^5$ are methyl groups | $R^8$ and $R^{13}$ are phenolic hydroxyl groups, and $R^6$ to $R^7$, $R^{10}$ to $R^{11}$, and $R^{14}$ to $R^{15}$ are hydrogen atoms |
| (811) | iridium | all Cs | all methyl groups | $R^{10}$ and $R^{11}$ are phenolic hydroxyl groups, and $R^6$ to $R^8$ and $R^{13}$ to $R^{15}$ are hydrogen atoms |

TABLE 36

(Examples of the complex represented by the formula (8))

| Compound No. | M | $Q^6$ to $Q^{15}$ | $R^0$ to $R^5$ | $R^6$ to $R^{15}$ |
|---|---|---|---|---|
| (812) | iridium | all Cs | $R^1$ is a hydrogen atom, and $R^2$ to $R^5$ are methyl groups | $R^{10}$ and $R^{11}$ are phenolic hydroxyl groups, and $R^6$ to $R^8$ and $R^{13}$ to $R^{15}$ are hydrogen atoms |
| (813) | rhodium | all Cs | all methyl groups | $R^{10}$ and $R^{11}$ are phenolic hydroxyl groups, and $R^6$ to $R^8$ and $R^{13}$ to $R^{15}$ are hydrogen atoms |
| (814) | rhodium | all Cs | $R^1$ is a hydrogen atom, and $R^2$ to $R^5$ are methyl groups | $R^{10}$ and $R^{11}$ are phenolic hydroxyl groups, and $R^6$ to $R^8$ and $R^{13}$ to $R^{15}$ are hydrogen atoms |
| (815) | cobalt | all Cs | all methyl groups | $R^{10}$ and $R^{11}$ are phenolic hydroxyl groups, and $R^6$ to $R^8$ and $R^{13}$ to $R^{15}$ are hydrogen atoms |
| (816) | cobalt | all Cs | $R^1$ is a hydrogen atom, and $R^2$ to $R^5$ are methyl groups | $R^{10}$ and $R^{11}$ are phenolic hydroxyl groups, and $R^6$ to $R^8$ and $R^{13}$ to $R^{15}$ are hydrogen atoms |

TABLE 37

(Examples of the complex represented by the formula (9))

| Compound No. | M | $Q^6$ to $Q^{13}$ | $R^0$ to $R^5$ | $R^6$ to $R^{13}$ |
|---|---|---|---|---|
| (901) | iridium | all Cs | all methyl groups | $R^7$ is a phenolic hydroxyl group, and $R^6$ and $R^8$ to $R^{13}$ are all hydrogen atoms |
| (902) | iridium | all Cs | all methyl groups | $R^7$ is a sulfo group (sulfonate group), and $R^6$ and $R^8$ to $R^{13}$ are all hydrogen atoms |
| (903) | iridium | all Cs | all methyl groups | $R^7$ is a hydroxymethyl group, and $R^6$ and $R^8$ to $R^{13}$ are all hydrogen atoms |
| (904) | iridium | all Cs | all methyl groups | $R^7$ is a phosphate group, and $R^6$ and $R^8$ to $R^{15}$ are all hydrogen atoms |
| (905) | iridium | all Cs | all methyl groups | $R^8$ and $R^{11}$ are phenolic hydroxyl groups, and $R^6$ to $R^7$, $R^9$ to $R^{10}$, and $R^{12}$ to $R^{13}$ are hydrogen atoms |
| (906) | iridium | all Cs | $R^1$ is a hydrogen atom, and $R^2$ to $R^5$ are methyl groups | $R^8$ and $R^{11}$ are phenolic hydroxyl groups, and $R^6$ to $R^7$, $R^9$ to $R^{10}$, and $R^{12}$ to $R^{13}$ are hydrogen atoms |

TABLE 38

(Examples of the complex represented by the formula (9))

| Compound No. | M | $Q^6$ to $Q^{13}$ | $R^0$ to $R^5$ | $R^6$ to $R^{13}$ |
|---|---|---|---|---|
| (907) | rhodium | all Cs | all methyl groups | $R^8$ and $R^{11}$ are phenolic hydroxyl groups, and $R^6$ to $R^7$, $R^9$ to $R^{10}$, and $R^{12}$ to $R^{13}$ are hydrogen atoms |
| (908) | rhodium | all Cs | $R^1$ is a hydrogen atom, and $R^2$ to $R^5$ are methyl groups | $R^8$ and $R^{11}$ are phenolic hydroxyl groups, and $R^6$ to $R^7$, $R^9$ to $R^{10}$, and $R^{12}$ to $R^{13}$ are hydrogen atoms |
| (909) | cobalt | all Cs | all methyl groups | $R^8$ and $R^{11}$ are phenolic hydroxyl groups, and $R^6$ to $R^7$, $R^9$ to $R^{10}$, and $R^{12}$ to $R^{13}$ are hydrogen atoms |
| (910) | cobalt | all Cs | $R^1$ is a hydrogen atom, and $R^2$ to $R^5$ are methyl groups | $R^8$ and $R^{11}$ are phenolic hydroxyl groups, and $R^6$ to $R^7$, $R^9$ to $R^{10}$, and $R^{12}$ to $R^{13}$ are hydrogen atoms |

TABLE 38-continued (Examples of the complex represented by the formula (9))

| Compound No. | M | $Q^6$ to $Q^{13}$ | $R^0$ to $R^5$ | $R^6$ to $R^{13}$ |
|---|---|---|---|---|
| (911) | iridium | $Q^9$ and $Q^{10}$ are N atoms, and $Q^6$ to $Q^8$ and $Q^{11}$ to $Q^{13}$ are C atoms | all methyl groups | $R^8$ and $R^{11}$ are phenolic hydroxyl groups, and $R^6$ to $R^7$, $R^9$ to $R^{10}$, and $R^{12}$ to $R^{13}$ are hydrogen atoms |

TABLE 39

(Examples of the complex represented by the formula (9))

| Compound No. | M | $Q^6$ to $Q^{13}$ | $R^0$ to $R^5$ | $R^6$ to $R^{13}$ |
|---|---|---|---|---|
| (912) | iridium | $Q^9$ and $Q^{10}$ are N atoms, and $Q^6$ to $Q^8$ and $Q^{11}$ to $Q^{13}$ are C atoms | $R^1$ is a hydrogen atom, and $R^2$ to $R^5$ are methyl groups | $R^8$ and $R^{11}$ are phenolic hydroxyl groups, and $R^6$ to $R^7$, $R^9$ to $R^{10}$, and $R^{12}$ to $R^{13}$ are hydrogen atoms |
| (913) | rhodium | $Q^9$ and $Q^{10}$ are N atoms, and $Q^6$ to $Q^8$ and $Q^{11}$ to $Q^{13}$ are C atoms | all methyl groups | $R^8$ and $R^{11}$ are phenolic hydroxyl groups, and $R^6$ to $R^7$, $R^9$ to $R^{10}$, and $R^{12}$ to $R^{13}$ are hydrogen atoms |
| (914) | rhodium | $Q^9$ and $Q^{10}$ are N atoms, and $Q^6$ to $Q^8$ and $Q^{11}$ to $Q^{13}$ are C atoms | $R^1$ is a hydrogen atom, and $R^2$ to $R^5$ are methyl groups | $R^8$ and $R^{11}$ are phenolic hydroxyl groups, and $R^6$ to $R^7$, $R^9$ to $R^{10}$, and $R^{12}$ to $R^{13}$ are hydrogen atoms |
| (915) | cobalt | $Q^9$ and $Q^{10}$ are N atoms, and $Q^6$ to $Q^8$ and $Q^{11}$ to $Q^{13}$ are C atoms | all methyl groups | $R^8$ and $R^{11}$ are phenolic hydroxyl groups, and $R^6$ to $R^7$, $R^9$ to $R^{10}$, and $R^{12}$ to $R^{13}$ are hydrogen atoms |
| (916) | cobalt | $Q^9$ and $Q^{10}$ are N atoms, and $Q^6$ to $Q^8$ and $Q^{11}$ to $Q^{13}$ are C atoms | $R^1$ is a hydrogen atom, and $R^2$ to $R^5$ are methyl groups | $R^8$ and $R^{11}$ are phenolic hydroxyl groups, and $R^6$ to $R^7$, $R^9$ to $R^{10}$, and $R^{12}$ to $R^{13}$ are hydrogen atoms |

When the mononuclear metal complex represented by the formula (1) has isomers such as tautomers and stereoisomers (e.g.: a geometric isomer, a conformer, and an optical isomer), these isomers also can be used in the present invention. For example, when the mononuclear metal complex has enantiomers, both an R-enantiomer and an S-enantiomer can be used. Furthermore, salts of the mononuclear metal complex represented by the formula (1) and salts of the isomers of the mononuclear metal complex also can be used in the present invention. In the salt, a counter ion for the mononuclear metal complex represented by the formula (1) is not particularly limited. Examples of an anion that serves as the counter ion include a hexafluorophosphate ion ($PF_6^-$), a tetrafluoroborate ion ($BF_4^-$), a hydroxide ion ($OH^-$), an acetate ion, a carbonate ion, a phosphate ion, a sulfate ion, a nitrate ion, halide ions (e.g., fluoride ion ($F^-$), a chloride ion ($Cl^-$), a bromide ion ($Br^-$), and an iodide ion ($I^-$)), a hypohalite ion (e.g., a hypofluorite ion, a hypochlorite ion, a hypobromite ion, and a hypoiodite ion), halite ions (e.g., a fluorite ion, a chlorite ion, a bromite ion, and an iodite ion), halate ions (e.g., a fluorate ion, a chlorate ion, a bromate ion, and an iodate ion), perhalate ions (e.g., a perfluorate ion, a perchlorate ion, a perbromate ion, and a periodate ion), a trifluoromethanesulfonate ion ($OSO_2CF_3^-$), and a tetrakis(pentafluorophenyl)borate ion [$B(C_6F_5)_4^-$]. A cation that serves as the counter ion is not particularly limited, and examples thereof include: various metal ions such as a lithium ion, a magnesium ion, a sodium ion, a potassium ion, a calcium ion, a barium ion, a strontium ion, an yttrium ion, a scandium ion, and a lanthanoid ion; and a hydrogen ion. Only one kind of these counter ions may be present, or two or more kinds of them may be present. The mononuclear metal complex represented by the formula (1) encompasses those in which any atom is substituted with an isotope. Specifically, for example, the hydrogen atom (H) of the ligand may be substituted with a heavy hydrogen (D) or tritium (T).

In the present invention, the alkyl group is not particularly limited, and examples thereof include a methyl group, an ethyl group, an n-propyl group, an isopropyl group, an n-butyl group, an isobutyl group, a sec-butyl group, a tert-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, and an icosyl group. The same applies to groups and atomic groups (alkoxy groups etc.) derived from alkyl groups. The alcohol and alkoxide ion is not particularly limited, and examples thereof include alcohol and alkoxide ions derived from the above-described alkyl groups. Aldehyde and ketone are not particularly limited, and examples thereof include: aldehyde and ketone derived from the above-described alkyl groups; and aldehyde and ketone obtained by oxidizing the above-described alcohols. In the present invention, the term "halogen" refers to any halogen element, examples of which include fluorine, chlorine, bromine, and iodine. Furthermore, in the present invention, when a substituent or the like has isomers, any isomer can be used unless otherwise stated. For example, when it is simply referred to as a "propyl group", it may be either an n-propyl group or an isopropyl group. When it is simply referred to as a "butyl group", it may be any of an n-butyl group, an isobutyl group, a sec-butyl group, or a tert-butyl group.

[Method for Producing Mononuclear Metal Complex]

The method for producing a mononuclear metal complex represented by the formula (1), a tautomer or stereoisomer thereof, or a salt thereof (hereinafter they may altogether be referred to simply as a "compound (1)") is not particularly limited, and any method can be used.

The compound (1) can be synthesized (produced) according to Scheme 1 below, for example.

Scheme 1

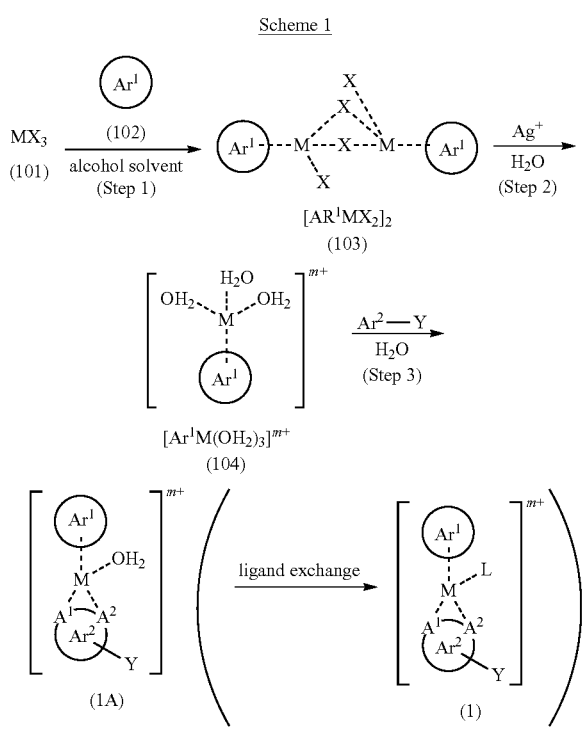

Scheme 1 can be carried out in the following manner, for example. The reaction conditions such as the reaction temperature, the reaction time, the solvent, and the like merely are illustrative examples. They are not limited to those described below, and can be changed as appropriate.

(Step 1)

Step 1 in Scheme 1 can be carried out by setting reaction conditions as appropriate with reference to, for example, Kenichi Fujita, Yoshinori Takahashi, Maki Owaki, Kazunari Yamamoto, and Ryohei Yamaguchi, Organic. Letters., 2004, 6, pp. 2785-2788, and the like. Specifically, Step 1 can be carried out in the following manner, for example. First, $MX_3$ (Compound (101), where X is a halogen) is dissolved in an alcohol solvent (methanol, ethanol, or the like) to prepare a solution. $MX_3$ may be a hydrate or the like, for example. The concentration of $MX_3$ is not particularly limited, and is, for example, 0.01 to 10 mol/l, preferably 0.01 to 5 mol/l, and more preferably 0.1 to 1 mol/l. To this solution, $Ar^1$ (Compound (102), whose structure is as shown in Scheme 1) is added in an inert gas (nitrogen, argon, or the like) atmosphere to cause a reaction. Thus, a desired complex $[Ar^1RMX_2]_2$ (103) is obtained. The amount of substance (the number of moles) of $Ar^1$ is not particularly limited. It is, for example, 1 to 20 times, preferably 1 to 10 times, and more preferably 1 to 5 times the amount of substance (the number of moles) of $MX_3$. The reaction temperature is not particularly limited, and is, for example, 30° C. to 64° C., preferably 50° C. to 64° C., and more preferably 55° C. to 62° C. Also, the reaction time is not particularly limited, and is, for example, 1 to 30 hours, preferably 10 to 24 hours, and more preferably 15 to 24 hours. After the completion of the reaction, the obtained complex (103) may be, for example, isolated or purified when necessary, or may be subjected to a subsequent reaction step without being isolated or purified, for example. The method for carrying out the isolation, purification, or the like is not particularly limited, and the isolation, purification, or the like can be carried out by an ordinary method. For example, methods such as evaporation, filtration, washing, column chromatography, and recrystallization can be used either alone or in an appropriate combination.

(Step 2)

Step 2 in Scheme 1 can be carried out by setting reaction conditions as appropriate with reference to, for example, Andrew Nutton, Pamela M. Bailey, and Peter M. Maitlis. Journal of the Chemical Society, Dalton Transactions. 1981, 9, pp. 1997-2002 or Moris S. Eisen, Ariel Haskel, Hong Chen, Marilyn M. Olmstead, David P. Smith, Marcos F. Maestre, and Richard H. Fish. Organometallics, 1995, 14, pp. 2806-2812. Specifically, Step 2 can be carried out in the following manner, for example. First, an aqueous solution of silver salt (e.g., $Ag_2SO_4$ or the like) is prepared. The concentration of the silver salt is not particularly limited, and is, for example, 0.1 to 28 mmol/l, preferably 1 to 27 mmol/l, and more preferably 10 to 27 mmol/l. To this aqueous solution, the complex $[Ar^1MX_2]_2$ (103) produced in Step 1 was added in an inert gas (nitrogen, argon, or the like) atmosphere to cause a reaction. Thus, a desired complex $[Ar^1M(OH_2)_3]^{m+}$ (104) is obtained. This reaction preferably is carried out in the dark, for example, but the present invention is not limited thereto. The reaction temperature is not particularly limited, and can be set as appropriate. The reaction time is not particularly limited, and is, for example 0.5 to 10 hours, preferably 0.5 to 5 hours, and more preferably 2 to 5 hours. The amount of substance (the number of moles) of the silver salt is not particularly limited. It is, for example, 1 to 2 times, preferably 1 to 1.5 times, and more preferably 1 to 1.05 times the amount of substance (the number of moles) of the complex $[Ar^1MX_2]_2$ (103). After the completion of the reaction, the obtained complex (104) may be, for example, isolated or purified when necessary, or may be subjected to a subsequent reaction step without being isolated or purified, for example. The method for carrying out the isolation, purification, or the like is not particularly limited, and the isolation, purification, or the like can be carried out by an ordinary method. For example, methods such as evaporation, filtration, washing, column chromatography, recrystallization, counter anion-exchange precipitation can be used either alone or in an appropriate combination.

Step 3 in Scheme 1 can be carried out by setting reaction conditions as appropriate with reference to, for example, Seiji Ogo, Hideki Hayashi, Keiji Uehara, and Shunichi Fukuzumi, Applied Organometallic Chemistry, 2005, 19, pp. 639-643; H. Christine Lo, Carmen Leiva, Olivier Buriez, John B. Kerr, Marilyn M. Olmstead; Richard H. Fish, Inorganic Chemistry, 2001, 40, pp. 6705-6716; and the like. Specifically, Step 3 can be carried out in the following manner, for example. First, an aqueous solution of $Ar^2$ (the ligand having aromaticity in the chemical formula (1)) is prepared. The concentration of $Ar^2$ is not particularly limited, and is, for example, 0.01 to 0.4 mol/l, preferably 0.1 to 0.4 mol/l, and more preferably 0.1 to 0.3 mol/l. To this aqueous solution, a salt (e.g., sulfate) of the complex $[Ar^1M(OH_2)_3]^{m+}$ (104) produced in Step 2 is added in an inert gas (nitrogen, argon, or the like) atmosphere to cause a reaction. Thus, a desired mononuclear metal complex (1A) is obtained. This reaction preferably is carried out in the dark, for example, but the present invention is not limited thereto. The reaction temperature is not particularly limited, and can be set as appropriate. Also, the reaction time is not particularly limited, and is, for example, 1 to 30 hours, preferably 3 to 25 hours, and more preferably 5 to 20 hours. The amount of substance (the number of moles) of the Ar is not particularly limited. It is, for example, 1 to 2 times, preferably 1 to 1.5 times, and more preferably 1 to 1.05 times the amount of substance (the number of moles) of the complex [Ar¹M(OH₂)₃]^{m+} (104).

After the completion of the reaction, the product (1A) may be, for example, isolated or purified when necessary, or may be used as it is without being isolated or purified, for example. The method for carrying out the isolation, purification, or the like is not particularly limited, and the isolation, purification, or the like can be carried out by an ordinary method. For example, methods such as evaporation, filtration, washing, column chromatography, recrystallization, counter anion-exchange, and precipitation can be used either alone or in an appropriate combination. This mononuclear metal complex (1A) is the mononuclear metal complex (1) where the ligand L is a water molecule. Thus, this mononuclear metal complex (1A) may be used as it is in the present invention, or may be used after being subjected to ligand exchange or the like as appropriate when necessary. The method for carrying out the ligand exchange is not particularly limited, and any appropriate method can be used.

The desired compound (1) (or (1A)) can be produced in the manner described above.

The counter ion for the complex [Ar¹M(OH₂)₃]_{m+} (104) is not particularly limited, and examples thereof are the same as those described above as specific examples of the counter ion for the mononuclear metal complex (1). The same applies to counter ions of other ionic substances. In each of Steps 1 to 3, the reaction solvent is not limited to those described above, and it may be water or an appropriate organic solvent, for example. Only one kind of reaction solvent may be used, or two or more kinds of reaction solvents may be used in combination. However, when water can be used as the reaction solvent, e.g., when each reaction substance (raw material) is soluble in water, it is particularly preferable to use water in terms of cost efficiency, ease of reaction, etc. For the same reason, an alcohol solvent such as methanol or ethanol is preferable as the reaction solvent. The organic solvent is not particularly limited. Preferably, the organic solvent is a highly polar solvent from the viewpoint of the solubility of the reaction substance (raw material) and the like. Examples of the highly polar solvent include: nitriles such as acetonitrile, propionitrile, butyronitrile, and benzonitrile; primary alcohols such as methanol, ethanol, n-propyl alcohol, and n-butyl alcohol; secondary alcohols such as isopropyl alcohol and s-butyl alcohol; tertiary alcohols such as t-butyl alcohol; polyhydric alcohols such as ethylene glycol and propylene glycol; ethers such as tetrahydrofuran, dioxane, dimethoxyethane, and diethyl ether; amides such as dimethylformamide and dimethylacetamide; sulfoxide such as dimethyl sulfoxide; and esters such as ethyl acetate.

Among various mononuclear metal complexes (1), for example, the iridium mononuclear metal complex represented by the chemical formula (13), a tautomer or stereoisomer thereof, or a salt thereof can be produced according to Scheme 2 below, for example. Scheme 2 below can be carried out in the same manner as Scheme 1, except that reaction substances are selected according to the structure of the desired end product (the compound represented by the chemical formula (13)).

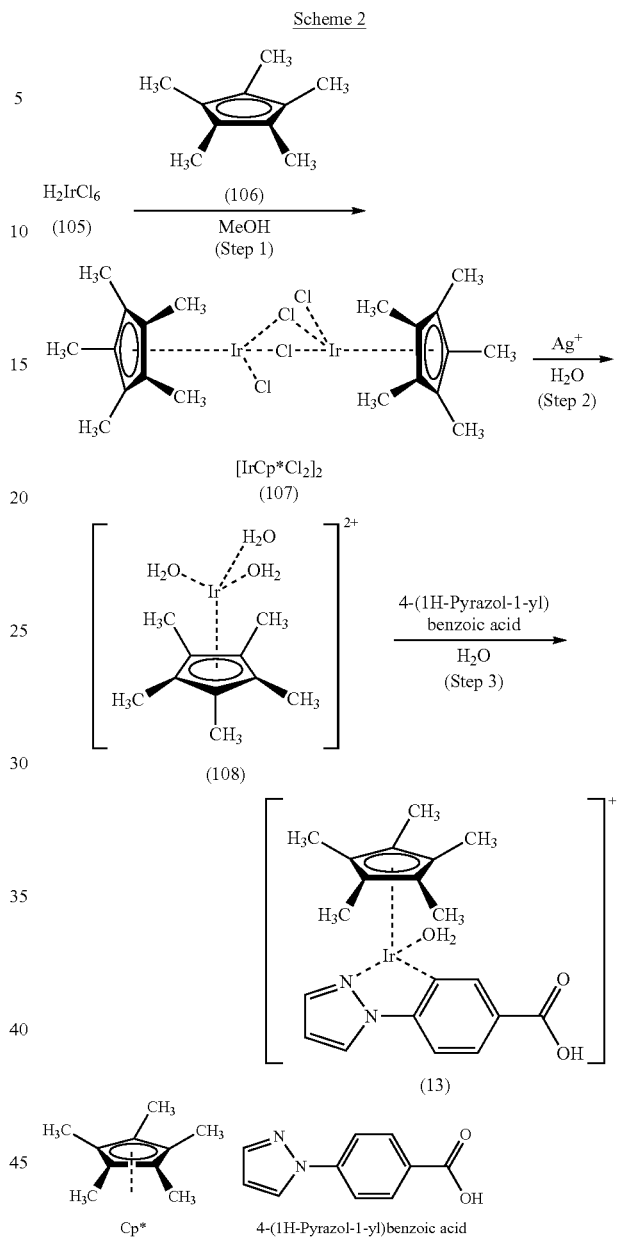

Among various mononuclear metal complexes (1), for example, the iridium mononuclear metal complex represented by the chemical formula (16), a tautomer or stereoisomer thereof, or a salt thereof can be produced according to Scheme 2, except that p-pyrazol-1-yl-benzene sulfonic acid is used instead of 4-(1H-pyrazol-1-yl)benzoic acid in Scheme 2, for example.

Heretofore, it has been very difficult to form a a bond between a transition metal and carbon. The inventors of the present invention discovered that the a bond between a transition metal and carbon can be formed easily by merely mixing the metal complex and the ligand in a solvent and heating the mixture as shown in, for example, Step 3 in Scheme 1 or 2. In the case where the reaction of Step 3 does not proceed smoothly owing to the structure or the like of the mononuclear metal complex (1), a microwave reactor or the like may be used as appropriate to cause the reaction, for example.

Although the compound (1) of the present invention can be produced (synthesized) in the manner described above, the method for producing the compound (1) of the present invention is not limited thereto, and any method may be used to produce the compound (1) of the present invention. For example, the compound (1) of the present invention may be produced as appropriate with reference to the above description and known methods for producing a metal complex.

[Hydrogenation Reduction Catalyst (Carbon Dioxide Fixation Catalyst) and Method for Producing Hydrogenation Reduction Product (Method for Producing Formic Acid)]

As described above, the hydrogenation reduction catalyst according to the present invention includes the mononuclear metal complex according to the present invention, a tautomer or stereoisomer thereof, or a salt thereof. Also, as described above, the method for producing a hydrogenation reduction product according to the present invention is a method for producing a hydrogenation reduction product by hydrogenating a substance to be reduced, including the step of in a solution or disperse system that contains the hydrogenation reduction catalyst according to the present invention, the substance to be reduced, and hydrogen ($H_2$), reducing the substance to be reduced by a reaction between the substance to be reduced and the hydrogen ($H_2$). The substance to be reduced is not particularly limited, and may be, for example, carbon dioxide, an aldehyde, a ketone, oxidized nicotinamide-adenine dinucleotide (NAD+), an oxidized water-soluble quinone (e.g., oxidized coenzyme $Q_{10}$), an oxidized flavin coenzyme analog (e.g., oxidized riboflavin), dehydroascorbic acid, tannin, oxidized glutathione, aldonic acid, aldaric acid, or allantoin. The aldehyde is not particularly limited, and may be either an aromatic aldehyde or an aliphatic aldehyde. The aliphatic aldehyde is, for example, an aldehyde derived from a straight-chain or branched alkyl group, and the alkyl group is as described above, for example. More specifically, examples of the aliphatic aldehyde include formaldehyde, acetaldehyde, propionaldehyde, 2-methylpropionaldehyde, and butylaldehyde. The ketone is not particularly limited, and may be either an aromatic ketone or an aliphatic ketone. The aliphatic ketone is, for example, a ketone derived from a straight-chain or branched alkyl group, and the alkyl group is as described above, for example. More specifically, examples of the aliphatic ketone include acetone and 2-butanone. The hydrogenation reduction product is not particularly limited, and may be, for example, formic acid, an alcohol, reduced nicotinamide-adenine dinucleotide (NADH), a reduced water-soluble hydroquinone (e.g., reduced coenzyme $Q_{10}$), vitamin $B_2$ (a reduced flavin coenzyme analog, which also is referred to as reduced riboflavin, for example), vitamin C (also referred to as ascorbic acid), a flavonoid (e.g., catechin or quercetin), glutathione, a reducing sugar (e.g., any of monosaccharides, invert sugars, maltose disaccharides, and oligosaccharides), or uric acid. The alcohol is not particularly limited, and may be either an aromatic alcohol or an aliphatic alcohol. The aliphatic alcohol is, for example, an alcohol derived from a straight-chain or branched alkyl group, and the alkyl group is as described above, for example. More specifically, examples of the aliphatic alcohol include methanol, ethanol, 1-propanol, 2-propanol, 2-methyl-1-propanol, 1-butanol, and 2-butanol. The hydrogenation reduction product in the present invention may be a substance resulting from hydrogenation of the substance to be reduced itself, or may be a changed form of such a substance. For example, when the substance to be reduced is carbon dioxide, the hydrogenation reduction product may be formic acid, or also may be a formate ion or the like.

Preferably, the substance to be reduced is carbon dioxide. When carbon dioxide is reduced by hydrogenation, formic acid can be obtained as the hydrogenation reduction product. Such a method for producing formic acid also can be referred to as a method for fixing carbon dioxide. That is, the hydrogenation reduction catalyst according to the present invention preferably is a carbon dioxide fixation catalyst, and the method for producing a hydrogenation reduction product according to the present invention preferably is a method for producing formic acid (method for fixing carbon dioxide). The following description mainly is directed to the carbon dioxide fixation catalyst according to the present invention and the method for producing formic acid (method for fixing carbon dioxide) according to the present invention.

The carbon dioxide fixation catalyst according to the present invention includes the mononuclear metal complex represented by the formula (1), a tautomer or stereoisomer thereof, or a salt thereof (the compound (1)). For example, the compound (1) itself may be used as the carbon dioxide fixation catalyst of the present invention, or any other component may be added to the compound (1) as appropriate and the resultant mixture may be used as the carbon dioxide fixation catalyst of the present invention. The carbon dioxide fixation catalyst according to the present invention acts to react carbon dioxide with hydrogen ($H_2$) to fix the carbon dioxide, thereby generating (producing) formic acid. That is, the carbon dioxide fixation catalyst according to the present invention also serves as a formic acid production catalyst for producing formic acid.

The method for producing formic acid according to the present invention includes the step of in a solution or disperse system that contains the carbon dioxide fixation catalyst according to the present invention, carbon dioxide, and hydrogen ($H_2$), reacting carbon dioxide with hydrogen ($H_2$) to fix the carbon dioxide, thereby producing formic acid. In the present invention, the term "carbon dioxide" encompasses not only carbon dioxide ($CO_2$) present in the form of molecule, but also, for example, a carbonate ion ($CO_3^{2-}$) and a bicarbonate ion ($HCO_3^-$) present in the form of an ion in the solution or disperse system.

The carbon dioxide fixing step (formic acid producing step) is not particularly limited as long as the carbon dioxide can react with the hydrogen ($H_2$) in the solution or disperse system to fix the carbon dioxide, thereby producing formic acid. For example, the carbon dioxide fixing step may be carried out by allowing the solution or the disperse system to stand, by heating the solution, or by irradiating the solution with light. The method for causing the carbon dioxide to react with the hydrogen ($H_2$) in the solution or disperse system is not particularly limited. For example, the reaction may be caused by blowing carbon dioxide in advance under deoxygenated conditions to an aqueous solution containing the carbon dioxide fixation catalyst according to the present invention dissolved therein to cause bubbling, and then blowing hydrogen ($H_2$) and carbon dioxide into the aqueous solution at the same time to cause bubbling. Examples of the method for performing qualitative and quantitative analyses of the formic acid generated by the carbon dioxide fixing step include liquid chromatography and $^1$H-NMR. However, when the quantitative analysis is performed by high performance liquid chromatography, it may not be possible to make a precise analysis owing to contaminants in the sample to be analyzed. Thus, from the viewpoint of reliability of the analysis, it is preferable to perform quantitative analysis by $^1$H-NMR. For the quantification of the generated formic acid, TSP (3-(trimethylsilyl)-3,3,2,2-propionic acid-$d_4$) is used as the internal standard, for example.

The temperature condition for carrying out the carbon dioxide fixing step is not particularly limited. For example, the carbon dioxide fixing step may be carried out at a temperature in the range from 15° C. to 80° C., preferably from 15° C. to 70° C., more preferably from 15° C. to 60° C., and particularly preferably at room temperature (a temperature in the range from 15° C. to 30° C.). When the carbon dioxide fixing step is carried out at room temperature, heating or the like is not necessary, so that energy such as heat used in the production of formic acid can be reduced, for example. As a result, it is possible to produce formic acid in an energy-saving manner and at low cost, for example.

The pressure condition for carrying out the carbon dioxide fixing step is not particularly limited. For example, the carbon dioxide fixing step may be carried out at a pressure in the range from 0.01 to 10 MPa, preferably from 0.05 to 1 MPa, more preferably from 0.1 to 0.2 MPa, and particularly preferably at atmospheric pressure. The term "atmospheric pressure" encompasses a pressure of 0.1 MPa and pressures around 0.1 MPa. Specifically, the atmospheric pressure is in the range from 0.09 to 0.12 MPa, for example. When the carbon dioxide fixing step is carried out at atmospheric pressure, pressurization or the like is not necessary, so that energy for applying a pressure used in the production of formic acid can be reduced, for example. As a result, it is possible to produce formic acid in an energy-saving manner and at low cost, for example.

In the method for producing formic acid according to the present invention, a solvent or dispersion medium used in the solution or disperse system is not particularly limited, and may be, for example, water, an organic solvent, or a mixed solvent of water and an organic solvent. When an organic solvent is to be used, only one kind of organic solvent may be used, or two or more kinds of organic solvents may be used in combination. When the compound (1) is soluble in water, it is possible to use water (an aqueous solution is provided). This is preferable because it is not necessary to use an organic solvent. It is to be noted, however, that the present invention is not limited thereto. The organic solvent is not particularly limited. From the viewpoint of the solubility or the like of the compound (1), a highly polar solvent is preferable. Examples of the highly polar solvent include: nitriles such as acetonitrile, propionitrile, butyronitrile, and benzonitrile; primary alcohols such as methanol, ethanol, n-propyl alcohol, and n-butyl alcohol; secondary alcohols such as isopropyl alcohol and s-butyl alcohol; tertiary alcohols such as t-butyl alcohol; polyhydric alcohols such as ethylene glycol and propylene glycol; ethers such as tetrahydrofuran, dioxane, dimethoxyethane, and diethyl ether; amides such as dimethylformamide and dimethylacetamide; sulfoxides such as dimethyl sulfoxide; and esters such as ethyl acetate.

In the method for producing formic acid according to the present invention, when the solution is an aqueous solution, the pH of the aqueous solution is not particularly limited. The pH of the aqueous solution preferably is in the range from −3 to 14, more preferably from 0 to 10, and particularly preferably from 7.5 to 9.9.

In the method for producing formic acid according to the present invention, the concentration of the mononuclear metal complex (1) molecules in the solution or disperse system is not particularly limited, and is, for example, 0.01 to 1 mol/l (M), preferably 0.01 to 0.5 mol/l (M), and more preferably 0.01 to 0.25 mol/l (M). The amount-of-substance ratio (the ratio of the number of molecules) between the mononuclear metal complex (1) molecules and the formic acid molecules also is not particularly limited, and is, for example, 1:1 to 1:5000000, preferably 1:10 to 1:50000, and more preferably 1:100 to 1:10000.

In the method for producing formic acid according to the present invention, the concentration of bicarbonate ions ($HCO_3^-$) in the aqueous solution or disperse system is not particularly limited, and is, for example, 0.01 to 3 mol/l (M), preferably 0.1 to 2 mol/l (M), and more preferably 1 to 2 mol/l (M). The amount-of-substance ratio (the ratio of the number of molecules) between the mononuclear metal complex (1) molecules and the bicarbonate ions ($HCO_3^-$) also is not particularly limited, and is, for example, 1:1 to 1:5000000, preferably 1:10 to 1:50000, and more preferably 1:100 to 1:10000.

The carbon dioxide fixation catalyst described in Non-Patent Document 1 can cause carbon dioxide to be reduced by hydrogen in an aqueous solution at ordinary temperature and ordinary pressure, thereby generating formic acid. However, this carbon dioxide fixation catalyst has low catalytic activity. The catalytic activity of the carbon dioxide fixation catalyst according to the present invention is not particularly limited. Preferably, it is higher than the catalytic activity of the carbon dioxide fixation catalyst described in Non-Patent Document 1. For example, it is particularly preferable that the carbon dioxide fixation catalyst according to the present invention can exhibit a catalytic function in an aqueous solution at room temperature, even if the aqueous solution is not heated at all. It is to be noted, however, that the present invention is not limited thereto. For example, even when the carbon dioxide fixation catalyst according to the present invention has sufficiently high catalytic activity, the aqueous solution may be heated as appropriate, an organic solvent may be used instead of water, or water and an organic solvent may be used in combination as described above, for the purpose of, for example, further improving the reaction efficiency.

The mononuclear metal catalyst of the present invention, which serves as a carbon dioxide fixation catalyst, reacts carbon dioxide with hydrogen ($H_2$) to fix the carbon dioxide, thereby producing formic acid. Thus, according to the carbon dioxide fixation catalyst of the present invention, it is possible to store hydrogen, which is attracting attention as a source of next-generation energy, in the form of formic acid, which is a safe compound. Furthermore, according to the carbon dioxide fixation catalyst of the present invention, it is possible to store carbon dioxide emitted through burning of fossil fuel and the like by a beneficial method for utilizing the carbon dioxide, namely, producing formic acid by reacting the carbon dioxide with hydrogen. The use of the carbon dioxide fixation catalyst of the present invention is not limited to those described above. The carbon dioxide fixation catalyst of the present invention can be used in any technical field where the supply of formic acid is necessary, for example.

Furthermore, in the method for producing a hydrogenation reduction product according to the present invention, when the hydrogenation reduction product is a substance other than formic acid, the method can be carried out in the same manner as the formic acid production method of the present invention, except that a substance to be reduced other than carbon dioxide is used instead of the carbon dioxide, for example.

[Dehydrogenation Catalyst (Formic Acid Decomposition Catalyst), Method for Producing Hydrogen ($H_2$), and Method for Producing Dehydrogenation Reaction Product]

As described above, the dehydrogenation catalyst according to the present invention includes the mononuclear metal complex according to the present invention, a tautomer or stereoisomer thereof, or a salt thereof. Furthermore, as described above, the method for producing hydrogen ($H_2$)

according to the present invention includes the step of in a solution or disperse system that contains the dehydrogenation catalyst according to the present invention and a hydrogen source, decomposing the hydrogen source to generate hydrogen ($H_2$). Still further, as described above, the method for producing a dehydrogenation reaction product according to the present invention includes the step of in a solution or disperse system that contains the dehydrogenation catalyst according to the present invention and a hydrogen source, decomposing the hydrogen source to generate a dehydrogenation reaction product. The hydrogen source is not particularly limited, and may be the same as the reduction product obtained in the method for producing a reduction product according to the present invention, for example. Specifically, the hydrogen source may be, for example, formic acid, an alcohol, reduced nicotinamide-adenine dinucleotide (NADH), a reduced water-soluble hydroquinone (e.g., reduced coenzyme $Q_{10}$), vitamin $B_2$ (a reduced flavin coenzyme analog, which also is referred to as reduced riboflavin, for example), vitamin C (also referred to as ascorbic acid), a flavonoid (e.g., catechin or quercetin), glutathione, a reducing sugar (e.g., any of monosaccharides, invert sugars, maltose disaccharides, and oligosaccharides), or uric acid. The alcohol is not particularly limited, and may be either an aromatic alcohol or an aliphatic alcohol. The aliphatic alcohol is, for example, an alcohol derived from a straight-chain or branched alkyl group, and the alkyl group is as described above, for example. More specifically, examples of the aliphatic alcohol include methanol, ethanol, 1-propanol, 2-propanol, 2-methyl-1-propanol, 1-butanol, and 2-butanol. When the hydrogen source is decomposed to generate hydrogen ($H_2$), a decomposition product (a dehydrogenation reaction product resulting from the dehydrogenation of the hydrogen source) is generated as a by-product. Thus, the method for producing hydrogen according to the present invention also can be referred to as a method for oxidizing the hydrogen source or a method for producing the decomposition product (the dehydrogenation reaction product resulting from the dehydrogenation of the hydrogen source). The decomposition product (the reaction product resulting from the dehydrogenation) generated as a by-product is not particularly limited. For example, the decomposition product is the same as the substance to be reduced in the method for producing a hydrogenation reduction product according to the present invention. Specifically, the decomposition product may be, for example, carbon dioxide, an aldehyde, a ketone, oxidized nicotinamide-adenine dinucleotide (NAD+), an oxidized water-soluble quinone (e.g., oxidized coenzyme $Q_{10}$), an oxidized flavin coenzyme analog (e.g., oxidized riboflavin), dehydroascorbic acid, tannin, oxidized glutathione, aldonic acid, aldaric acid, or allantoin. The aldehyde is not particularly limited, and may be either an aromatic aldehyde or an aliphatic aldehyde. The aliphatic aldehyde is, for example, an aldehyde derived from a straight-chain or branched alkyl group, and the alkyl group is as described above, for example. More specifically, examples of the aliphatic aldehyde include formaldehyde, acetaldehyde, propionaldehyde, 2-methylpropionaldehyde, and butylaldehyde. The ketone is not particularly limited, and may be either an aromatic ketone or an aliphatic ketone. The aliphatic ketone is, for example, a ketone derived from a straight-chain or branched alkyl group, and the alkyl group is as described above, for example. More specifically, examples of the aliphatic ketone include acetone and 2-butanone. The dehydrogenation reaction product in the present invention may be a substance itself resulting from the dehydrogenation of the hydrogen source, or may be a changed form of such a substance. For example, when the hydrogen source is formic acid, the dehydrogenation reaction product may be carbon dioxide, or also may be a carbonate ion, a bicarbonate ion, or the like. In the hydrogen production method or dehydrogenation reaction product production method according to the present invention, the generated hydrogen and dehydrogenation reaction product both may be collected and utilized, or only the required one may be collected and utilized, for example.

The hydrogen source preferably is formic acid. In this case, the dehydrogenation catalyst according to the present invention also can be referred to as a formic acid decomposition catalyst. The following description mainly is directed to the cases where the hydrogen source is formic acid.

The formic acid decomposition catalyst according to the present invention includes a mononuclear metal complex represented by the formula (1), a tautomer or stereoisomer thereof, or a salt thereof (compound (1)). For example, the compound (1) itself may be used as the formic acid decomposition catalyst of the present invention, or any other component may be added to the compound (1) as appropriate and the resultant mixture may be used as the formic acid decomposition catalyst of the present invention. The formic acid decomposition catalyst of the present invention acts to decompose formic acid, thereby generating (producing) hydrogen ($H_2$) and carbon dioxide ($CO_2$). That is, the formic acid decomposition catalyst of the present invention also can be referred to as a hydrogen ($H_2$) production catalyst for producing hydrogen ($H_2$).

The method for producing hydrogen ($H_2$) according to the present invention include the step of in a solution or disperse system that contains the formic acid decomposition catalyst according to the present invention and formic acid, decomposing the formic acid to generate hydrogen ($H_2$).

The hydrogen producing step (formic acid decomposing step) is not particularly limited as long as the formic acid can be decomposed to generate hydrogen in the solution or disperse system. For example, the hydrogen producing step may be carried out by allowing the solution or disperse system to stand, by heating the solution or disperse system, or by irradiating the solution or disperse system with light. That is, for example, the hydrogen producing step may be carried out by adding formic acid to a solution or disperse system of the compound (1) and then either allowing the solution or disperse system to stand or subjecting the solution or disperse system to heating or light irradiation as necessary. The method for collecting hydrogen ($H_2$) generated by the hydrogen producing step is not particularly limited, and a known method such as collection over water or upward delivery can be used as appropriate, for example. Examples of the method for analyzing the hydrogen ($H_2$) generated by the hydrogen producing step include gas chromatography.

The temperature condition for carrying out the hydrogen producing step is not particularly limited. For example, the hydrogen producing step may be carried out at a temperature in the range from 15° C. to 80° C., preferably from 15° C. to 60° C., more preferably from 15° C. to 50° C., and particularly preferably at room temperature (a temperature in the range from 15° C. to 30° C.). When the hydrogen producing step is carried out at room temperature, heating or the like is not necessary, so that energy such as heat used in the production of hydrogen ($H_2$) can be reduced, for example. As a result, it is possible to produce hydrogen ($H_2$) in an energy-saving manner and at low cost, for example.

The pressure condition for carrying out the hydrogen producing step is not particularly limited. For example, the hydrogen producing step may be carried out at a pressure in the range from 0.01 to 10 MPa, preferably from 0.05 to 1

MPa, more preferably from 0.1 to 0.2 MPa, and particularly preferably at atmospheric pressure. The term "atmospheric pressure" encompasses a pressure of 0.1 MPa and pressures around 0.1 MPa. Specifically, the atmospheric pressure is in the range from 0.09 to 0.12 MPa, for example. When the hydrogen producing step is carried out under the atmospheric pressure, pressurization or the like is not necessary, so that energy for applying pressure used in the production of formic acid can be reduced, for example. As a result, it is possible to produce hydrogen ($H_2$) in an energy-saving manner and at low cost, for example.

In the method for producing hydrogen ($H_2$) according to the present invention, a solvent or dispersion medium used in the solution or disperse system is not particularly limited, and may be, for example, water or an organic solvent. Only one kind of solvent or dispersion medium may be used, or two or more kinds of solvents or dispersion media may be used in combination. When the compound (1) is soluble in water, it is possible to use water (an aqueous solution is provided). This is preferable because it is not necessary to use an organic solvent. It is to be noted, however, that the present invention is not limited thereto. The organic solvent is not particularly limited, and examples thereof include those described above as examples of the organic solvent to be used in the method for producing formic acid. The formic acid to be added to the solution or the disperse system may be in the form of a solution, salt, or the like, for example.

In the method for producing hydrogen ($H_2$) according to the present invention, when the solution is an aqueous solution, the pH of the aqueous solution is not particularly limited. The pH of the aqueous solution preferably is in the range from −3 to 14, more preferably from 0 to 10, and particularly preferably not less than 1 and less than 9.

In the method for producing hydrogen ($H_2$) according to the present invention, the concentration of the mononuclear metal complex (1) molecules in the solution or disperse system is not particularly limited, and is, for example, 0.001 to 50 mmol/l, preferably 0.005 to 20 mmol/l, and more preferably 0.005 to 5 mmol/l. The amount-of-substance ratio (the ratio of the number of molecules) between the mononuclear metal complex (1) molecules and the formic acid molecules also is not particularly limited, and is, for example 1:1 to 1:5000000, preferably 1:10 to 1:50000, and more preferably 1:100 to 1:10000.

In the method for producing hydrogen ($H_2$) according to the present invention, the concentration of the formic acid in the aqueous solution is not particularly limited, and is, for example, 0.001 to 5 mol/l (M), preferably 0.005 to 4 mol/l (M), and more preferably 0.01 to 3.3 mol/l (M). The amount-of-substance ratio (the ratio of the number of molecules) between the mononuclear metal complex (1) molecules and the formic acid also is not particularly limited, and is, for example, 1:1 to 1:5000000, preferably 1:10 to 1:50000, and more preferably 1:100 to 1:10000, as described above.

The hydrogen production method or dehydrogenation reaction product production method according to the present invention can be carried out in the same manner as in the above, except that a hydrogen source other than formic acid is used instead of the formic acid, for example.

Conventional formic acid decomposition catalysts have a problem in that they have low catalytic activities, so that they do not exhibit their catalytic functions unless they are in an organic solvent, a strongly acidic or strongly basic aqueous solution, or a mixed solution thereof and besides, they are heated, for example. The catalytic activity of the formic acid decomposition catalyst according to the present invention is not particularly limited. Preferably, it is higher than the catalytic activities of the conventional formic acid decomposition catalysts. For example, it is particularly preferable that the formic acid decomposition catalyst according to the present invention can exhibit a catalytic function in an aqueous solution at room temperature, even if the aqueous solution is not heated at all. It is to be noted, however, that the present invention is not limited thereto. For example, even when the formic acid decomposition catalyst of the present invention has sufficiently high catalytic activity, the aqueous solution may be heated as appropriate, an organic solvent may be used instead of water, or water and an organic solvent may be used in combination as described above, for the purpose of, for example, further improving the reaction efficiency.

The formic acid decomposition catalyst of the present invention also allows hydrogen ($H_2$) to be supplied stably, for example, under mild conditions at room temperature using formic acid, which is a safe substance, as a raw material. When hydrogen ($H_2$) is generated by the decomposition of the formic acid, carbon dioxide ($CO_2$) is generated as a by-product. Thus, the method for producing hydrogen ($H_2$) according to the present invention also can be used as a method for producing carbon dioxide ($CO_2$). More specifically, this method for producing carbon dioxide ($CO_2$) includes the step of decomposing formic acid by the formic acid decomposition catalyst according to the present invention, thereby generating carbon dioxide ($CO_2$). The method for producing hydrogen ($H_2$) according to the present invention does not produce any by-product other than carbon dioxide ($CO_2$), so that it is possible to obtain hydrogen without producing any toxic by-product.

The mononuclear metal catalyst according to the present invention can be used as a formic acid decomposition catalyst in, for example, a formic acid fuel cell or the like. When applied to a fuel cell, it is only necessary that, for example, the formic acid decomposition catalyst of the present invention is included inside the fuel cell and that the fuel cell is provided with the mechanism for decomposing formic acid to generate hydrogen by the above-described method. The specific structure of the fuel cell is not particularly limited, and the structure and the like of known fuel cells can be applied as appropriate, for example. The use of the formic acid decomposition catalyst of the present invention is not limited to those described above. The formic acid decomposition catalyst of the present invention can be used in any technical field where the supply of hydrogen ($H_2$) is necessary, for example.

As described above, the mononuclear metal complex according to the present invention can exhibit both the function of a hydrogenation reduction catalyst (e.g., a carbon dioxide fixation catalyst) and the function of a dehydrogenation catalyst (e.g., a formic acid decomposition catalyst). Such a mononuclear metal complex is newly discovered by the inventors of the present invention. Heretofore, for example, an iridium-ruthenium dinuclear metal complex has been proposed that decomposes formic acid in water at ordinary temperature and ordinary pressure to produce hydrogen (WO 2008/059630). Also, there have been proposed a formic acid decomposition catalyst and a rhodium mononuclear metal catalyst that can provide hydrogen ($H_2$) safely, efficiently, and at low cost in an aqueous solution at ordinary temperature and ordinary pressure (JP 2009-78200 A). However, the mononuclear metal complex of the present invention is the first metal complex that can exhibit both the function of a carbon dioxide fixation catalyst and the function of a formic acid decomposition catalyst. The interconversion between these functions may be achieved by, for example, changing the pH of an aqueous solution of the mononuclear metal complex of the present invention. Since the mononuclear metal complex of the present invention can exhibit both the functions as described above, it allows hydrogen ($H_2$) to be stored in the form of formic acid in an organic solvent-free (containing no organic solvent) aqueous solution at ordinary temperature and ordinary pressure (at room temperature and atmospheric pressure), for example. On the other hand, the mononuclear metal complex of the present invention can decompose formic acid at ordinary temperature (room temperature), so that it allows on-site production of hydrogen ($H_2$) by decomposing formic acid when it is needed. That is, for example, according to the present invention, with the use of a single catalyst, it is possible to clear up the most critical problems that humankind faces today to deal with environmental and energy problems, i.e., problems regarding production, storage, transport, and supply of hydrogen, as well as carbon dioxide reduction. It is to be noted, however, the use of the mononuclear metal complex of the present invention is by no means limited or restricted to those described above. For example, as described above, the carbon dioxide may be replaced with another substance to be reduced, and the formic acid may be replaced with another reduction product or hydrogen source. The use of the mononuclear metal complex of the present invention is not limited to the use as a hydrogenation reduction catalyst and a dehydrogenation catalyst, and the mononuclear metal complex of the present invention may be applied to any use.

EXAMPLES

Next, the present invention will be described with reference to examples. It is to be noted, however, that the present invention is by no means limited to the following examples.

[Measurement Conditions Etc.]

In the following examples, each reaction was followed by the ultraviolet-visible absorption spectroscopy, ESI-mass spectrometry, GC, and $^1$H-NMR. All the chemicals were of reagent grade. Formic acid was purchased from Wako Pure Chemical Industries, Ltd. Ultraviolet-visible absorption spectra (UV-Vis. spectra) were measured using a device manufactured by Shimadzu Corporation (trade name: UV-3100PC). Fluorescence spectra were measured using a device manufactured by Shimadzu Corporation (trade name: RF-5300PC). ESI-MS data was collected using an API-150 EX mass spectrometer (trade name, manufactured by PE-Sciex), which was equipped with an ion spray interface and operated in a positive detection mode. The voltage of the spray device was kept at +5.0 kV, and pressurized $N_2$ was used to help the spraying of liquid. $^1$H-NMR measurement was carried out using a nuclear magnetic resonance spectrometer manufactured by JEOL (trade name: JNM-AL300, 300.4 MHz at the time of $^1$H-NMR measurement). GC analysis was carried out using a device manufactured by Shimadzu Corporation (trade name: GC-14B). Elementary analysis was carried out using a device manufactured by Yanagimoto Mfg. Co., Ltd. (trade name: CHN-Corder (MT-2)). The amount of hydrogen generated in the formic acid decomposition reaction was measured by passing the generated gas through 5 mol/l (5M) NaOH water to remove carbon dioxide therefrom and then collecting only the hydrogen remaining in a measuring cylinder by collection over water.

Example 1

Production of Iridium Mononuclear Aqua Complex (13)

An iridium mononuclear aqua complex (13) was produced (synthesized) according to Scheme 2. This will be described specifically below.

(Step 1: Production of [Cp*IrCl$_2$]$_2$ (Complex (107)))

First, a solution was prepared by adding hexachloroiridium $H_2IrCl_6$ (1.02 g, 3.87 mmol) to methanol (6 ml). To this solution, $\eta^5$-pentamethylcyclopentadiene (1.5 ml) was added in an argon atmosphere. Then, still in the argon atmosphere, the solution was refluxed for 37 hours by being heated while stirring. Thereafter, the solution was cooled to 0° C. The resultant precipitates were collected by filtration using a glass filter (G4), washed with ether, and vacuum-dried. Thus, a desired complex (107), namely, [Cp*IrCl$_2$]$_2$, was obtained in the form of yellowish-brown powder (the yield calculated based on $H_2IrCl_6$: 73%). The instrumental analysis values of the [Cp*IrCl$_2$]$_2$ are shown below.

$^1$H-NMR (CDCl$_3$, 298 K): δ (ppm) 1.60 (s, $\eta^5$-C$_5$(CH$_3$)$_5$, 15H)

Elementary analysis: [Cp*IrCl$_2$]$_2$: C$_{20}$H$_{30}$Cl$_4$Ir$_2$: Theoretical values: C, 30.15%; H, 3.80%. Observed values: C, 30.14%; H, 3.72%.

(Step 2: Production of [Cp*Ir(H$_2$O)$_3$]$^{2+}$ (Complex (108)) Sulfate (Sulfate: Salt with Sulfuric Acid (SO$_4^{2-}$))

An aqueous solution was prepared by dissolving Ag$_2$SO$_4$ (0.83 g, 2.66 mmol) in water (70 ml). To this aqueous solution, the complex (107) produced in Step 1, namely, [Cp*IrCl$_2$]$_2$ (0.96 g, 1.32 mmol), was added in an argon gas atmosphere, and the resultant mixture was stirred in the dark for 5 hours at room temperature (25° C.). After the stirring, precipitates (AgCl) were collected by filtration using a glass filter (G4). The filtrate obtained was further filtered through a membrane filter (manufactured by ADVANTEC, made of PTFE (polytetrafluoroethylene)). This filtrate was evaporated to remove moisture therefrom and then was vacuum-dried. Thus, desired complex (108) sulfate, namely, [Cp*Ir(H$_2$O)$_3$]$^{2+}$ sulfate, was obtained in the form of orange powder (the yield calculated based on [Cp*IrCl$_2$]$_2$: 86%). The instrumental analysis values of the [Cp*Ir(H$_2$O)$_3$]$^{2+}$ sulfate are shown below.

$^1$H-NMR (DMSO-d$_6$, 298 K): δ (ppm) 1.68 (s, $\eta^5$-C$_5$(CH$_3$)$_5$, 15H), 3.31 (br, 3(H$_2$O), 6H).

Elementary analysis: [Cp*Ir(H$_2$O)$_3$]$^{2+}$ sulfate: C$_{10}$H$_{21}$O$_7$SIr: Theoretical values: C, 25.15%; H, 4.43%. Observed values: C, 25.39%; H, 4.48%.

(Step 3: Production of [IrCp*(4-(1H-Pyrazole-1-Yl-κN$^{2-}$) Benzoic Acid-κC$^3$)(H$_2$O)]$^+$ (Iridium Mononuclear Aqua Complex (13)) Sulfate)

Figure 17:
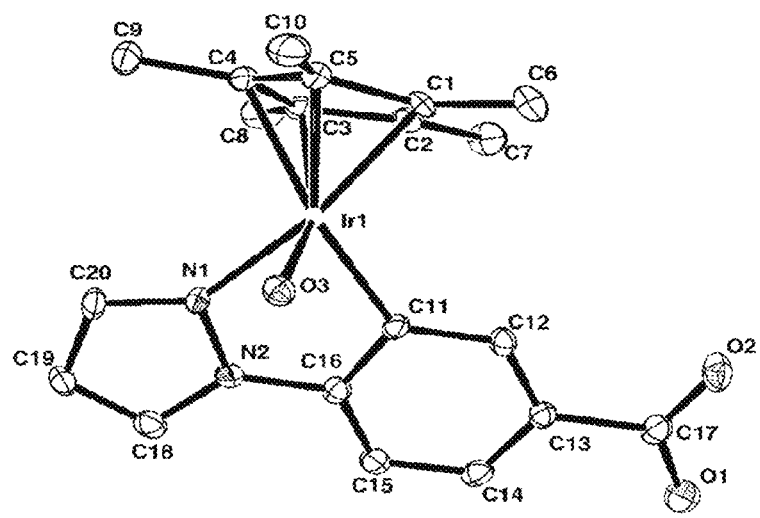
FIG. 17 shows an ORTEP diagram of the crystal structure of the iridium mononuclear aqua complex of Example 1, as well as analytical values of the iridium mononuclear aqua complex.
Figure 22:
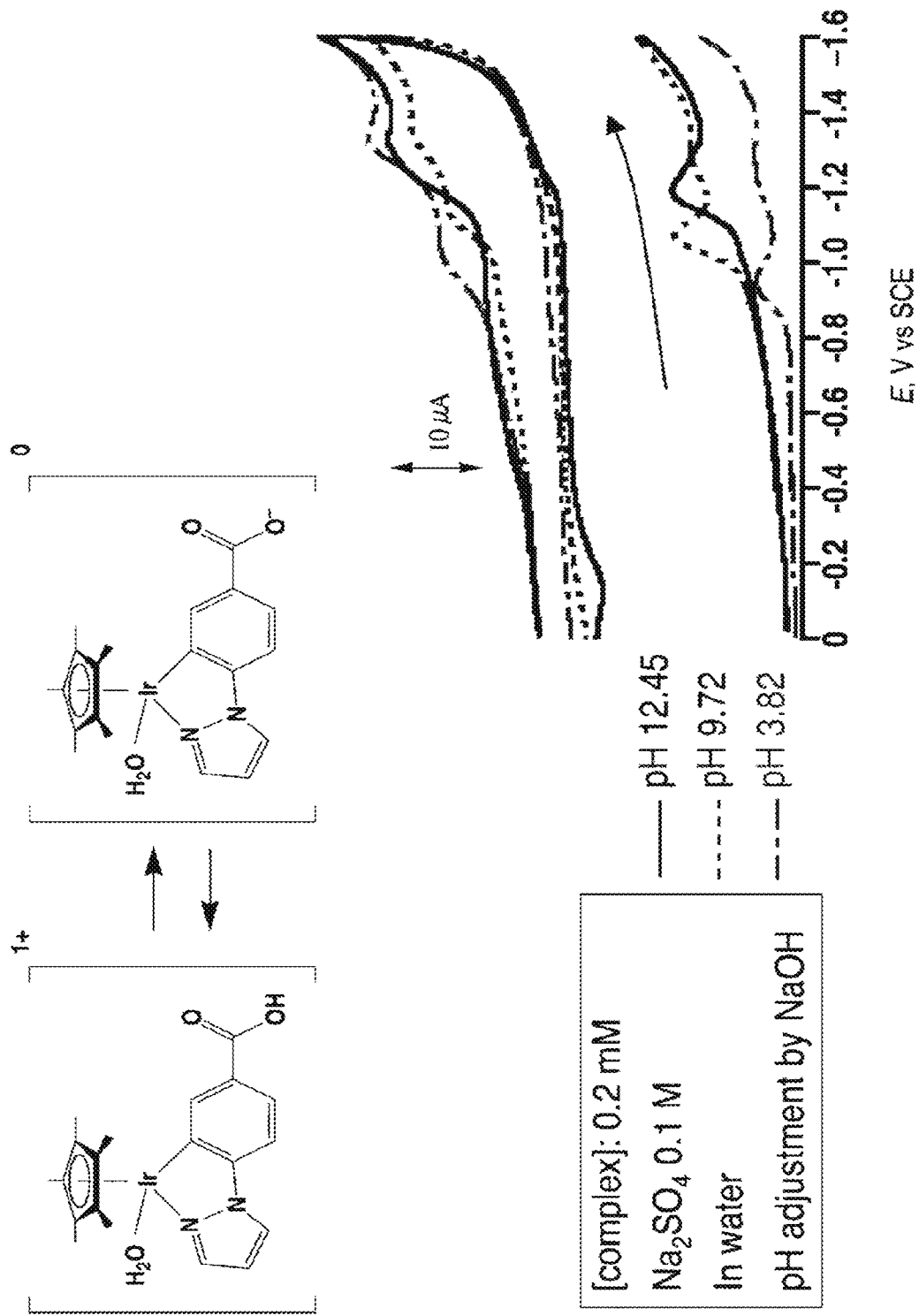
FIG. 22 shows a cyclic voltammogram of the iridium mononuclear aqua complex of Example 1.

An aqueous solution was prepared by adding 4-(1H-pyrazole-1-yl)benzoic acid (0.085 g, 0.454 mmol) to water (50 ml). The complex (108) sulfate, namely, the [Cp*Ir(H$_2$O)$_3$]$^{2+}$ sulfate, produced in Step 2 (0.20 g, 0.423 mmol) was added to this aqueous solution in an argon atmosphere, and the resultant mixture was heated to reflux for 12 hours in the dark. After the reflux, this solution was filtered through a membrane filter (manufactured by ADVANTEC, made of PTFE (polytetrafluoroethylene)). This filtrate was evaporated to remove moisture therefrom and then was vacuum-dried. Thus, desired iridium mononuclear aqua complex (13) sulfate, namely, [IrCp*(4-(1H-pyrazole-1-yl-κN$^{2-}$)benzoic acid-κC$^3$)(H$_2$O)]$^+$ sulfate, was obtained in the form of yellow powder (the yield calculated based on the sulfate of [Cp*Ir(H$_2$O)$_3$]$^{2\pm}$: 94%). The instrumental analysis values of the [IrCp*(4-(1H-pyrazole-1-yl-κN$^{2-}$)benzoic acid-κC$^3$)(H$_2$O)]$^+$ sulfate are shown below. FIG. 22 shows the measurement results obtained by CV (cyclic voltammetry). In order to measure the elementary analysis values, the iridium mononuclear aqua complex (13) was converted to the above-described zero-valent complex (14), which was isolated by crystallization. These elementary analysis values also are shown in FIG. 17.

¹H-NMR (DMSO-d₆, 298 K): δ (ppm) 1.75 (s, η⁵-C₅(CH₃)₅, 15H), 6.99 (d, d, J=2.2 Hz, J=2.7 Hz, 1H), 7.84 (d, d, J=8.4 Hz, J=2.2 Hz, 1H), 7.91 (d, J=8.4 Hz, 1H), 8.19 (d, J=1.5 Hz, 1H), 8.33 (d, J=2.2 Hz, 1H), 9.03 (d, J=2.7 Hz, 1H)

Elementary analysis values: $C_{20}H_{23}N_2O_3Ir$: C, 45.18%; H, 4.36%; N, 5.27%

Found: C, 44.90%; H, 4.30% N, 5.11%.

Figure 16A:
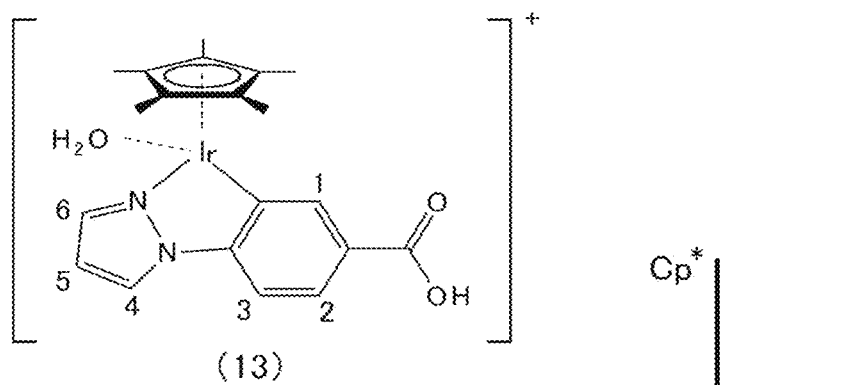
FIG. 16A is a $^1$H-NMR spectrum of the iridium mononuclear metal complex of Example 1.
Figure 16B:
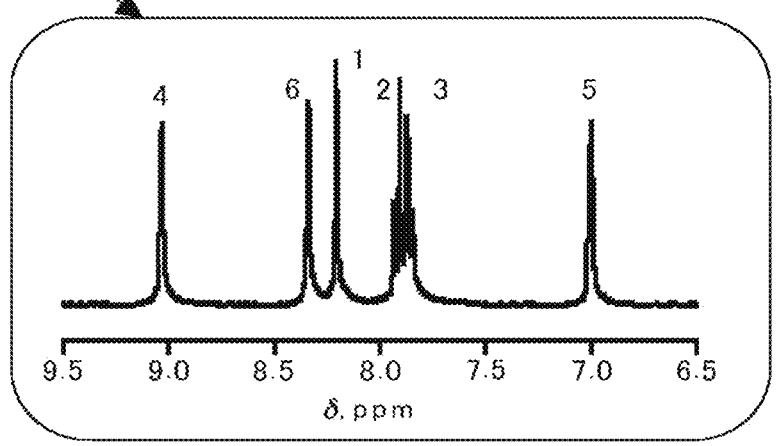
FIG. 16B is an enlarged view of a part of FIG. 16A.
Figure 16C:
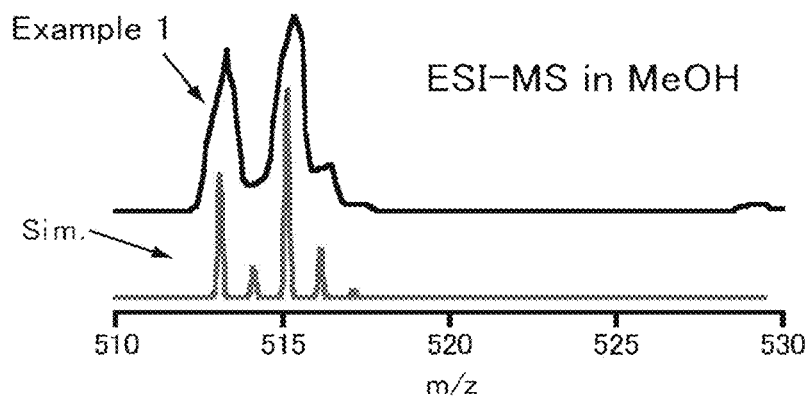
FIG. 16C shows a part of an ESI-MS spectrum of the iridium mononuclear aqua complex of Example 1.

FIGS. 16A and 16B show the ¹H-NMR spectrum of the iridium mononuclear aqua complex (13). FIG. 16A is an overall view of the ¹H-NMR spectrum, and FIG. 16B is an enlarged view of a part of the ¹H-NMR spectrum. FIG. 16C shows an ESI-MS spectrum of the iridium mononuclear aqua complex (13) in methanol. In this ESI-MS spectrum, an iridium complex [IrCp*(4-(1H-pyrazole-1-yl-κN²⁻)benzoic acid-κC³)]⁺, which corresponds to the iridium mononuclear aqua complex (13) from which the water molecule as a ligand (aqua ligand) has been dissociated, was observed as the parent ion peak with the highest m/z (m/z=515). FIG. 17 shows an ORTEP diagram of the crystal structure of the iridium mononuclear aqua complex (14), as well as the analytical values of the iridium mononuclear aqua complex (14).

Figure 18A:
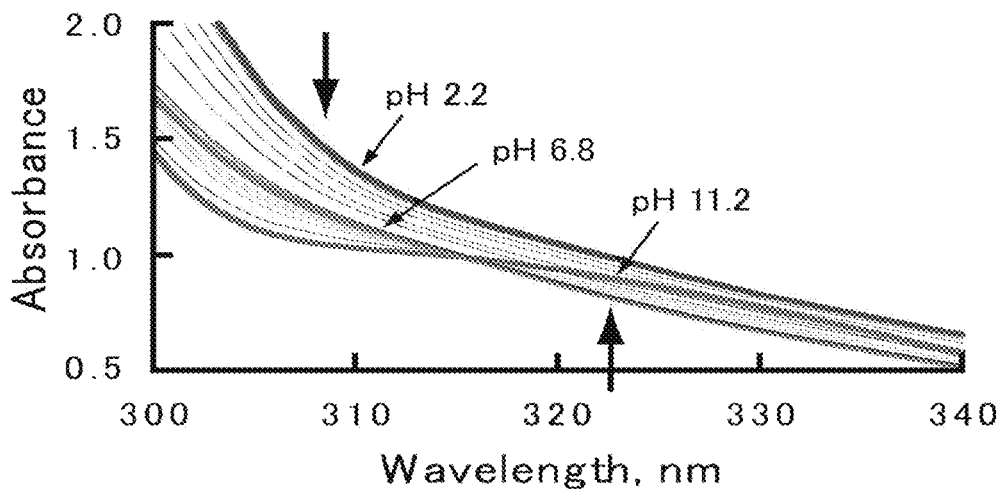
FIG. 18A is a graph showing the change in UV-Vis. spectrum when the pH of an aqueous solution of the iridium mononuclear aqua complex of Example 1 was adjusted to 2.2, 6.8, and 11.2 by adding dilute sulfuric acid.
Figure 18B:
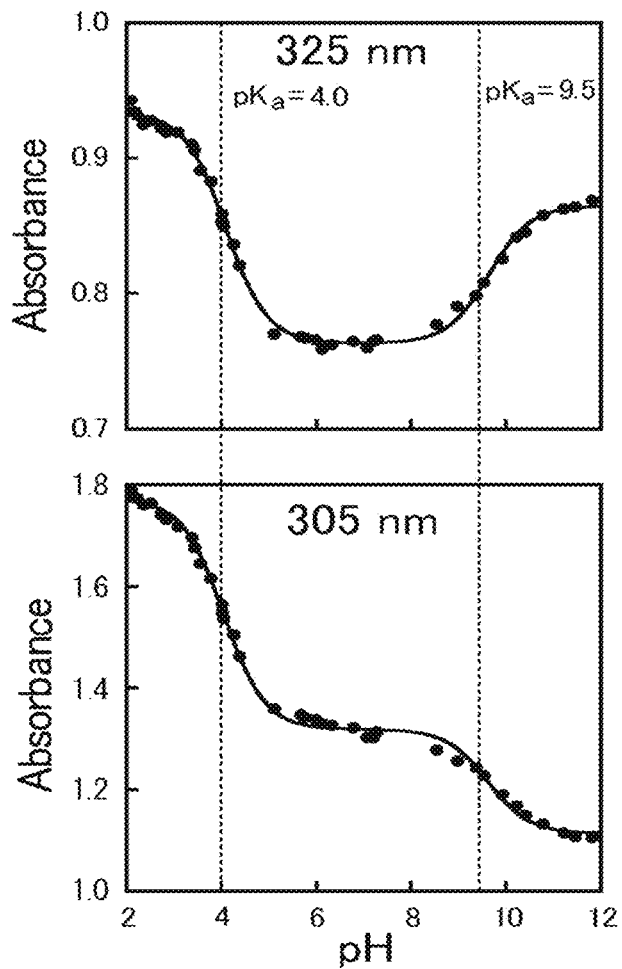
FIG. 18B is a graph showing the change in absorbance at 305 nm and 325 nm by the change in pH.
Figure 19:
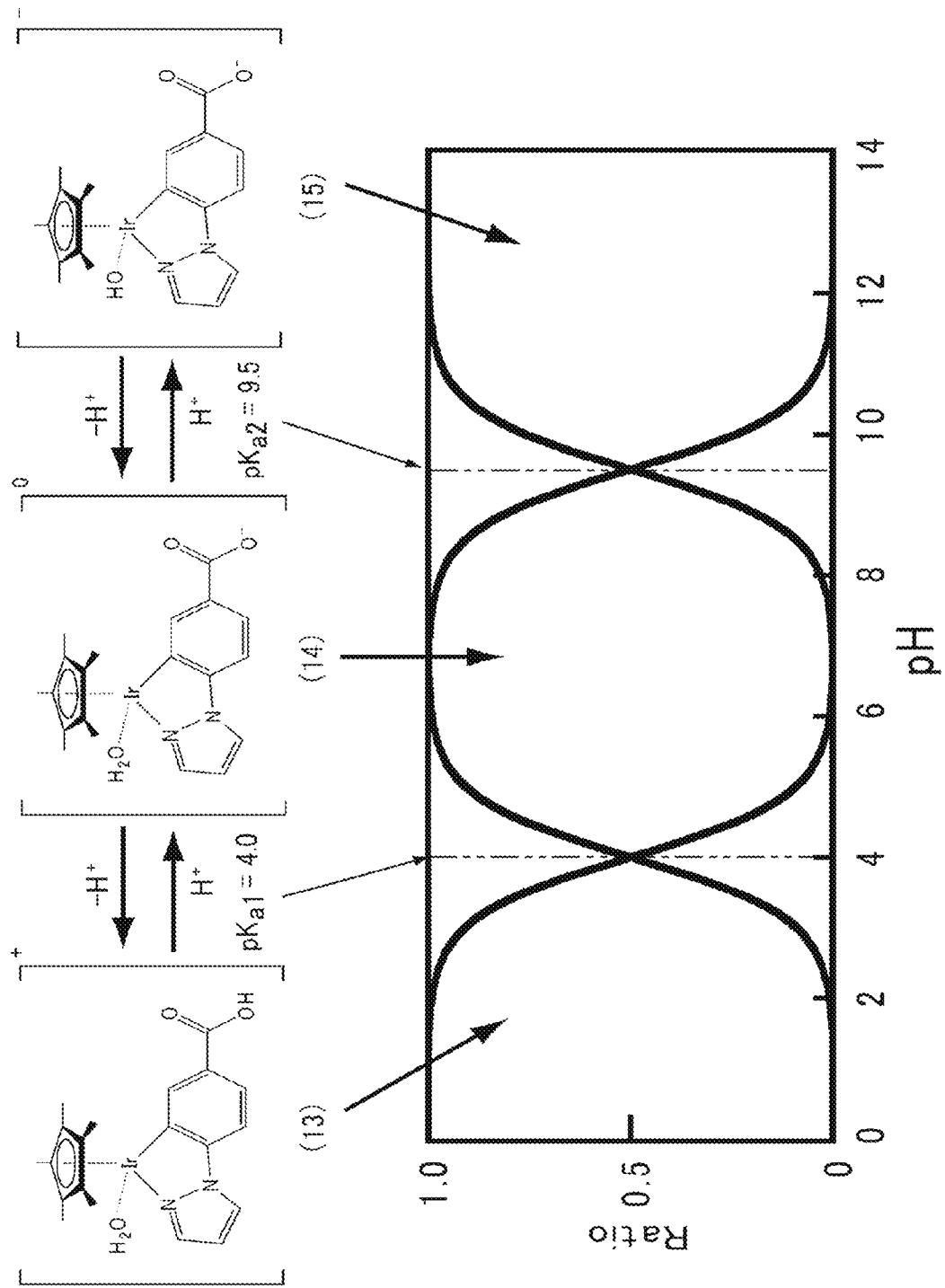
FIG. 19 shows the abundance ratio of the iridium mononuclear aqua complex of Example 1 in the complex aqueous solution.

FIG. 18A shows the results of measuring the change in ultraviolet-visible absorption spectrum when the pH of the iridium mononuclear aqua complex (13) aqueous solution (0.12 mM, 2 ml) was adjusted to 2.2, 6.8, and 11.2. In FIG. 18A, the horizontal axis indicates the wavelength (nm), and the vertical axis indicates the absorbance. The pH was adjusted by adding dilute sulfuric acid. This measurement was carried out in deaerated water at 298 K using a 1-cm optical path length. FIG. 18B shows the change in absorbance accompanying the change in pH at the wavelengths (305 nm and 325 nm) indicated with arrows in FIG. 18A. In FIG. 18B, the horizontal axis indicates the pH, and the vertical axis indicates the absorbance. The change in pH was caused by adding sodium hydroxide. As can be seen from FIG. 18B, the iridium mononuclear aqua complex (13) exhibited two acid dissociation constants pKa (pKa=4.0, 9.5). From this result, it is presumed that the iridium mononuclear aqua complex (13) was present in any of the following states depending on the pH of the complex aqueous solution, as shown in FIG. 19: the state where any of the complexes of the formulae (13) to (15) was present; the state where the complexes of the formulae (13) and (14) were present together at a predetermined ratio; and the state where the complexes of the formulae (14) and (15) were present together at a predetermined ratio. More specifically, it is presumed that the abundance ratio of the complex (13) is as follows depending on the form of carbon dioxide: the abundance ratio of the complex (13) is large when the abundance ratio of $CO_2$ is large (pH: about 6 or lower); the abundance ratio of the complex (14) is large when the abundance ratio of $HCO_3^-$ is large (pH: from about 6 to about 10); and the abundance ratio of the complex (15) is large when the abundance ratio of $CO_3^{2-}$ is large (pH: about 10 or higher).

Example 2

Production of Iridium Mononuclear Aqua Complex (16)

An iridium mononuclear aqua complex (16) was produced (synthesized) according to Scheme 2. This will be described specifically below.

Step 1: Production of 4-(1H-pyrazole-1-yl)benzenesulfonic acid

A solution was prepared by adding 1-phenylpyrazole (1.3 ml, 9.8 mmol) to concentrated sulfuric acid (2 ml). To this solution, fuming sulfuric acid (5 ml, 30% SO3) was added gradually over at least 5 minutes at 0° C. The resultant mixture was heated to 35° C., and this temperature was kept for 1 hour. This mixture then was cooled to 0° C. by pouring it over crushed ice, thereby causing sulfate to precipitate. This sulfate was collected by filtration and then vacuum-dried. Thus, a desired compound, 4-(1H-pyrazole-1-yl)benzenesulfonic acid, was obtained in the form of a white solid (the yield calculated based on 1-phenylpyrazole: 37%). The instrumental analysis values of 4-(1H-pyrazole-1-yl)benzenesulfonic acid are shown below.

¹H-NMR (DMSO-d₆, 298 K): δ (ppm) 6.55 (d, d, J=1.5 Hz, J=2.6 Hz, 1H), 7.68 (d, J=2.4 Hz, 2H), 7.75 (d, J=1.5 Hz, 1H), 7.80 (d, J=2.4 Hz, 2H), 8.52 (d, J=2.6 Hz, 1H).

Step 2: Production of [IrCp*(4-(1H-pyrazole-1-yl-κN²)benzenesulfonic acid-κC³)(H₂O)]⁺ (an iridium mononuclear aqua complex (16)) sulfate An aqueous solution was prepared by adding [Cp*Ir(H₂O)₃]²⁺ sulfate (0.20 g, 0.45 mmol) to water (30 ml). To this aqueous solution, the 4-(1H-pyrazole-1-yl)benzenesulfonic acid (0.1 g, 0.45 mmol) produced in Step 1 was added in an argon atmosphere, and the resultant mixture was heated to reflux for 16 hours in the dark. After the reflux, the precipitates were collected by filtration and dried under reduced pressure. Thus, desired iridium mononuclear aqua complex (16) sulfate, namely, [IrCp*(4-(1H-pyrazole-1-yl-κN²⁻)benzenesulfonic acid-κC³)(H₂O)]⁺ sulfate, was obtained in the form of yellow powder (the yield calculated based on the sulfate of [Cp*Ir(H₂O)₃]²⁺: 26%). The instrumental analysis values of the [IrCp*(4-(1H-pyrazole-1-yl-κN²⁻)benzenesulfonic acid-κC³)(H₂O)]⁺ sulfate are shown below.

¹H-NMR (DMSO-d₆, 298 K): δ (ppm) 1.75 (s, η⁵-C₅(CH₃)₅, 15H), 6.95 (d, d, J=2.2 Hz, J=2.9 Hz, 1H), 7.59 (d, d, J=8.1 Hz, J=1.5 Hz, 1H), 7.76 (d, J=8.1 Hz, 1H), 7.89 (d, J=1.5 Hz, 1H), 8.26 (d, J=2.2 Hz, 1H), 8.94 (d, J=2.9 Hz, 1H)

Elementary analysis: [IrCp*(4-(1H-pyrazol-1-yl-κN²⁻)benzensulfonic acid-κC³)(H₂O)]⁺ sulfate: $C_{19}H_{22}N_2O_4SIr$: Theoretical values: C, 40.19%; H, 4.08% N, 4.93%. Observed values: C, 39.76%; H, 4.10% N, 4.95%.

Figure 20A:
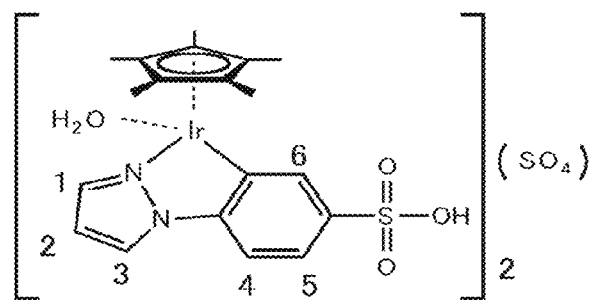
FIG. 20A is a $^1$H-NMR spectrum of the iridium mononuclear metal complex of Example 2.
Figure 20A:
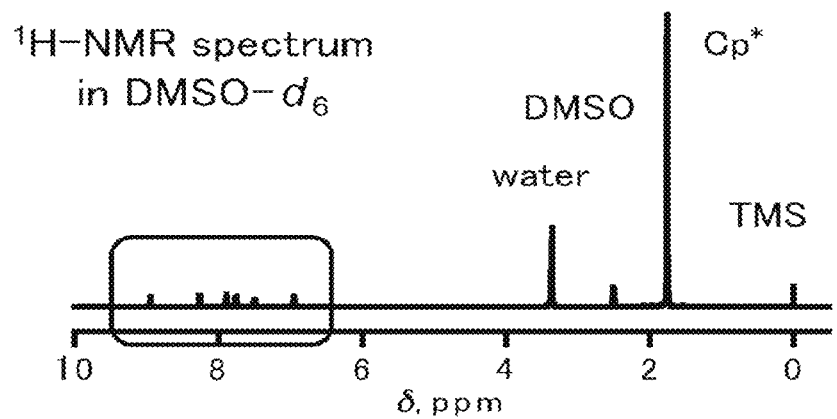
Figure 20B:
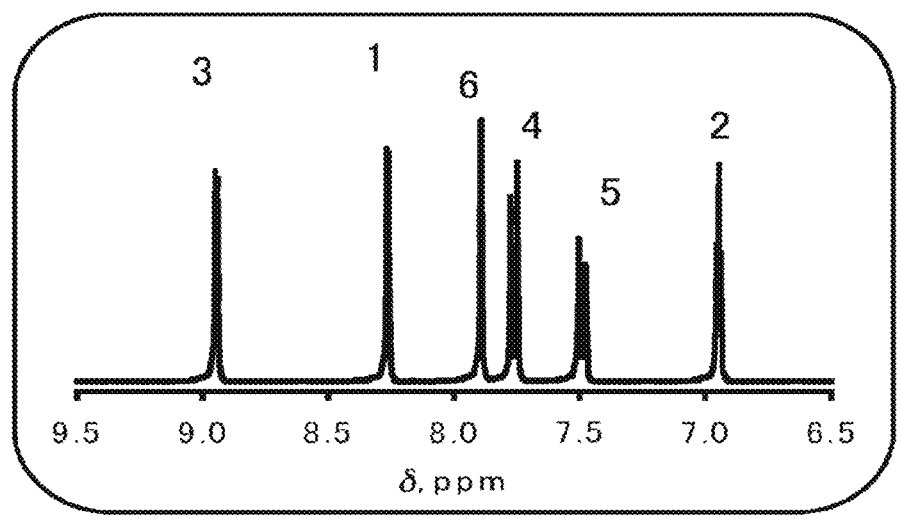
FIG. 20B is an enlarged view of a part of FIG. 20A.

FIGS. 20A and 20B show the ¹H-NMR spectrum of the iridium mononuclear aqua complex (16). FIG. 20A is an overall view of the ¹H-NMR spectrum, and FIG. 20B is an enlarged view of a part of the ¹H-NMR spectrum.

Next, the performance of the iridium mononuclear aqua complex (13) sulfate and the iridium mononuclear aqua complex (13) sulfate was evaluated in the following manner.

Examples 3 to 4

Formic Acid Production and Carbon Dioxide Fixation by Carbon Dioxide Fixation Catalyst (1) Formic Acid Production and Carbon Dioxide Fixation by Iridium Mononuclear Aqua Complex (13) Sulfate (Example 3)

Figure 1B:
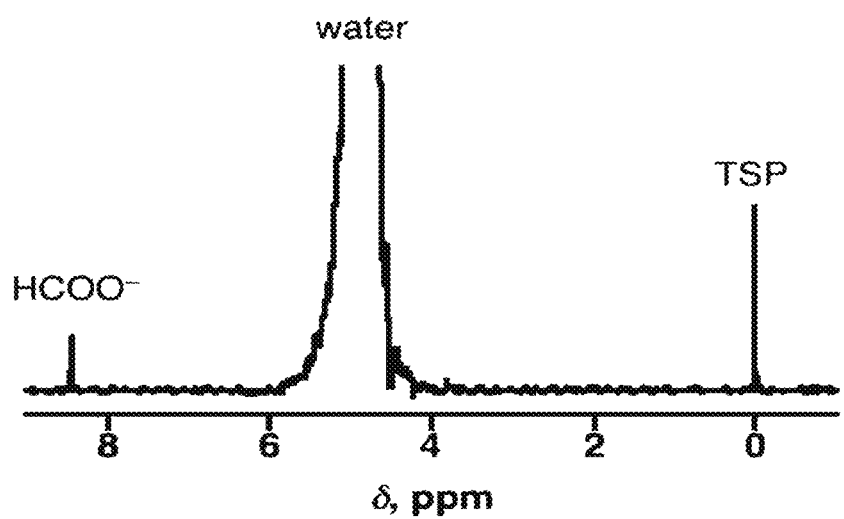
FIG. 1B is a $^1$H-NMR spectrum showing an example of the measurement result of quantifying the generated formic acid.

The iridium mononuclear aqua complex (13) sulfate produced in Example 1 was dissolved in a potassium carbonate aqueous solution (0.1 mM). Carbon dioxide under ordinary pressure (1 atm) was blown into this complex aqueous solution (0.26 mM) for 1 hour at room temperature (30° C. (303 K)) under deoxygenated conditions. Thus, the complex aqueous solution was saturated with carbon dioxide. The pH of the complex aqueous solution at this time was 7.5. In this state, carbon dioxide with ordinary pressure (1 atm) and hydrogen (H₂) with ordinary pressure (1 atm) were blown into the complex aqueous solution at the same time at a flow rate of 50 cc/min to cause bubbling. Thus, a carbon dioxide fixation reaction (formic acid production reaction) was started. Aliquot parts of this reaction solution were collected at regular time intervals, and $^1$H-NMR measurement of the generated formic acid was performed, as shown in FIG. 1B. The $^1$H-NMR measurement was performed in water ($H_2O$) using a $D_2O$-containing capillary as an internal lock. For the quantification of the generated formic acid, TSP (3-(trimethylsilyl)-3,3,2,2-propionic acid-$d_4$ (10 mM)) was used as an internal standard. The results thereof are shown in the graph of FIG. 1A. In FIG. 1A, the horizontal axis indicates the reaction time (h), and the vertical axis indicates the formate ion concentration (mM). As can be seen from FIG. 1A, the amount of the generated formic acid increased in proportion to the reaction time. The catalyst turn-over frequency (TOF, the number of catalyst turnovers per hour) was 6.78 $h^{-1}$, which is the world highest TOF in a carbon dioxide fixation reaction in water at room temperature known at the time this application was filed. Also, it was found that the catalytic activity is maintained even if the turn-over number (TON, the number of moles of formic acid generated per mole of catalyst) exceeds 100. That is, the iridium mononuclear aqua complex (13) sulfate produced in Example 1 had high catalytic activity and could be used as a carbon dioxide fixation catalyst that allows efficient production of formic acid by reacting carbon dioxide with hydrogen ($H_2$) to fix the carbon dioxide in an aqueous solution at ordinary temperature and ordinary pressure.

(2) Formic Acid Production and Carbon Dioxide Fixation by Iridium Mononuclear Aqua Complex (16) Sulfate (Example 4)

Figure 2:
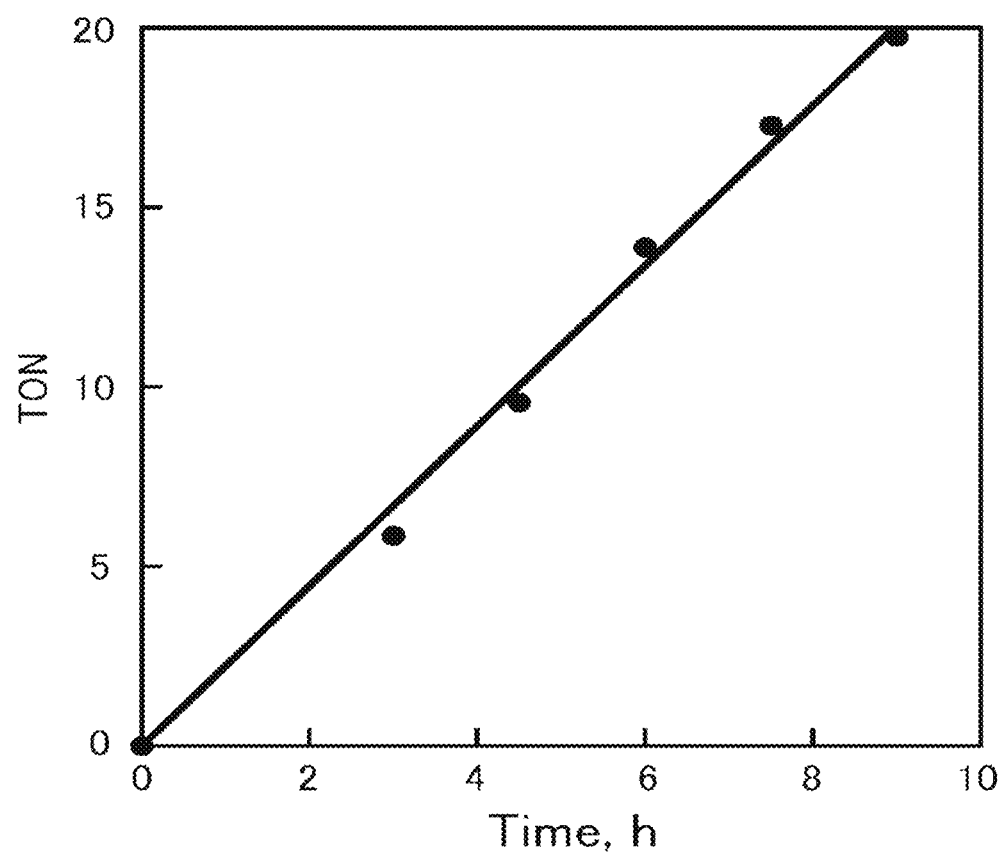
FIG. 2 is a graph showing, in Example 4, the relationship between the passage of reaction time in an aqueous solution of the iridium mononuclear aqua complex of Example 2 and TON.

The iridium mononuclear aqua complex (16) sulfate produced in Example 2 was dissolved in a potassium carbonate aqueous solution (0.1 mM). Carbon dioxide under ordinary pressure (1 atm) was blown into this complex aqueous solution (0.32 mM) for 1 hour at room temperature (30° C. (303 K)) under deoxygenated conditions. Thus, the complex aqueous solution was saturated with carbon dioxide. The pH of the complex aqueous solution at this time was 7.4. In this state, carbon dioxide with ordinary pressure (1 atm) and hydrogen ($H_2$) with ordinary pressure (1 atm) were blown into the complex aqueous solution at the same time at a flow rate of 50 cc/min to cause bubbling. Thus, a carbon dioxide fixation reaction (formic acid production reaction) was started. Aliquot parts of this reaction solution were collected at regular time intervals, and $^1$H-NMR measurement of the generated formic acid was performed in the same manner as in (1) of Example 1. The results thereof are shown in the graph of FIG. 2. In FIG. 2, the horizontal axis indicates the reaction time (h), and the vertical axis indicates TON. As can be seen from FIG. 2, TON increased in proportion to the reaction time. In other words, the amount of the generated formic acid increased in proportion to the reaction time. The catalyst turn-over frequency (TOF) was 2.2 $h^{-1}$. In the following examples, $^1$H-NMR measurement of the generated formic acid was carried out in the same manner as in the above.

Example 5 pH Dependence 1 of Formic Acid Production and Carbon Dioxide Fixation (pH: 8.8 or Higher)

Figure 3A:
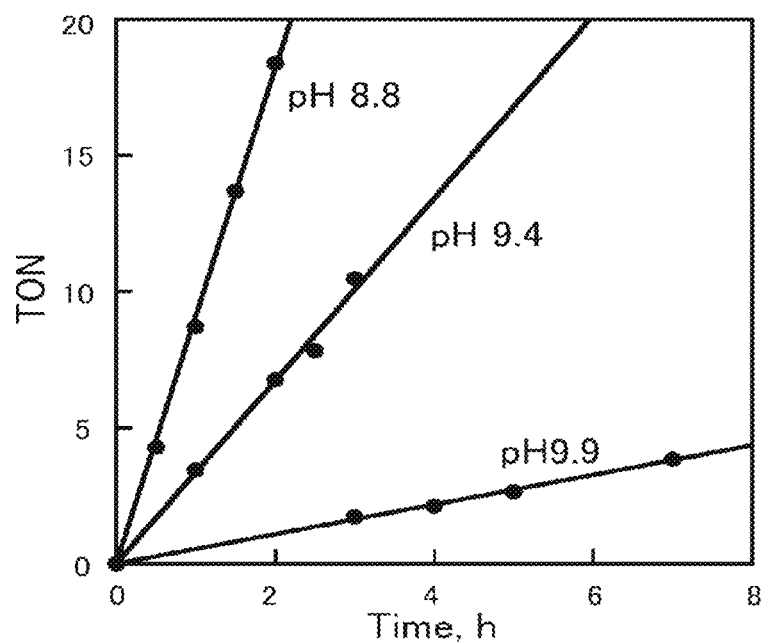
FIG. 3A is a graph showing the pH dependence of TON in an aqueous solution of the iridium mononuclear aqua complex of Example 1.
Figure 3B:
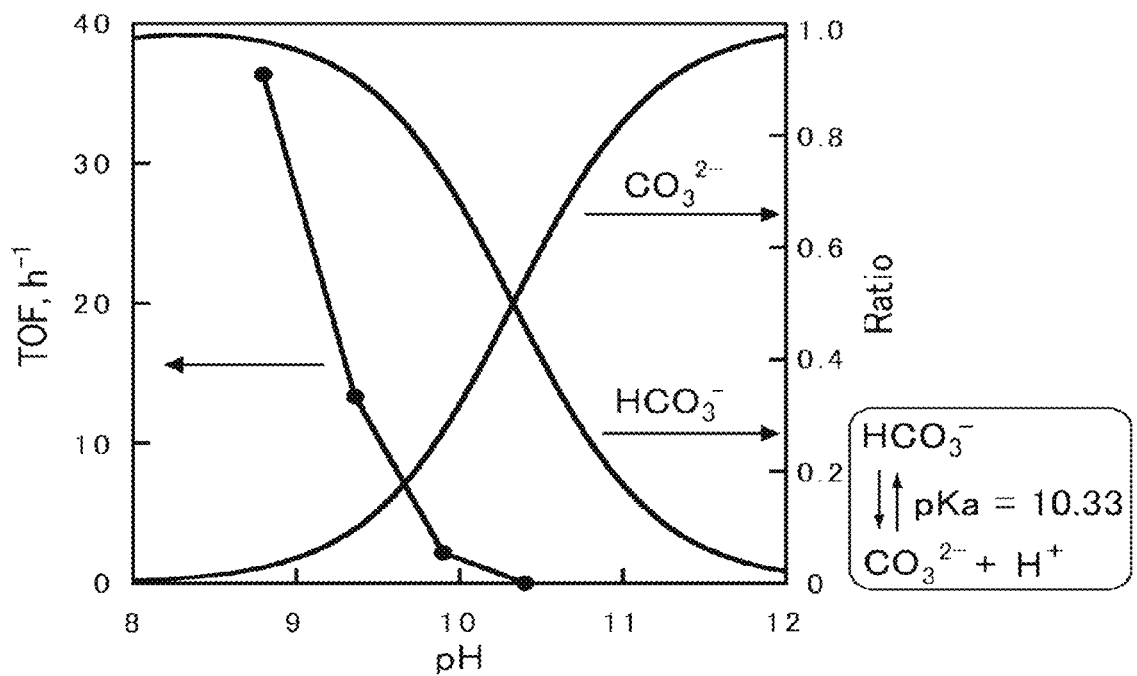
FIG. 3B is a graph showing the relationship of the pH of the aqueous solution of the iridium mononuclear aqua complex of Example 1 with TOF, carbonate ion, and bicarbonate ion.

The iridium mononuclear aqua complex (13) sulfate produced in Example 1 was dissolved in a potassium bicarbonate/potassium carbonate aqueous solution (2M). In order to examine the relationship between the amount of the generated formic acid and the pH of the complex aqueous solution, the pH of this complex aqueous solution was adjusted to 8.8, 9.4, or 9.9. This complex aqueous solution (0.18 mM) was allowed to stand in this state at 60° C. (333 K) in a hydrogen ($H_2$) atmosphere, thus causing a carbon dioxide fixation reaction (formic acid production reaction) to start. The results thereof are shown in FIG. 3. FIG. 3A is a graph showing the relationship between the elapsed time from the start of the reaction (the reaction time) and TON, when the pH of the complex aqueous solution was set to 8.8, 9.4, and 9.9. In FIG. 3A, the horizontal axis indicates the reaction time (h), and the vertical axis indicates TON. The pH was adjusted by adjusting the amount-of-substance ratio between the potassium bicarbonate and the potassium carbonate. For example, the pH of a 2M potassium bicarbonate aqueous solution (containing potassium bicarbonate only) is 8.8, and the pH of a 2M potassium carbonate aqueous solution (containing only potassium carbonate) is 10.4. The concentration of the iridium mononuclear aqua complex (13) sulfate was low relative to the total concentration of the potassium bicarbonate and the potassium carbonate as described above, so that it did not affect the pH of the aqueous solution. As can be seen from FIG. 3A, the TON increased in proportion to the reaction time at any of the pHs. In other words, the amount of the generated formic acid increased in proportion to the reaction time. FIG. 3B is a graph showing the relationship between the pH of the complex aqueous solution and the TOF. The graph of FIG. 3B also shows the ratio between carbonate ions ($CO_3^{2-}$) and bicarbonate ions ($HCO_3^-$) in the complex reaction solution (the axis on the right in this graph). As can be seen from FIG. 3B, the TOF changed depending on the change in pH. Specifically, the catalytic activity of the iridium mononuclear aqua complex (13) sulfate produced in Example 1 was dependent on the pH, and it became lower as the pH of the complex aqueous solution became higher. On the other hand, the relationship between the carbonate ion and the bicarbonate ion was such that, as the pH became higher, the abundance ratio of the carbonate ion became greater while the abundance ratio of the bicarbonate ion became smaller. From these results, it is presumed that the iridium mononuclear aqua complex (13) sulfate produced in Example 1 uses bicarbonate ion ($HCO_3^-$) as the substrate in the formic acid generation. It is also presumed that formic acid is generated through hydrogenation of the bicarbonate ion ($HCO_3^-$).

Figure 4:
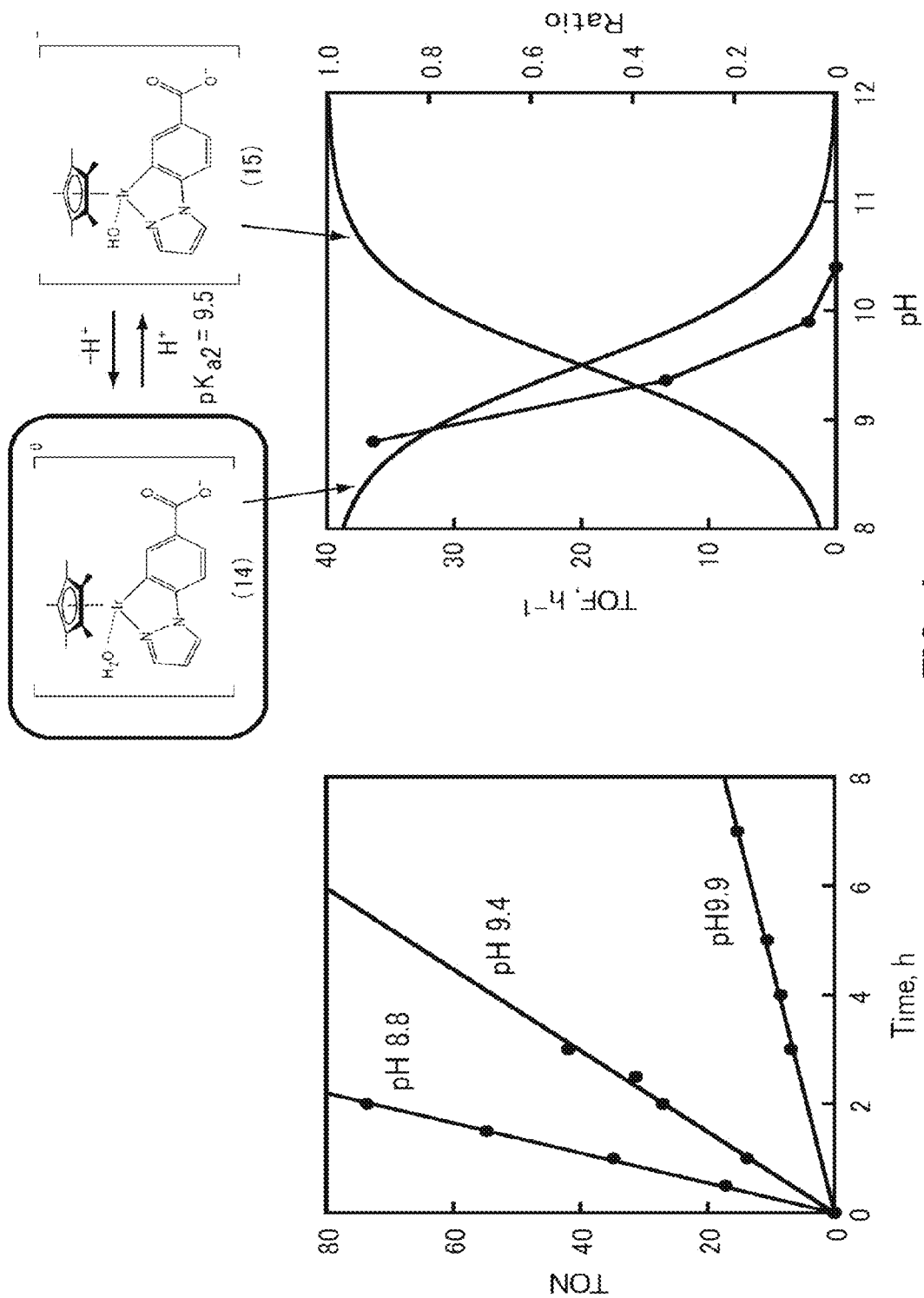
FIG. 4 shows the relationship between the pH dependence of TOF and the abundance ratio of each of the iridium mononuclear aqua complexes represented by the formulae (14) and (15) in the aqueous solution of the iridium mononuclear aqua complex of Example 1.

The right graph in FIG. 4 shows the relationship between the pH of the complex aqueous solution and the TOF shown in the graph of FIG. 3B, as well as the abundance ratio (Ratio) of the iridium mononuclear aqua complex (13) produced in Example 1 in accordance with the pH. The left graph in FIG. 4 is the same as the graph of FIG. 3A. As can be seen from FIGS. 3 and 4, the correlation was observed between the catalytic activity (TOF) for the carbon dioxide fixation (formic acid production) of this complex and the abundance ratio (Ratio) of each of the iridium mononuclear aqua complexes represented by the formulae (14) and (15).

Figure 5A:
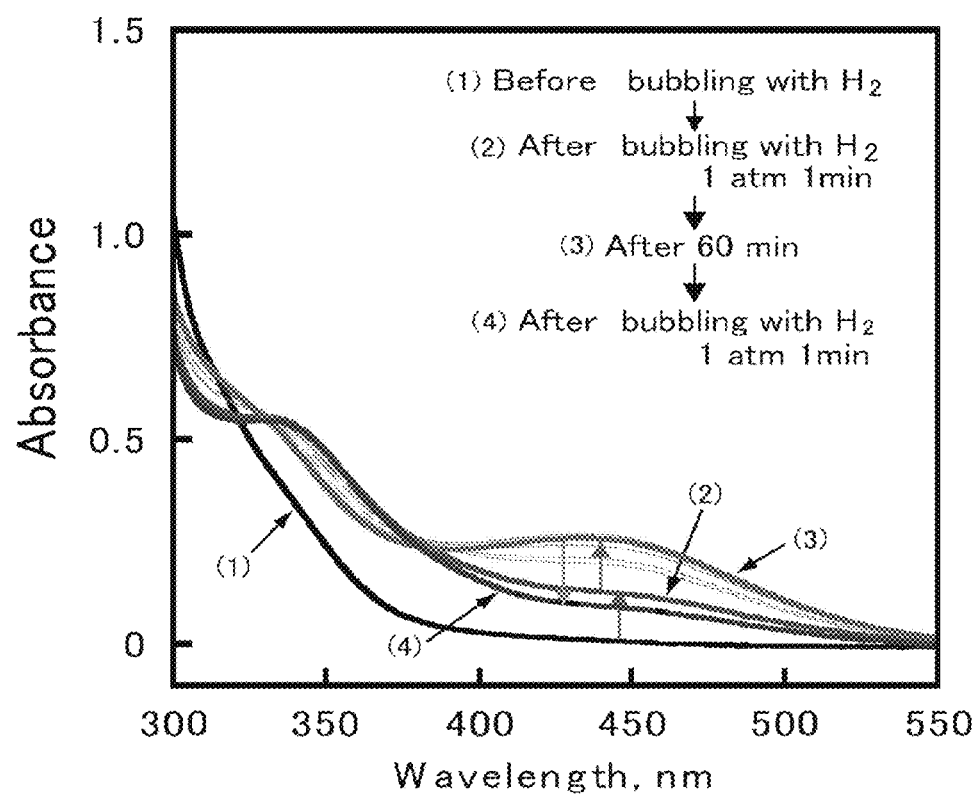
FIG. 5A is a graph showing the change in absorption spectrum of an aqueous solution of the iridium mononuclear aqua complex of Example 1 before and after blowing of hydrogen ($H_2$) into the aqueous solution.
Figure 6:
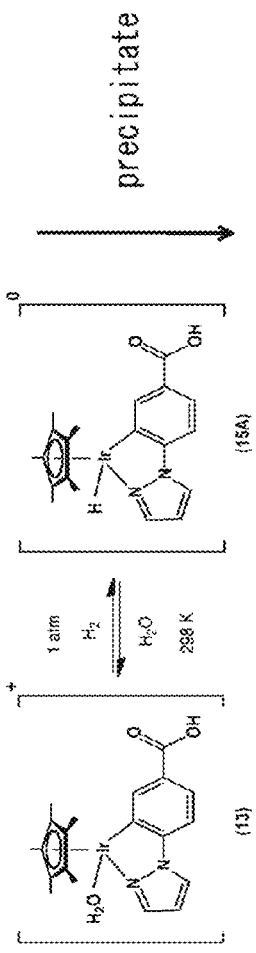
FIG. 6 shows charts illustrating an example of the detection and measurement of a hydrido complex in the iridium mononuclear aqua complex of Example 1 by $^1$H-NMR.
Figure 6:
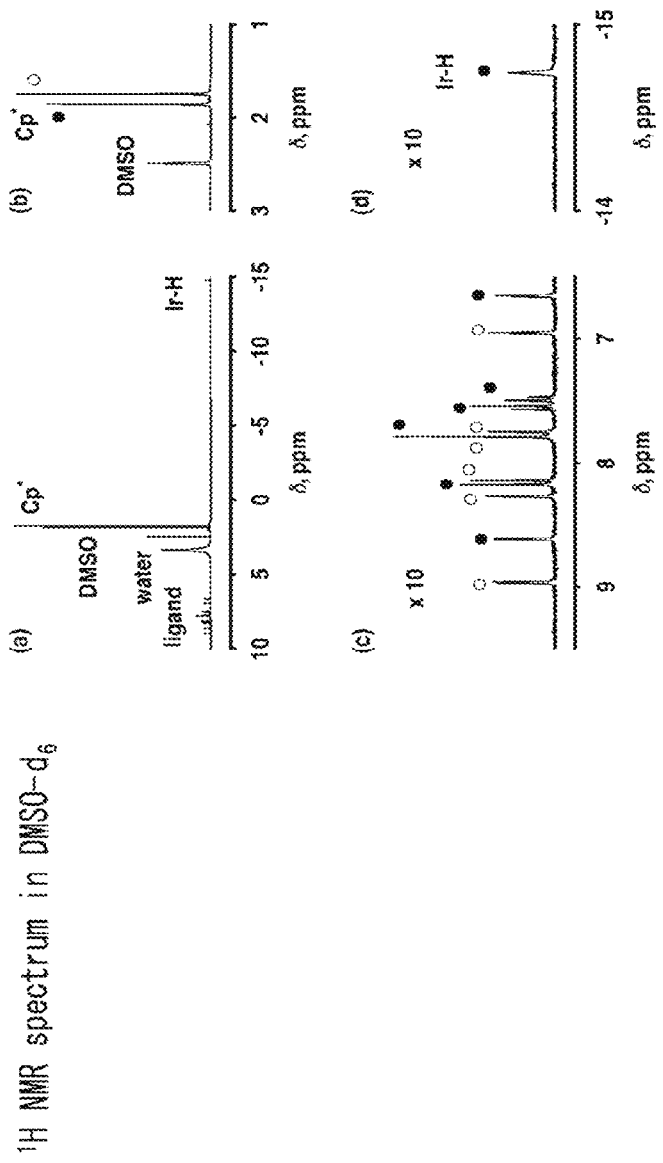

FIG. 5A shows the change in UV-Vis. spectrum by the blowing of hydrogen ($H_2$) into an aqueous solution of the iridium mononuclear aqua complex (13) produced in Example 1. In FIG. 5A, the horizontal axis indicates the wavelength (nm), and the vertical axis indicates the absorbance. The measurement shown in FIG. 5A was carried out by setting the conditions as follows. Specifically, first, the iridium mononuclear aqua complex (13) sulfate produced in Example 1 was dissolved in a potassium carbonate aqueous solution (2M). Then, hydrogen ($H_2$) under ordinary pressure (1 atm) was blown into this complex aqueous solution (0.15 mM, pH 8.8) for 1 minute at room temperature (25° C. (298 K)) under deoxygenated conditions ((2) in FIG. 5A). The complex aqueous solution then was left to stand for 60 minutes ((3) in FIG. 5A). Subsequently, hydrogen under ordinary pressure (1 atm) was blown into the complex aqueous solution again for 1 minute ((4) in FIG. 5A). The change in UV-Vis. spectrum from the state before blowing the hydrogen ($H_2$) ((1) in FIG. 5A) to each of the states (2) to (4) was measured. This measurement was carried out in deaerated water at 298 K using a 1-cm optical path length. As can be seen from FIG. 5A, the UV-Vis. spectrum changed before and after the blowing of hydrogen into the complex aqueous solution. From this result, it is presumed that the iridium mononuclear aqua complex produced in Example 1 forms a hydrido complex (15B) by reacting with hydrogen ($H_2$) brown into the complex aqueous solution. The hydrido complex (15B) can be detected and measured by the $^1$H-NMR measurement shown in FIG. 6, for example.

Figure 5B:
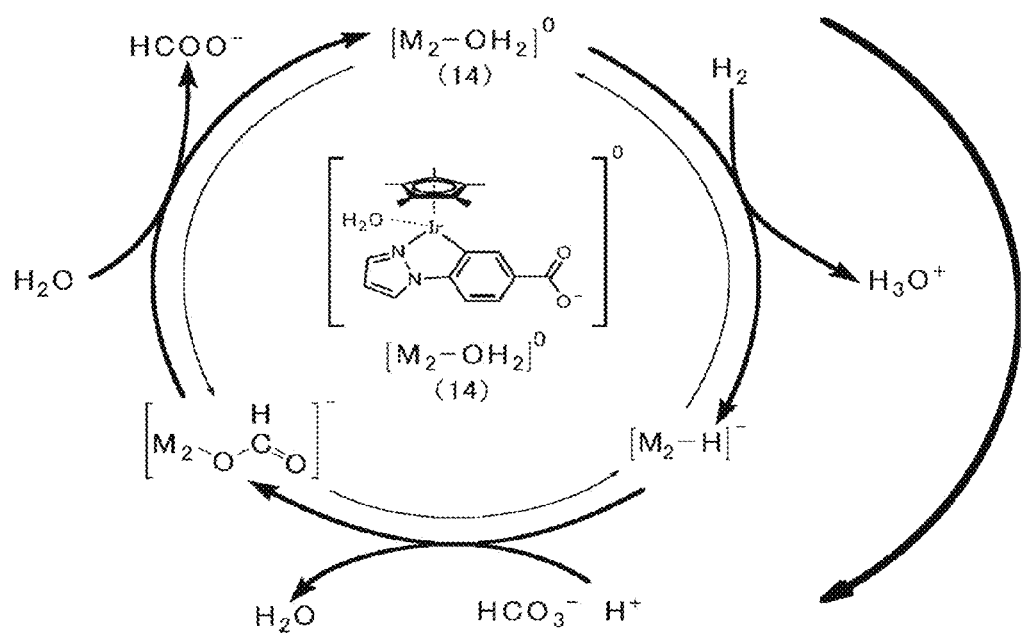
FIG. 5B is a scheme showing an example of a presumable reaction mechanism of carbon dioxide fixation in the iridium mononuclear aqua complex of Example 1.

Based on the above presumption, a presumable reaction mechanism of the carbon dioxide fixation by the iridium mononuclear aqua complex produced in Example 1 is shown in the scheme of FIG. 5B. In FIG. 5B, "$M_2$" means a moiety in the structure of the iridium mononuclear aqua complex represented by the formula (14) excluding the ligand (water molecule) corresponding to the ligand L in the formula (1). As can be seen from FIG. 5B, hydrogen ($H_2$) is caused to be present in the complex aqueous solution by allowing the complex aqueous solution to stand in a hydrogen ($H_2$) atmosphere, and the iridium mononuclear aqua complex (14) present in this complex aqueous solution (pH 8.8) thus turns to a hydrido complex. This hydrido complex is hydrogenated with a bicarbonate ion as a substrate and thus turns to a formic acid complex. When this formic acid complex turns to the complex of the formula (14) again (the ligand L turns to $H_2O$), formic acid is produced (generated). It is presumed that, through these processes, the iridium mononuclear aqua complex produced in Example 1 fixes carbon dioxide and produces (generates) formic acid. It is to be noted, however, that this reaction mechanism merely is an example of a presumable mechanism, and does not limit the present invention by any means.

Example 6 pH Dependence 2 of Formic Acid Production and Carbon Dioxide Fixation (pH: 7.8 or Lower)

Figure 7:
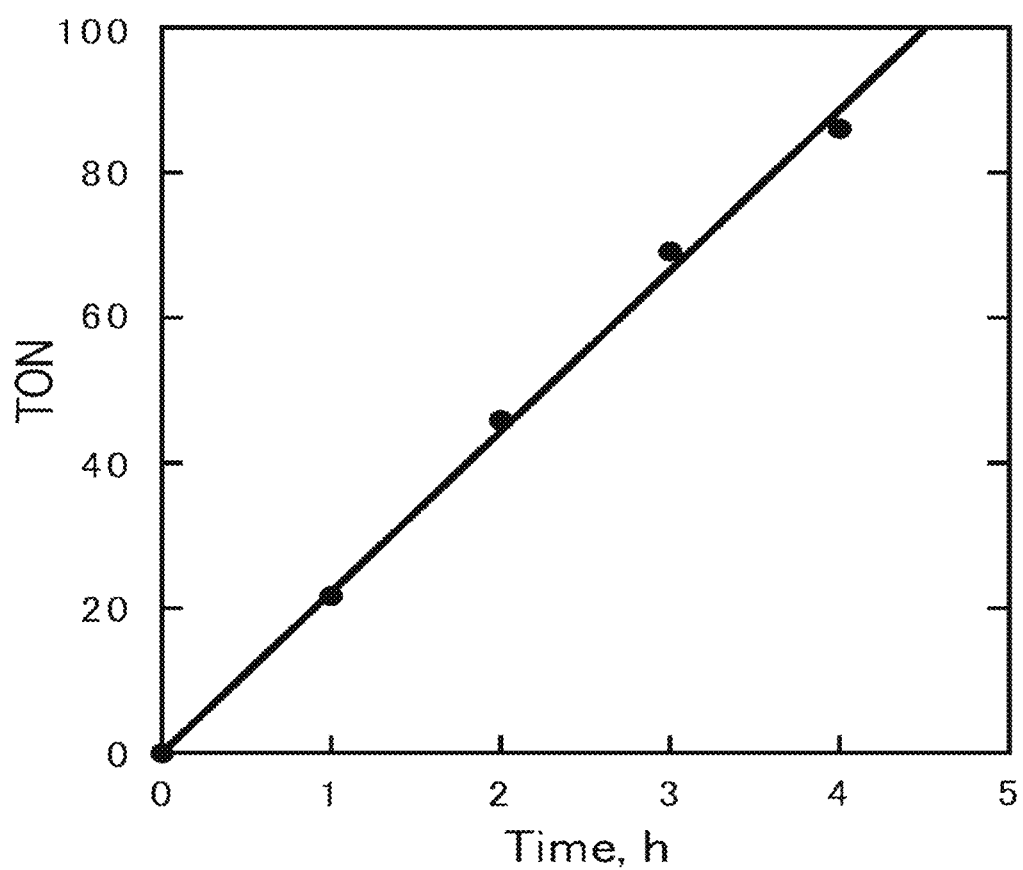
FIG. 7 is a graph showing, in Example 6, the pH dependence of TON in an aqueous solution of the iridium mononuclear aqua complex of Example 1.

The iridium mononuclear aqua complex (13) sulfate produced in Example 1 was dissolved in a potassium carbonate aqueous solution (0.1 mM). Carbon dioxide under ordinary pressure (1 atm) was blown into this complex aqueous solution (0.18 mM) for 1 hour at room temperature (60° C. (333 K)) under deoxygenated conditions. Thus, the complex aqueous solution was saturated with carbon dioxide. The pH of the complex aqueous solution at this time was 7.8. In this state, carbon dioxide with ordinary pressure (1 atm) and hydrogen ($H_2$) with ordinary pressure (1 atm) were blown into the complex aqueous solution at the same time at a flow rate of 50 cc/min to cause bubbling. Thus, a carbon dioxide fixation reaction (formic acid production reaction) was started. Aliquot parts of this reaction solution were collected at time intervals of 1 hour, and $^1$H-NMR measurement of the generated formic acid was performed. The results thereof are shown in the graph of FIG. 7. In FIG. 7, the horizontal axis indicates the reaction time (h), and the vertical axis indicates TON. As can be seen from FIG. 7, the TON increased in proportion to the reaction time. In other words, the amount of the generated formic acid increased in proportion to the reaction time. The TOF was 22.1 h$^{-1}$. In the case where the iridium mononuclear aqua complex (13) sulfate produced in Example 1 was dissolved in water instead of in the potassium carbonate aqueous solution (0.1 mM), this complex solution had a pH of 6.0 when it was saturated with carbon dioxide. Even when carbon dioxide and hydrogen were blown into the complex aqueous solution in this state at the same time to cause bubbling in the same manner as in the above, the generation of formic acid was not observed. It is presumed that, because of the influence of the decomposition of the formic acid to be described below, the formic acid generation was not observed at the low pH as described above. It is to be noted, however, that this presumption does not limit or restrict the present invention by any means.

Example 7

Figure 8A:
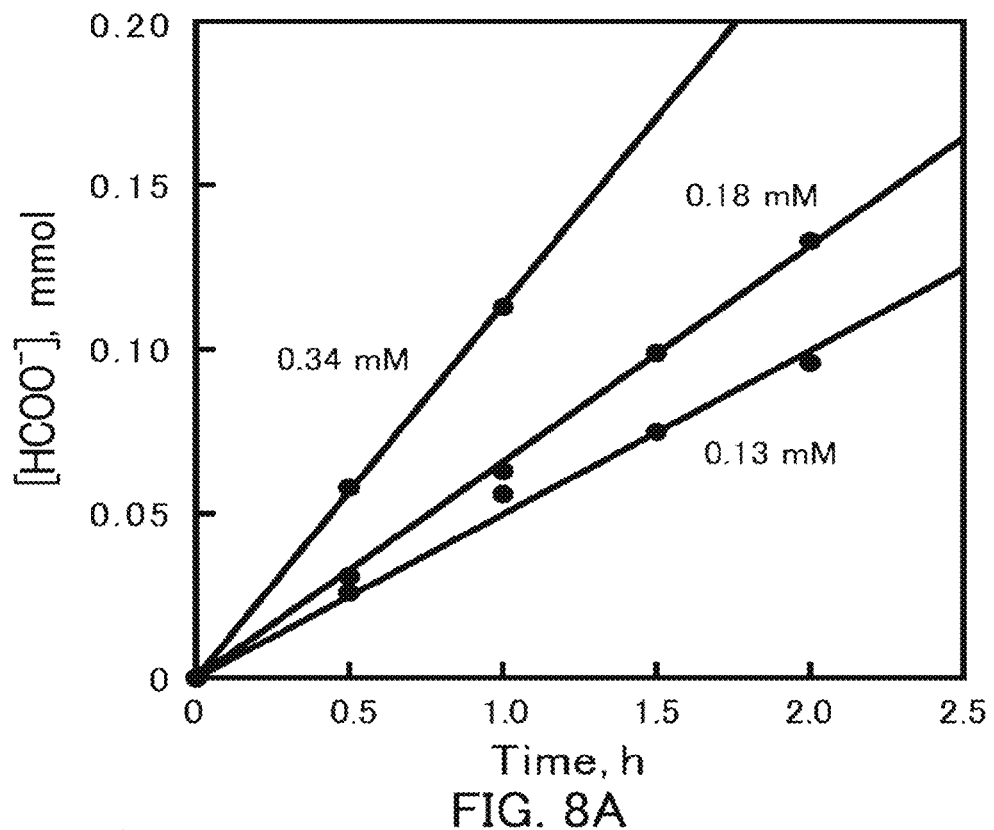
FIG. 8A is a graph showing, in Example 7, the catalyst concentration dependence of the amount of the generated formic acid in an aqueous solution of the iridium mononuclear aqua complex of Example 1.
Figure 8B:
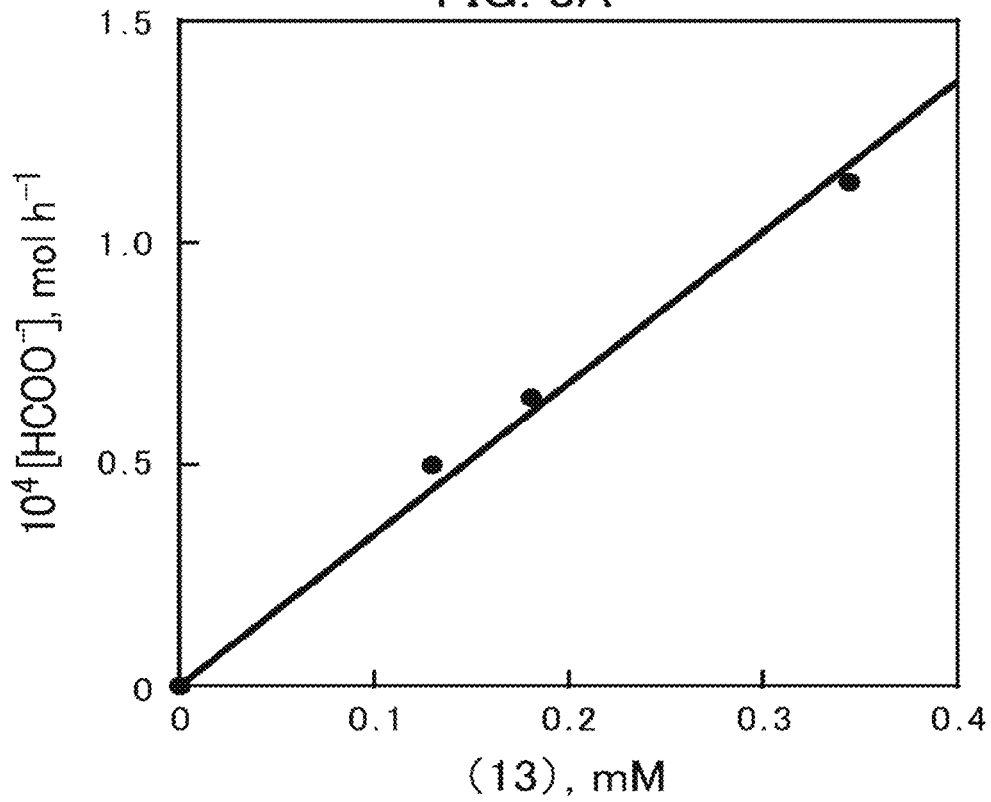
FIG. 8B is a graph showing the relationship between the catalyst concentration and the amount of the formic acid generated per unit time in Example 7.

Catalyst Concentration Dependence of Formic Acid Production and Carbon Dioxide Fixation The iridium mononuclear aqua complex (13) sulfate produced in Example 1 was dissolved in a potassium bicarbonate aqueous solution (2M) so that the catalyst concentration became 0.13 mM, 0.18 mM, and 0.34 mM, in order to examine the relationship between the amount of the generated formic acid and the catalyst concentration. These complex aqueous solutions each had a pH of 8.8. The concentration of the iridium mononuclear aqua complex (13) sulfate did not affect the pH of the aqueous solutions because it was low relative to the concentration of the potassium bicarbonate as described above. These complex aqueous solutions were allowed to stand in this state at 60° C. (333 K) in a hydrogen ($H_2$) atmosphere, thus causing a carbon dioxide fixation reaction (a formic acid production reaction) to start. The result thereof is shown in FIG. 8. FIG. 8A is a graph showing the relationship between the elapsed time from the start of the reaction and the amount of the generated formic acid, when the catalyst concentration in the complex aqueous solution was set to 0.13 mM, 0.18 mM, and 0.34 mM. In FIG. 8A, the horizontal axis indicates the reaction time (h), and the vertical axis indicates the formate ion concentration (mM). As can be seen from FIG. 8A, the amount of the generated (produced) formic acid increased linearly with the catalyst concentration in the complex aqueous solution. FIG. 8B is a graph showing the relationship between the catalyst concentration in the complex aqueous solution and the amount of the generated formic acid per unit time. In FIG. 8B, the horizontal axis indicates the concentration (mM) of the complex (13), and the vertical axis indicates the amount of the generated formic acid ($10^4$ molh$^{-1}$) per unit time. As can be seen from FIG. 8B, the amount of the generated formic acid per unit time also increased in proportion to the catalyst concentration.

Example 8

Figure 9A:
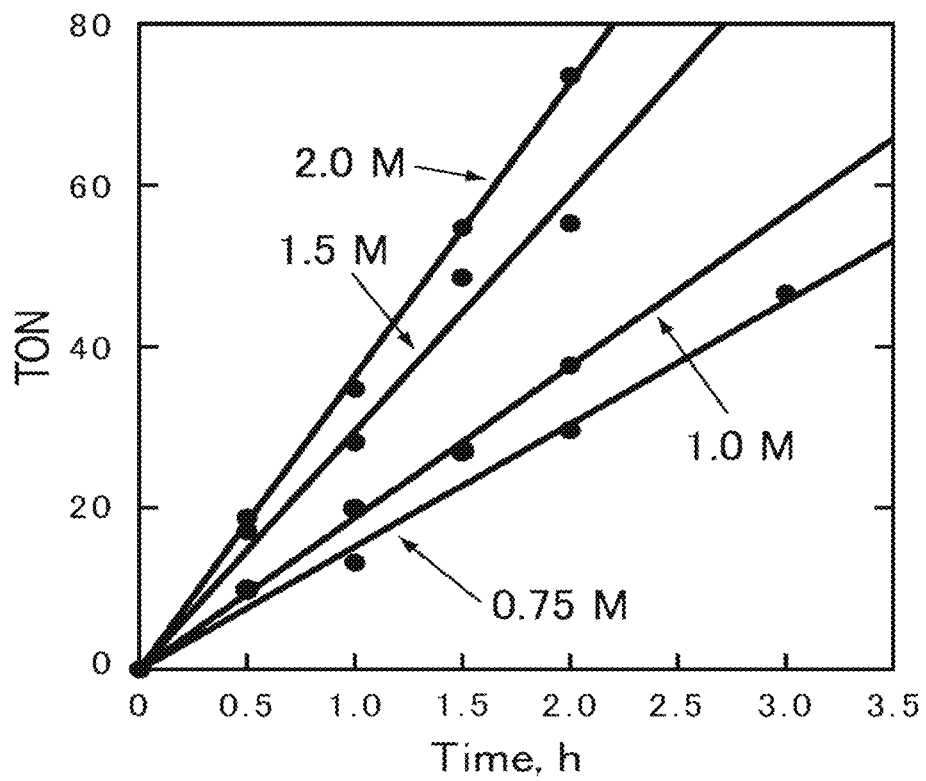
FIG. 9A is a graph showing, in Example 8, the bicarbonate ion concentration dependence of TON in an aqueous solution of the iridium mononuclear aqua complex of Example 1.
Figure 9B:
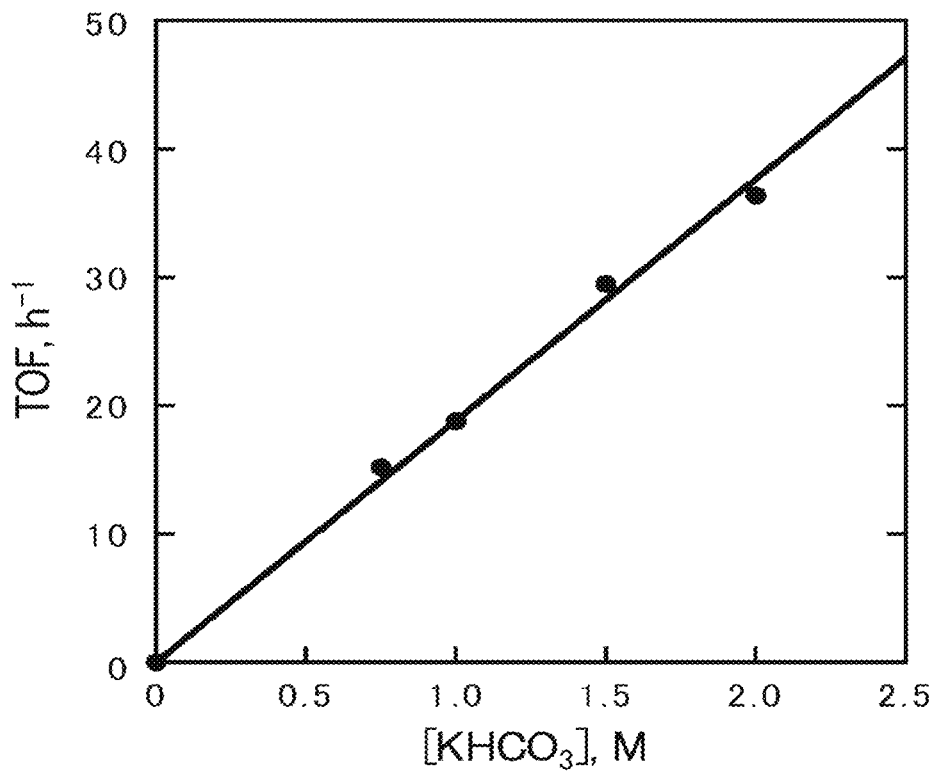
FIG. 9B is a graph showing the relationship between the bicarbonate ion concentration and TOF in Example 8.

Bicarbonate Ion Concentration Dependence of Formic Acid Production and Carbon Dioxide Fixation The iridium mononuclear aqua complex (13) sulfate produced in Example 1 was dissolved in each of 0.75 M, 1.0 M, 1.5 M, and 2.0 M potassium bicarbonate aqueous solutions, in order to examine the relationship between the amount of the generated formic acid and the concentration of bicarbonate ion (HCO$_3^-$). The complex aqueous solution prepared using the 2.0 M potassium bicarbonate aqueous solution had a pH of 8.8, and even if the concentration of the potassium bicarbonate was changed in the above-described range, the pH of the complex aqueous solution was substantially constant and mostly unchanged. These complex aqueous solutions (0.18 mM) were allowed to stand in this state at 60° C. (333 K) in a hydrogen ($H_2$) atmosphere, thus causing a carbon dioxide fixation reaction (formic acid production reaction) to start. The results thereof are shown in FIG. 9. FIG. 9A is a graph showing the relationship between the elapsed time from the start of the reaction and the amount of the generated formic acid, when the concentration of the potassium bicarbonate (the concentration of bicarbonate ion ($HCO_3^-$)) was set to 0.75 M, 1.0 M, 1.5 M, and 2.0 M. In FIG. 9, the horizontal axis indicates the reaction time (h), and the vertical axis indicates TON. As can be seen from FIG. 9A, according to the concentration of the potassium bicarbonate (the concentration of bicarbonate ion ($HCO_3^-$)), the TON increased in proportion to the reaction time, i.e., the amount of the generated (produced) formic acid increased in proportion to the reaction time. FIG. 9B is a graph showing the relationship between the concentration of the potassium bicarbonate (the concentration of bicarbonate ion ($HCO_3^-$)) and the TOF. In FIG. 9B, the horizontal axis indicates the concentration of potassium bicarbonate (M), and the vertical axis indicates the TOF. As can be seen from FIG. 9B, the TOF improved in proportion to the concentration of the potassium bicarbonate (the concentration of bicarbonate ion ($HCO_3^-$)).

Example 9

Temperature Dependence of Formic Acid Production and Carbon Dioxide Fixation

Figure 10A:
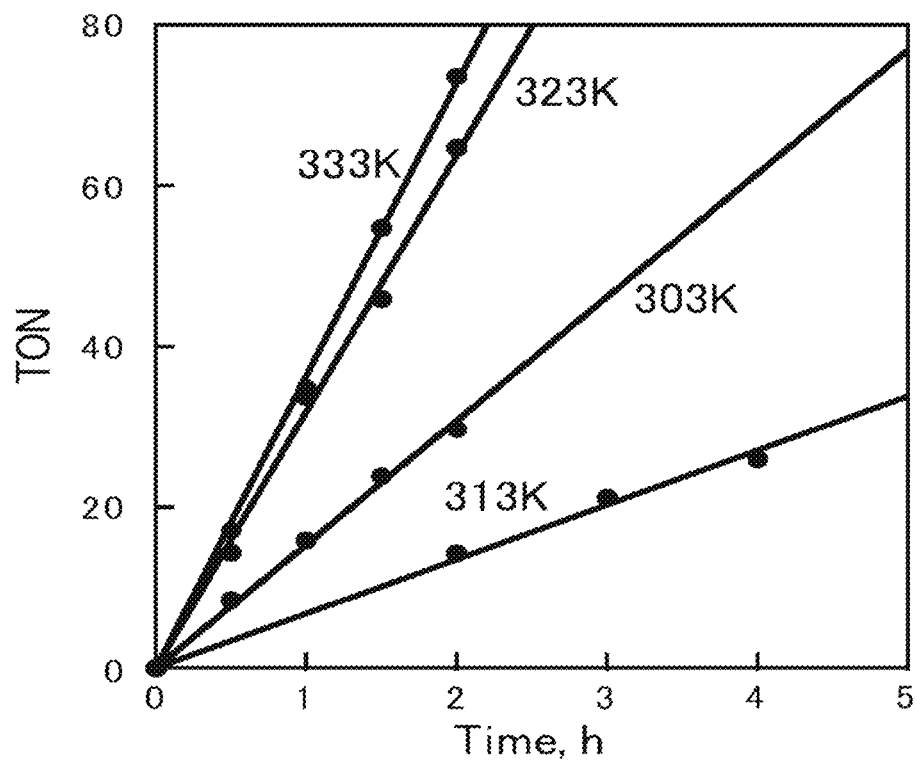
FIG. 10A is a graph showing, in Example 9, the temperature dependence of TON in an aqueous solution of the iridium mononuclear aqua complex of Example 1.
Figure 10B:
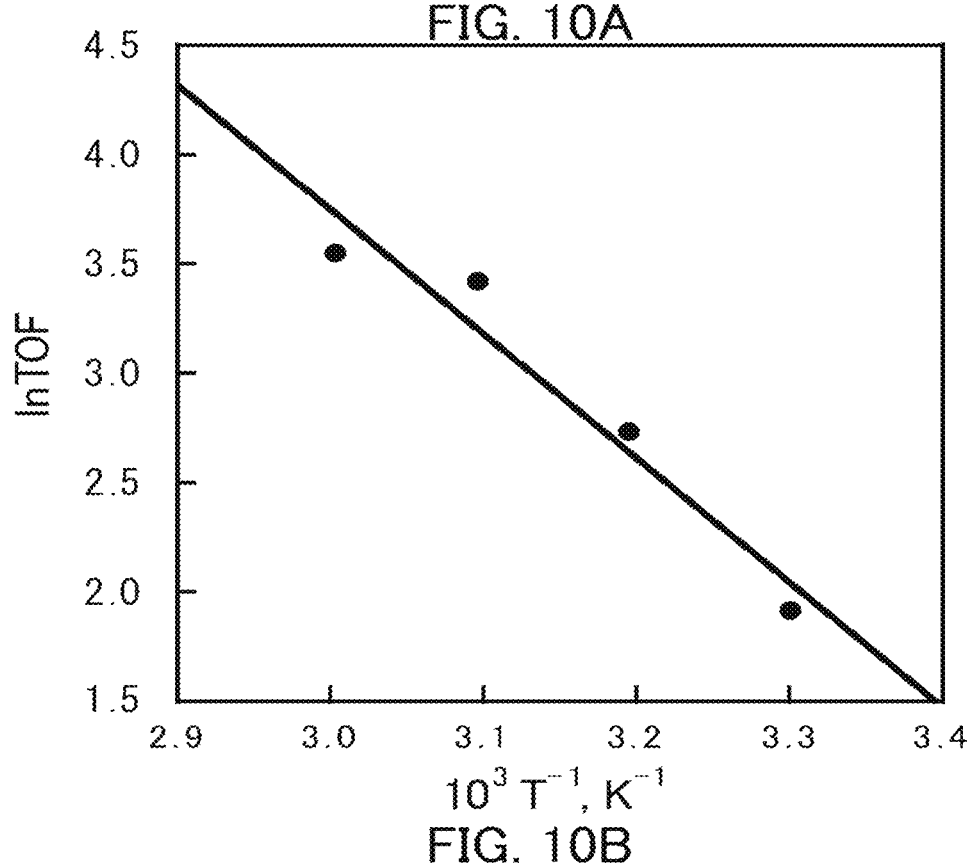
FIG. 10B is a graph showing the relationship between the reciprocal of the temperature and the logarithm of the TOF in Example 9.

The iridium mononuclear aqua complex (13) sulfate produced in Example 1 was dissolved in a potassium bicarbonate aqueous solution (2M). The pH of the complex aqueous solution was 8.8. This complex aqueous solution (0.18 mM) was allowed to stand in a hydrogen ($H_2$) atmosphere with the temperature of the complex aqueous solution being set to 30° C. (303 K), 40° C. (313 K), 50° C. (323 K), and 60° C. (333 K), thus causing a carbon dioxide fixation reaction (formic acid production reaction) to start. The results thereof are shown in FIG. 10. FIG. 10A is a graph showing the relationship between the elapsed time from the start of the reaction and the TON, when the temperature of the complex aqueous solution was set to 30° C. (303 K), 40° C. (313 K), 50° C. (323 K), and 60° C. (333 K). In FIG. 10A, the horizontal axis indicates the reaction time (h), and the vertical axis indicates the TON. As can be seen from FIG. 10A, at any of these temperatures, the TON increased in proportion to the reaction time, i.e., the amount of the generated (produced) formic acid increased in proportion to the reaction time. FIG. 10B is a graph showing the relationship between the reciprocal of the temperature of the complex aqueous solution and the logarithm of the TOF. In FIG. 10B, the horizontal axis indicates the reciprocal of the temperature ($10^3$ $T^{-1}$, $K^{-1}$), and the vertical axis indicates the natural logarithm (lnTOF) of the TOF. That is, FIG. 10B is an Arrhenius plot. As can be seen from FIG. 10B, the lnTOF decreased while exhibiting a negative slope with respect to the reciprocal of the temperature. That is, the lnTOF increased with the temperature rise.

Example 10

Figure 11:
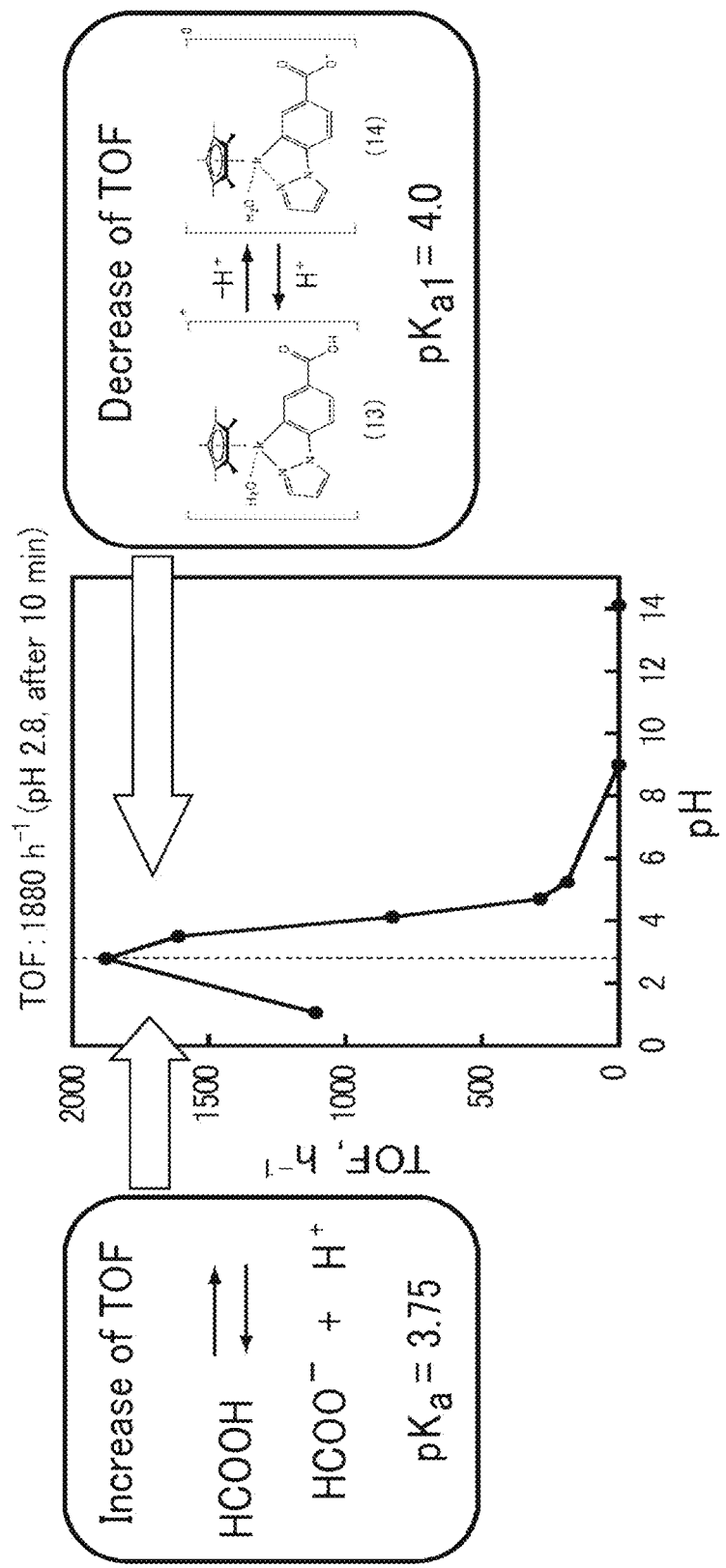
FIG. 11 is a graph showing, in Example 10, the relationship between the pH of an aqueous solution of the iridium mononuclear aqua complex of Example 1 and TOF.

Production of Hydrogen ($H_2$) and Decomposition of Formic Acid by Formic Acid Decomposition Catalyst The iridium mononuclear aqua complex (13) sulfate produced in Example 1 was dissolved in water, thus providing a complex aqueous solution (0.2 mM). To this aqueous solution, formic acid (3.3 M) was added under deoxygenated conditions at 1 atm. The initial pH of the complex aqueous solution at this time (the pH before the start of the formic acid decomposition reaction, i.e., the pH immediately after the addition of the formic acid) was measured and found to be 1.1. The complex aqueous solution was allowed to stand in this state at room temperature (25° C. (298 K)). Then, gas generation was observed clearly through visual observation. This gas was analyzed by GC (Gas Chromatography), and it was found that the gas was a mixed gas of hydrogen and carbon dioxide (1:1). This gas was blown into sodium hydroxide (5M) to cause bubbling, thereby separating and removing the carbon dioxide therefrom. Thereafter, the gas was subjected to quantitative analysis by GC (Gas Chromatography). Also, hydrogen generated using complex aqueous solutions, which were the same as the above complex aqueous solution except that they have various initial pHs different from that of the above complex aqueous solution, were subjected to the same quantitative analysis. The adjustment of the initial pH was achieved as follows: a 5M sodium hydroxide aqueous solution was added to obtain the aqueous solution with a pH of 14.1 (see the graph of FIG. 11); and the initial pHs of the other aqueous solutions were adjusted by using, instead of formic acid (3.3M), a mixture of formic acid and potassium formate (the concentration of the mixture was 3.3M, which was constant) and adjusting the mixing ratio (the amount-of-substance ratio) of the formic acid and the potassium formate. FIG. 11 is a graph showing the relationship between the pH of the complex aqueous solution and the TOF determined based on an initial velocity of hydrogen generation. In FIG. 11, the horizontal axis indicates the pH, and the vertical axis indicates the TOF. As can be seen from FIG. 11, hydrogen generation was observed when the pH of the complex aqueous solution was in the range of not less than 1 and less than 9. It was found that the TOF reached its maximum when the pH of the complex aqueous solution was around 2.8. The TOF calculated based on the catalyst TON measured for 10 minutes after the addition of the formic acid at this pH was 1880 $h^{-1}$. This is the world highest TOF in a formic acid decomposition reaction in water at room temperature known at the time this application was filed. That is, the iridium mononuclear aqua complex (13) sulfate produced in Example 1 had high catalytic activity and could be used as a formic acid decomposition catalyst that allows efficient production of hydrogen ($H_2$) by decomposing formic acid in a formic acid-containing aqueous solution at ordinary temperature and ordinary pressure.

Figure 12A:
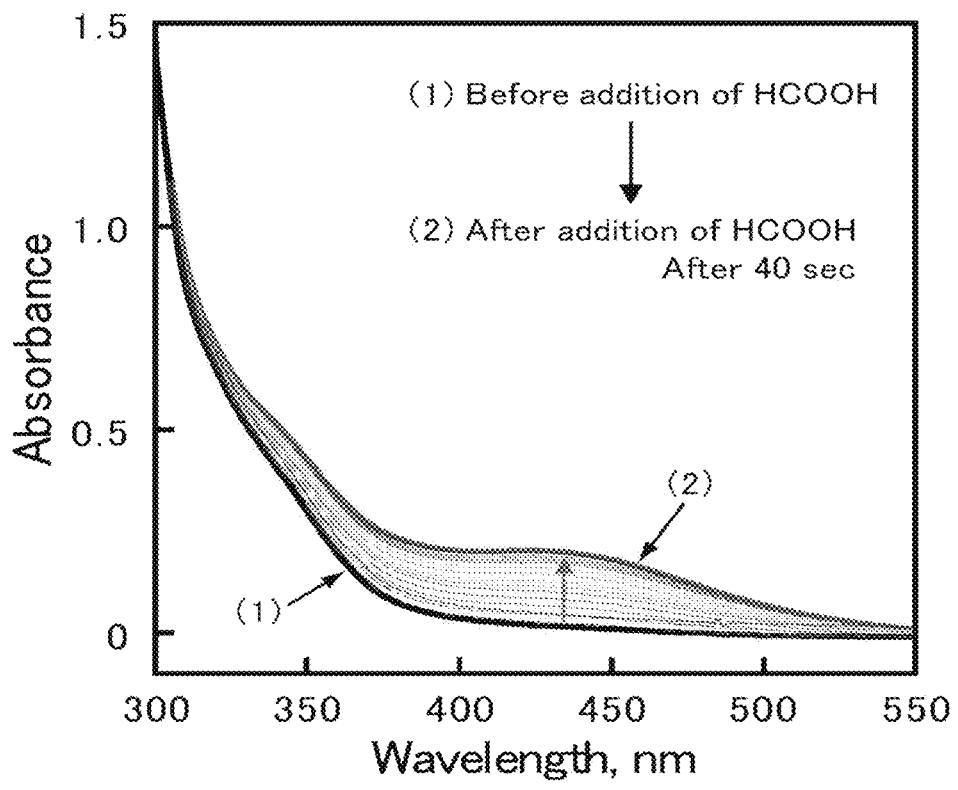
FIG. 12A is a graph showing the change in absorption spectrum of an aqueous solution of the iridium mononuclear aqua complex of Example 1 before and after the addition of formic acid to the aqueous solution.

FIG. 12A shows the change in UV-Vis. spectrum by the addition of formic acid to a complex aqueous solution of the iridium mononuclear aqua complex (13) produced in Example 1. In FIG. 12A, the horizontal axis indicates the wavelength (nm), and the vertical axis indicates the absorbance. The conditions were set as follows. Specifically, first, the iridium mononuclear aqua complex (13) sulfate produced in Example 1 was dissolved in water, thus providing a complex aqueous solution (0.15 mM) (2 ml). To this aqueous solution, a formic acid/potassium formate aqueous solution (0.26 μmol (0.26 M), 10 μl) was added under deoxygenated conditions at 1 atm. The change in UV-Vis. spectrum before the addition of the formic acid ((1) in FIG. 12A) and 40 seconds after the addition ((2) in FIG. 12A) was measured. This measurement was carried out in deaerated water at 298 K using a 1-cm optical path length. As can be seen from FIG. 12A, the UV-Vis. spectrum changed before and after the addition of the formic acid to the complex aqueous solution. From this result, it is presumed that the iridium mononuclear aqua complex produced in Example 1 forms a formic acid complex by reacting with formic acid added to the complex aqueous solution.

Figure 12B:
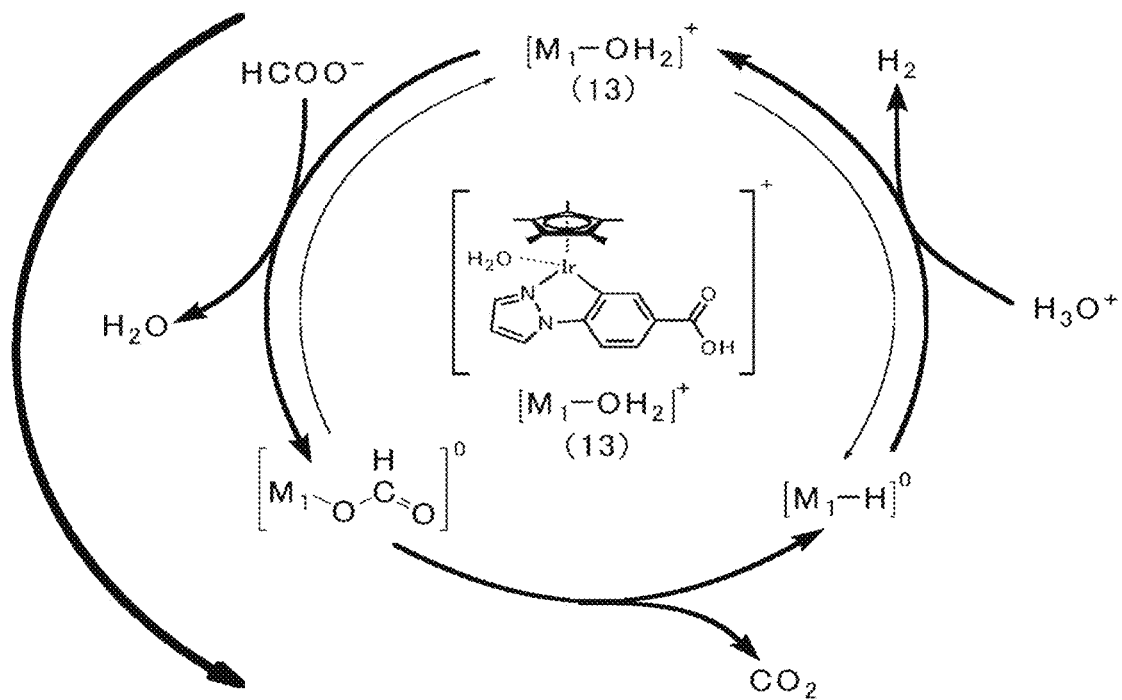
FIG. 12B is a scheme showing an example of a presumable reaction mechanism of formic acid decomposition in the iridium mononuclear aqua complex of Example 1.

Based on the above presumption, a presumable reaction mechanism of formic acid decomposition by the iridium mononuclear aqua complex produced in Example 1 is shown in the scheme of FIG. 12B. In FIG. 12B, "$M_1$" means a moiety in the structure of the iridium mononuclear aqua complex represented by the formula (13) excluding the ligand (water molecule) corresponding to the ligand L in the formula (1). As can be seen from FIG. 12B, when formic acid is added to this complex aqueous solution (pH 2.0), the iridium mononuclear aqua complex (13) present in this complex aqueous solution reacts with a formic acid anion, thereby generating a formic acid complex. This formic acid complex turns to a hydrido complex after the elimination of carbon dioxide. This hydrido complex reacts with proton ($H_3O^+$) to generate hydrogen ($H_2$). It is presumed that, through these processes, the iridium mononuclear aqua complex produced in Example 1 decomposes formic acid to generate (produce) hydrogen ($H_2$). It is to be noted, however, that this reaction mechanism merely is an example of a presumable mechanism, and does not limit the present invention by any means.

Example 11

Figure 13A:
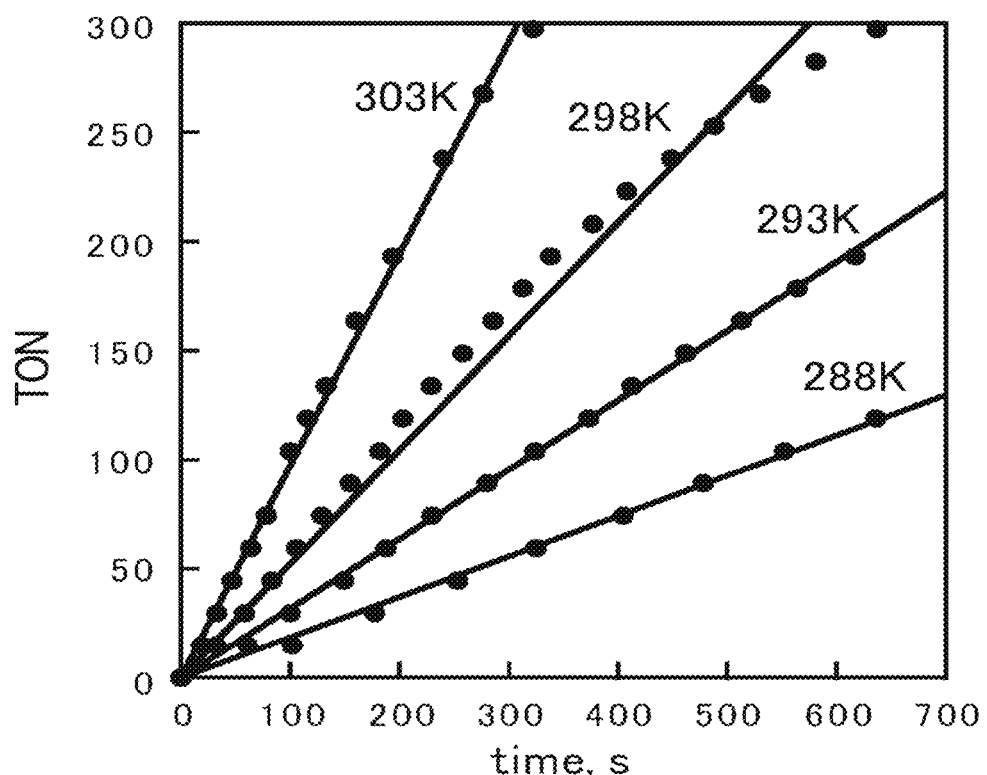
FIG. 13A is a graph showing, in Example 11, the temperature dependence of TON in an aqueous solution of the iridium mononuclear aqua complex of Example 1.
Figure 13B:
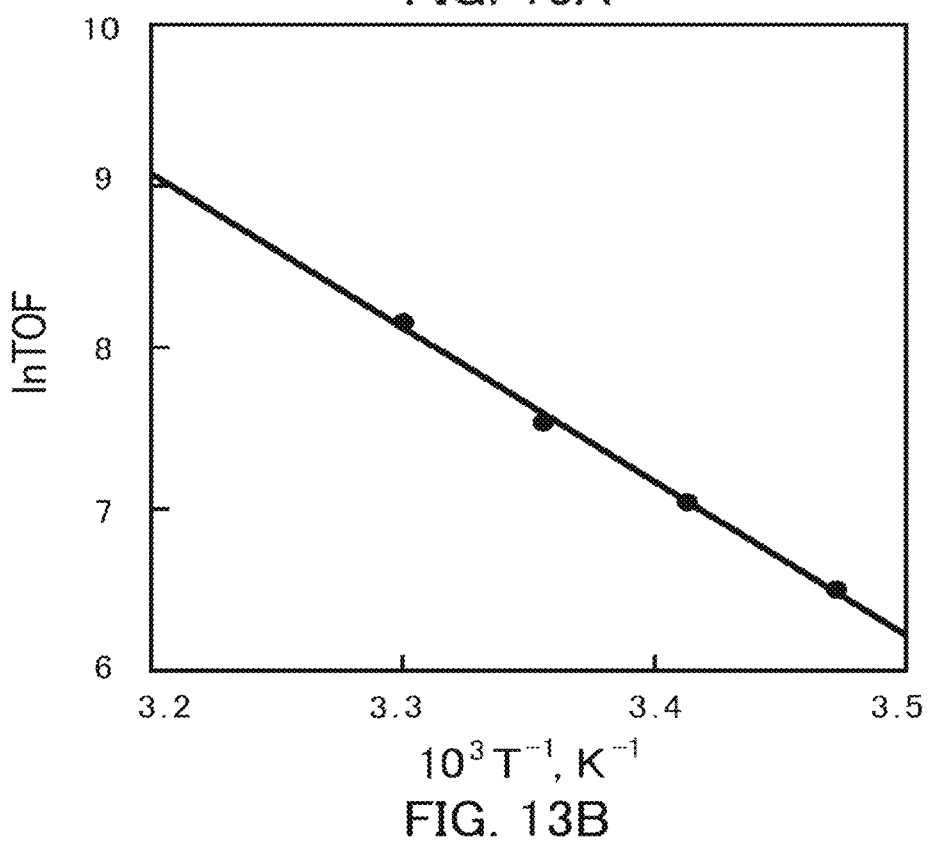
FIG. 13B is a graph showing the relationship between the reciprocal of the temperature and the logarithm of the TOF in Example 11.

Temperature Dependence of Hydrogen ($H_2$) Production and Formic Acid Decomposition The iridium mononuclear aqua complex (13) sulfate produced in Example 1 was dissolved in water, thus providing a complex aqueous solution (0.2 mM). The initial pH of the complex aqueous solution at this time (the pH before the start of the formic acid decomposition reaction) was measured and found to be 2.78. The temperature of this complex aqueous solution was set to 15° C. (288 K), 20° C. (293 K), 25° C. (298 K) and 30° C. (303 K), and a formic acid/potassium formate aqueous solution (3.3M) was added to this aqueous solution under deoxygenated conditions at 1 atm. As a result, gas generation was observed clearly by visual observation. The results thereof are shown in FIG. 13. FIG. 13A is a graph showing the relationship between the elapsed time from the start of the reaction and the TON, when the temperature of the complex aqueous solution was set to 30° C. (303 K), 40° C. (313 K), 50° C. (323 K), and 60° C. (333 K). In FIG. 13A, the horizontal axis indicates the reaction time (s), and the vertical axis indicates the TON. As can be seen from FIG. 13A, at any of these temperatures, the TON increased in proportion to the reaction time, i.e., the amount of the generated (produced) hydrogen ($H_2$) increased in proportion to the reaction time. FIG. 13B is a graph showing the relationship between the reciprocal of the temperature of the complex aqueous solution and the logarithm of the TOF. In FIG. 13B, the horizontal axis indicates the reciprocal of the temperature ($10^3$ $T^{-1}$, $K^{-1}$), and the vertical axis indicates the logarithm of the TOF (lnTOF). That is, FIG. 13B is an Arrhenius plot. As can be seen from FIG. 13B, the logarithm of the TOF decreased while exhibiting a negative slope with respect to the reciprocal of the temperature. That is, the logarithm of the TOF increased with the temperature rise.

Example 12

Figure 14:
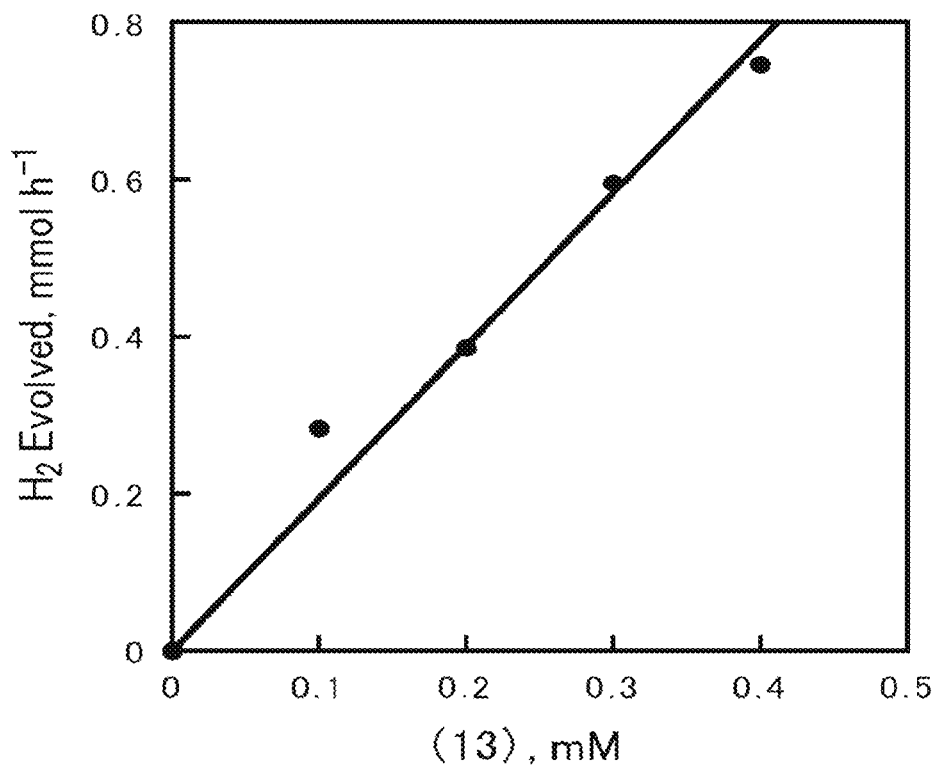
FIG. 14 is a graph showing, in Example 12, the catalyst concentration dependence of the amount of the generated hydrogen in an aqueous solution of the iridium mononuclear aqua complex of Example 1.

Catalyst Concentration Dependence of Hydrogen ($H_2$) Production and Formic Acid Decomposition The iridium mononuclear aqua complex (13) sulfate produced in Example 1 was dissolved in water so that the catalyst concentration thereof was 0.1 mM, 0.2 mM, 0.3 mM, and 0.4 mM, thus preparing complex aqueous solutions, in order to examine the relationship between the amount of the generated (produced) hydrogen ($H_2$) and the catalyst concentration. The initial pHs of the complex aqueous solutions at this time (the pH before the start of the formic acid decomposition reaction) were measured and found to be 2.78. In this state, the temperature of these complex aqueous solutions was set to 25° C. (298 K), and a formic acid/potassium formate aqueous solution (3.3M) was added to each of these aqueous solutions under deoxygenated conditions at 1 atm. The results thereof are shown in FIG. 14. FIG. 14 is a graph showing the relationship between the catalyst concentration and the amount of hydrogen ($H_2$) generated (produced) per unit time, when the catalyst concentration in the complex aqueous solution was set to 0.1 mM, 0.2 mM, 0.3 mM, and 0.4 mM. In FIG. 14, the horizontal axis indicates the concentration (mM) of the catalyst (the complex (13)), and the vertical axis indicates the amount of $H_2$ generated per unit time (mmol $h^{-1}$). As can be seen from FIG. 14, the amount of the generated (produced) hydrogen ($H_2$) increased in proportion to the catalyst concentration.

Example 13

Figure 15:
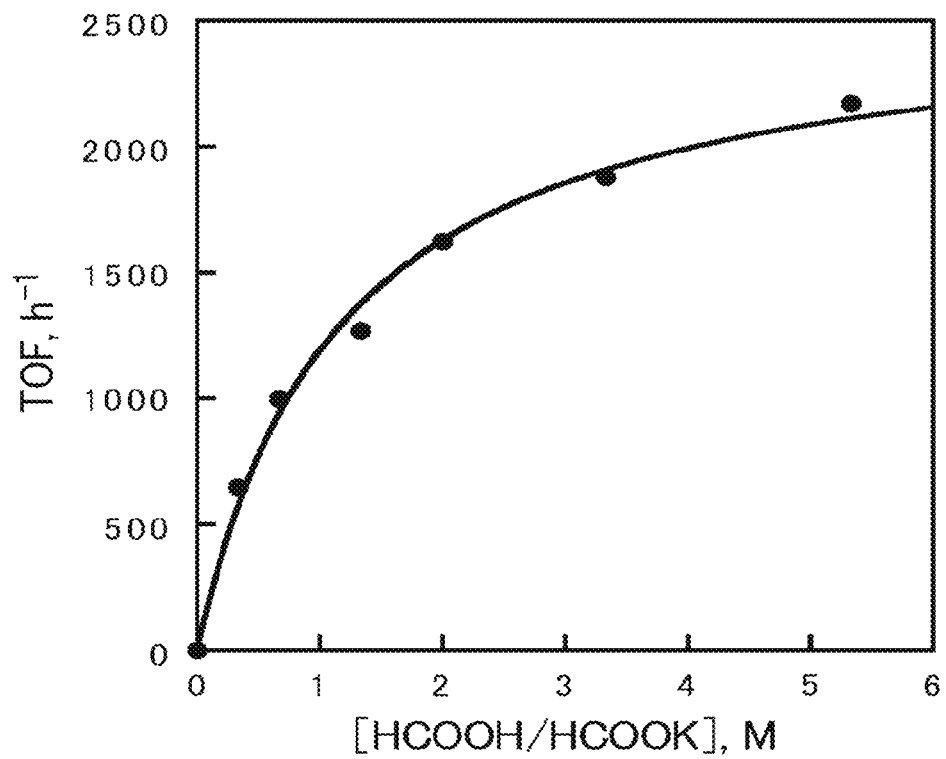
FIG. 15 is a graph showing, in Example 13, the formic acid concentration dependence of TOF in an aqueous solution of the iridium mononuclear aqua complex of Example 1.

Formic Acid Concentration Dependence of Hydrogen ($H_2$) Production and Formic Acid Decomposition The iridium mononuclear aqua complex (13) sulfate produced in Example 1 was dissolved in water, thus preparing a complex aqueous solution (0.2 mM). The initial pH of the complex aqueous solution at this time (the pH before the start of the formic acid decomposition reaction) was measured and found to be 2.78. In this state, the temperature of the complex aqueous solution was set to 25° C. (298 K), and a formic acid/potassium formate aqueous solution was added thereto under deoxygenated conditions at 1 atm so that the concentration of the formic acid/potassium formate was in the range from about 0.3 M to about 5 M. The results thereof are shown in FIG. 15. FIG. 15 is a graph showing the relationship between the concentration of the formic acid/potassium formate in the aqueous solution and the TOF, when the concentration of the formic acid/potassium formate in the aqueous solution was changed in the range from about 0.3 M to about 5 M. In FIG. 15, the horizontal axis indicates the concentration (M) of the formic acid/potassium formate aqueous solution, and the vertical axis indicates the TOF. As can be seen from FIG. 15, the TOF improved linearly with the concentration of the formic acid/potassium formate in the aqueous solution and reached a predetermined limit value.

Figure 21:
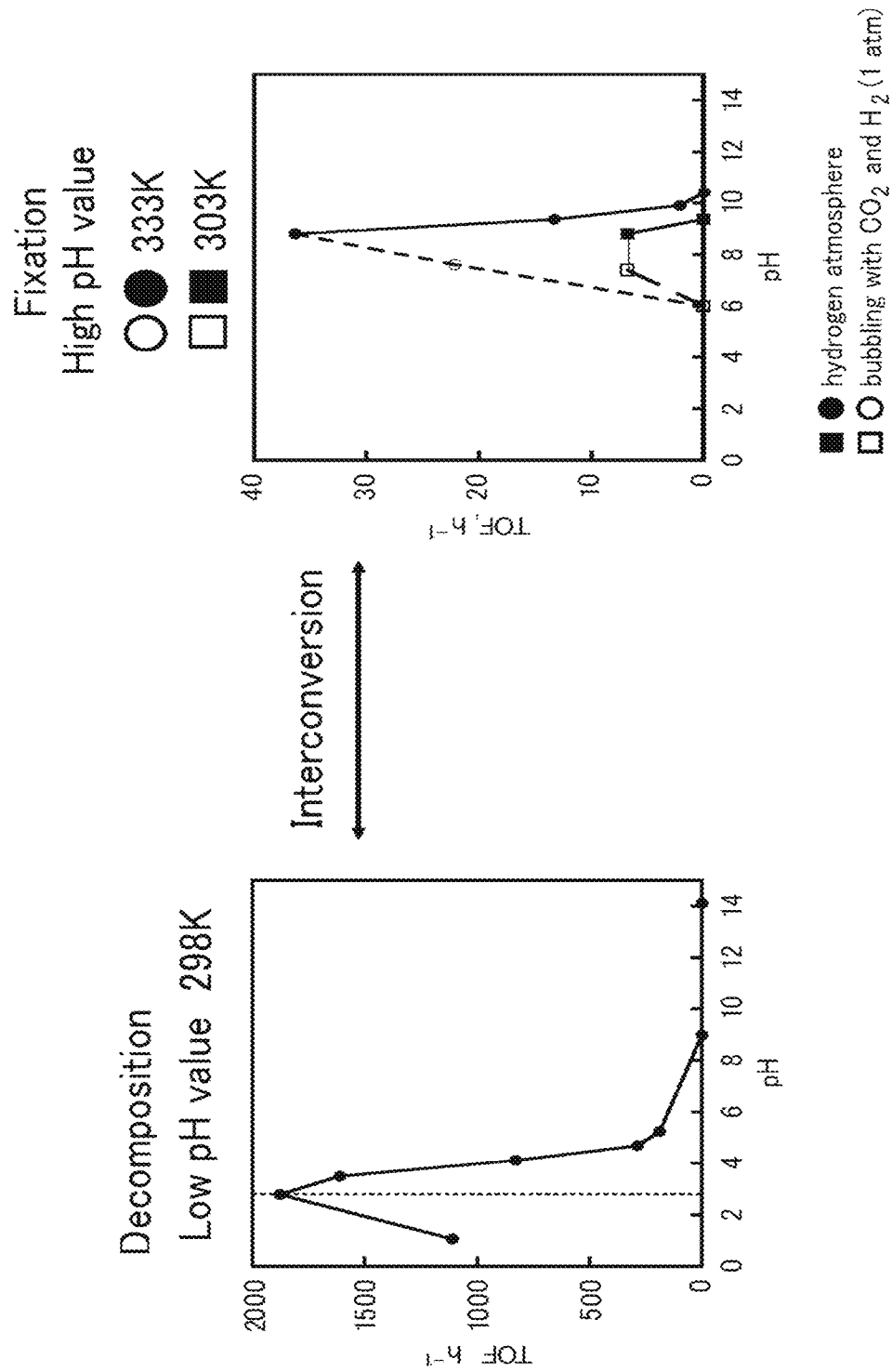
FIG. 21 shows graphs demonstrating that the iridium mononuclear aqua complex of Example 1 has functions of both a carbon dioxide fixation catalyst and a formic acid decomposition catalyst.

As specifically described above, the iridium mononuclear aqua complex (13) produced in Example 1 and the iridium mononuclear aqua complex (16) produced in Example 2 each could be used as a carbon dioxide fixation catalyst that allows efficient production of formic acid by reacting carbon dioxide with hydrogen ($H_2$) to fix the carbon dioxide in an aqueous solution at ordinary temperature and ordinary pressure. In particular, the iridium mononuclear aqua complex (13) produced in Example 1 could be used as a formic acid decomposition catalyst that allows efficient production of hydrogen ($H_2$) by decomposing formic acid in a formic acid-containing aqueous solution at ordinary temperature and ordinary pressure, as described in Examples 10 to 13. That is, the iridium mononuclear aqua complex (13) produced in Example 1 has both the function of a carbon dioxide fixation catalyst and the function of a formic acid decomposition catalyst, as shown in FIG. 21. Such a mononuclear metal complex is newly discovered by the inventors of the present invention. The interconversion between these functions can be achieved by changing the pH of an aqueous solution of the iridium mononuclear aqua complex (13) produced in Example 1.

In the following, an iridium complex that was the same as that described in the above-described Non-Patent Document 1 (Himeda, Y. et al., Organometallics 2007, 26, pp. 702-712) was produced (synthesized) for comparison with the mononuclear metal complex of the present invention, and the catalytic properties thereof were evaluated. In the complex production comparative example to be described below, sulfate of the iridium complex described in Non-Patent Document 1 was produced instead of hydrochloride thereof, and the catalytic properties of the iridium complex sulfate were evaluated.

Complex Production Comparative Example 1

Production of Iridium Complex Sulfate

An iridium complex sulfate represented by the following formula (21) was produced (synthesized). This will be described specifically below.

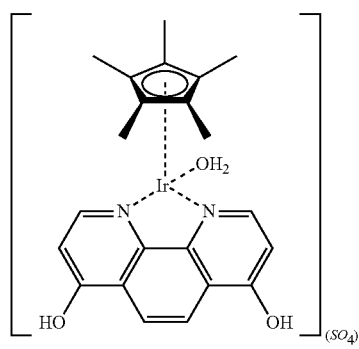

(21)

The iridium complex sulfate represented by the formula (21) was produced according to the method described in Example 1. Specifically, first, an aqueous solution was prepared by adding 4,7-dihydroxy-1,10-phenanthroline (88.9 mg, 0.419 mmol) to water (20 ml). To this aqueous solution, the complex (108) sulfate, namely, the $[Cp*Ir(H_2O)_3]^{2+}$ sulfate, produced in Step 2, (200 mg, 0.419 mmol) was added in an argon atmosphere, and the resultant mixture was stirred for 12 hours in the dark at 40° C. After the stirring, this solution was filtered through a membrane filter (made of PTFE (polytetrafluoroethylene), manufactured by ADVANTEC). This filtrate was evaporated to remove moisture therefrom and then was vacuum-dried. Thus, the iridium complex sulfate represented by the formula (21) was obtained (the yield calculated based on the $[C_p*Ir(H_2O)_3]^{2+}$ sulfate: 81%).

Then, as described below, the performance of this iridium complex sulfate (21) as a carbon dioxide fixation catalyst was evaluated in the same manner as in Example 1.

Comparative Example 1

Figure 23:
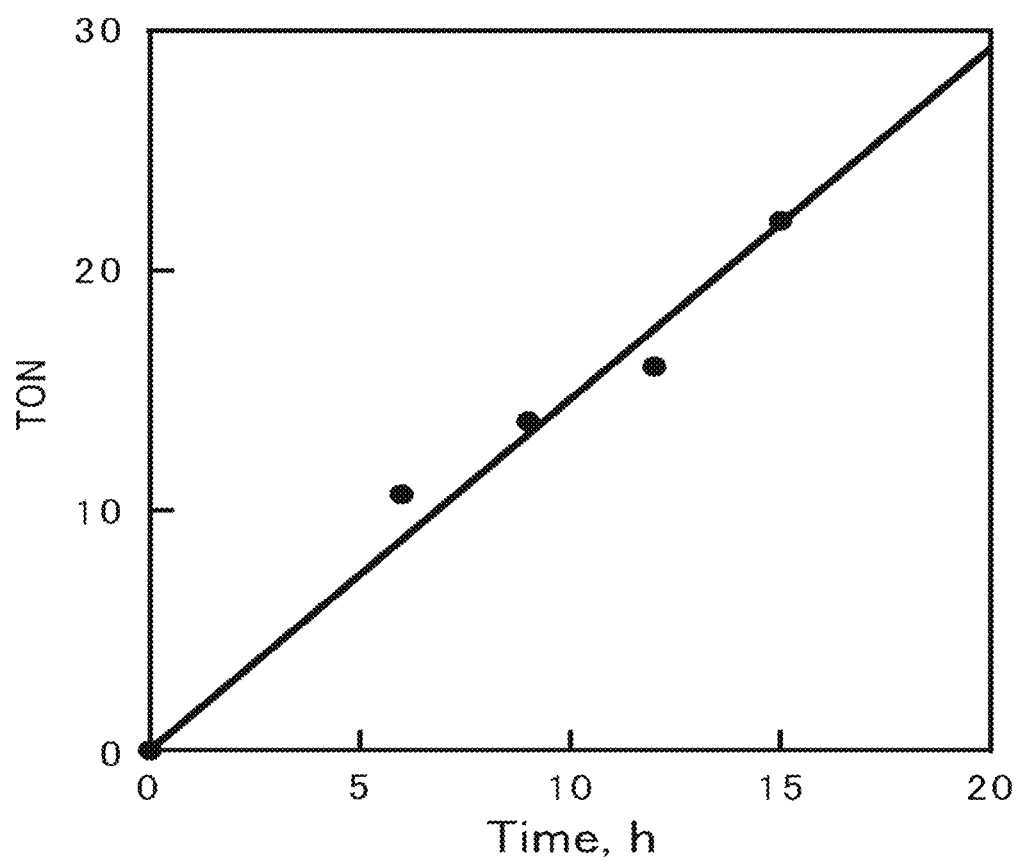
FIG. 23 is a graph showing, in Comparative Example 1, the relationship between the passage of reaction time and TON in an aqueous solution of an iridium complex according to Complex Production Comparative Example 1.

Formic Acid Production and Carbon Dioxide Fixation by Carbon Dioxide Fixation Catalyst The iridium complex sulfate (21) produced in Complex Production Comparative Example 1 was dissolved in a potassium carbonate aqueous solution (0.1 mM) in the same manner as in Example 3. Carbon dioxide under ordinary pressure (1 atm) was blown into this complex aqueous solution (0.26 mM) for 1 hour at room temperature (30° C. (303 K)) under deoxygenated conditions. Thus, the complex aqueous solution was saturated with carbon dioxide. The pH of the complex aqueous solution at this time was 7.5. In this state, carbon dioxide with ordinary pressure (1 atm) and hydrogen ($H_2$) with ordinary pressure (1 atm) were blown into the complex aqueous solution at the same time at a flow rate of 10 cc/min to cause bubbling. Thus, a carbon dioxide fixation reaction (formic acid production reaction) was started. Aliquot parts of this reaction solution were collected at time intervals of 3 hours, and $^1$H-NMR measurement was carried out in the same manner as in Example 3. As a result of the $^1$H-NMR measurement, the generation of formic acid was observed, and the amount of the generated formic acid could be determined. The change in TON with time was plotted, which indicates that, as shown in FIG. 23, the TON increased in proportion to the elapsed time from the start of the reaction. However, the TOF determined as the constant of proportionality was low (1.5 h$^{-1}$). It was found that this value is lower than the TOF described in Non-Patent Document 1, which was determined by quantifying the amount of the generated formic acid by high performance liquid chromatography.

As described above, under the conditions of the present example (comparative example), the iridium complex sulfate (21) produced in Complex Production Comparative Example 1 exhibited the function of a carbon dioxide fixation catalyst that allows formic acid production by reacting carbon dioxide with hydrogen ($H_2$) to fix the carbon dioxide in an aqueous solution at ordinary temperature and ordinary pressure. However, the catalytic activity of the iridium complex sulfate (21) was low.

Example 14

Production of Iridium Mononuclear Hydrido Complex (15A)

The iridium mononuclear aqua complex (13) sulfate produced in Example 1 (8 mg, 14 µmol) was dissolved in deoxygenated water (50 µl). The pH of the complex aqueous solution at this time was 1.7. In this state, hydrogen ($H_2$) under ordinary pressure (1 atm) was blown into the complex aqueous solution at a flow rate of 50 cc/min to cause bubbling for 5 minutes. In order to separate the precipitates generated thereby, the complex aqueous solution was centrifuged, then subjected to decantation, and further vacuum-dried. Thus, a desired iridium mononuclear hydrido complex (15A), namely, [IrCp*(4-(1H-pyrazole-1-yl-κN$^{2-}$)benzoic acid-κC$^3$)H]$^0$, was obtained in the form of orange powder. Instrumental analysis values ($^1$H-NMR) of the iridium mononuclear hydrido complex (15A) are shown below. The scheme of the above reaction and the $^1$H-NMR chart regarding the iridium mononuclear hydrido complex (15A) are the same as those shown in FIG. 6.

$^1$H-NMR (DMSO-d$_6$, 298 K): δ (ppm) 1.87 (s, η$^5$-C$_5$(CH$_3$)$_5$, 15H), 6.66 (d, d, J=2.2 Hz, J=2.7 Hz, 1H), 7.49 (d, d, J=8.4 Hz, J=1.5 Hz, 1H), 7.56 (d, J=8.4 Hz, 1H), 7.79 (s, 1H), 8.18 (s, 1H), 8.62 (d, J=2.7 Hz, 1H)

Example 15

Production of Iridium Mononuclear Hydrido Complex (15B)

Figure 24:
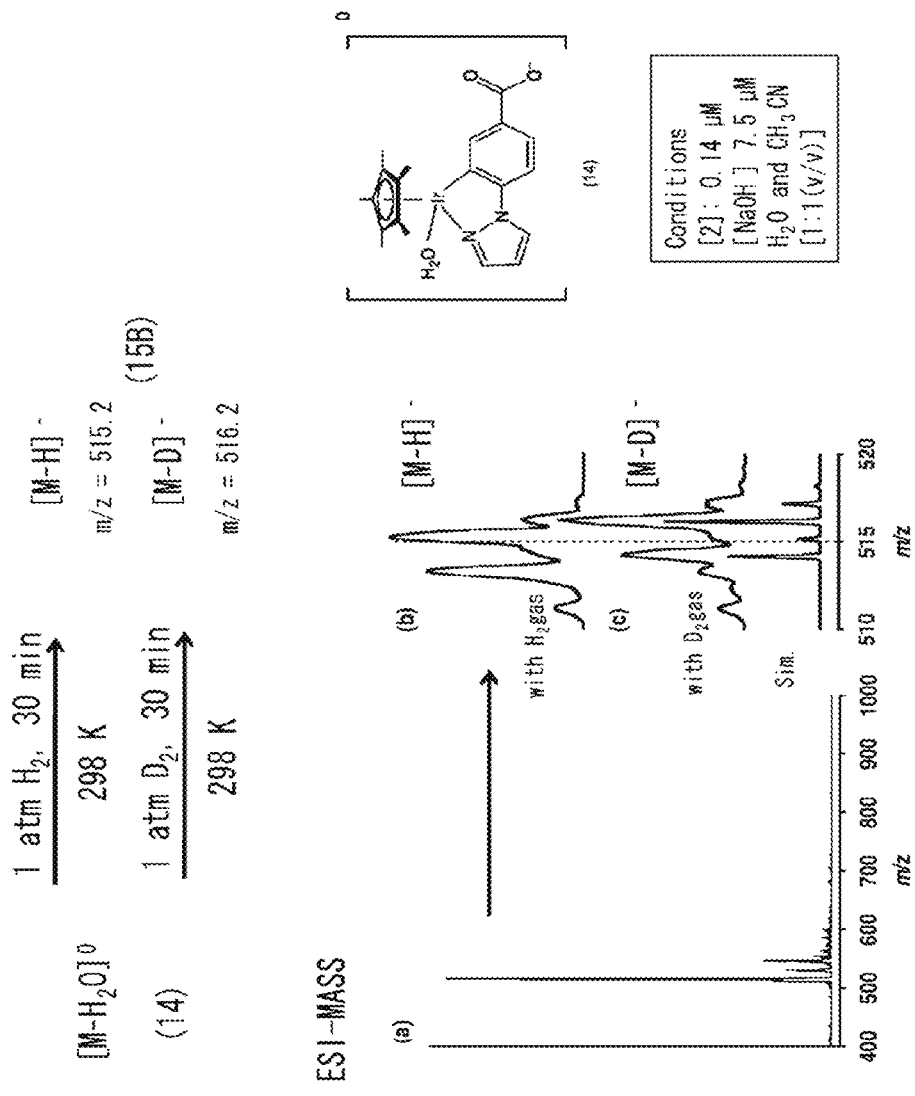
FIG. 24 shows a reaction scheme in Example 15 (production of an iridium mononuclear hydrido complex) and a mass spectrum of the iridium mononuclear hydrido complex.

NaOH (0.6 µg, 0.015 µmol) was dissolved in 1 ml of water, thus preparing a 15 µM NaOH aqueous solution. To this aqueous solution, the same amount of acetonitrile was added, thus preparing a 7.5 µM NaOH solution (water:acetonitrile=1:1 (volume ratio)). The iridium mononuclear aqua complex (13) sulfate produced in Example 1 (0.16 µg, 0.00028 µmol) was dissolved therein, thus preparing an alkali-neutralized 0.14 µM iridium mononuclear aqua complex (14) solution. Subsequently, hydrogen ($H_2$) under ordinary pressure (1 atm) was blown into this complex solution at room temperature (25° C. (298 K)) under deoxygenated conditions to cause bubbling for 30 minutes. This solution was measured by ESI-MASS spectrometry in the negative ion mode. As a result, a spectrum derived from the iridium mononuclear hydrido complex (15B), namely, $[IrCp^*(4\text{-}(1H\text{-pyrazole-1-yl-}\kappa N^{2-})\text{benzoic acid-}\kappa C^3)H]^{-1}$, was obtained. Also, the reaction was carried out in the same manner as in the above, except that heavy hydrogen ($D_2$) was used instead of hydrogen ($H_2$). As a result, a spectrum derived from the deuterated iridium mononuclear hydrido complex (15B), namely, $[IrCp^*(4\text{-}(1H\text{-pyrazole-1-yl-}\kappa N^{2-})\text{benzoic acid-}\kappa C^3)D]^{-1}$, was obtained. Instrumental analysis values (MS) of the iridium mononuclear hydrido complex (15B) are shown below. FIG. 24 shows the scheme of the above reaction and the mass spectrum of the iridium mononuclear hydrido complex (15B). The UV-Vis. spectra of the iridium mononuclear hydrido complex (15B) are shown at the lower right of FIGS. 25 and 26.

MS: $IrCp^*(4\text{-}(1H\text{-pyrazole-1-yl-}\kappa N^2)\text{benzoic acid-}\kappa C^3)H]^{-1}$ m/z=515.2

$IrCp^*(4\text{-}(1H\text{-pyrazole-1-yl-}\kappa N^2)\text{benzoic acid-}\kappa C^3)D]^{-1}$ m/z=516.2

As described above, in Examples 14 and 15, the iridium mononuclear hydrido complex (15A) or (15B) could be produced from hydrogen gas and the iridium mononuclear aqua complex (13). As a result of mass spectrometry, it was found that the molecular weight of the hydrido complex obtained when heavy hydrogen gas was used was greater by 1 than that of the hydrido complex obtained when hydrogen gas was used. From this result, it was confirmed that the hydrogen source of the hydrido was the hydrogen gas. Also, as described above, it was confirmed that, in Example 5, formic acid could be produced (carbon dioxide could be fixed) by blowing carbon dioxide into the system together with hydrogen gas.

Example 16

Figure 25:
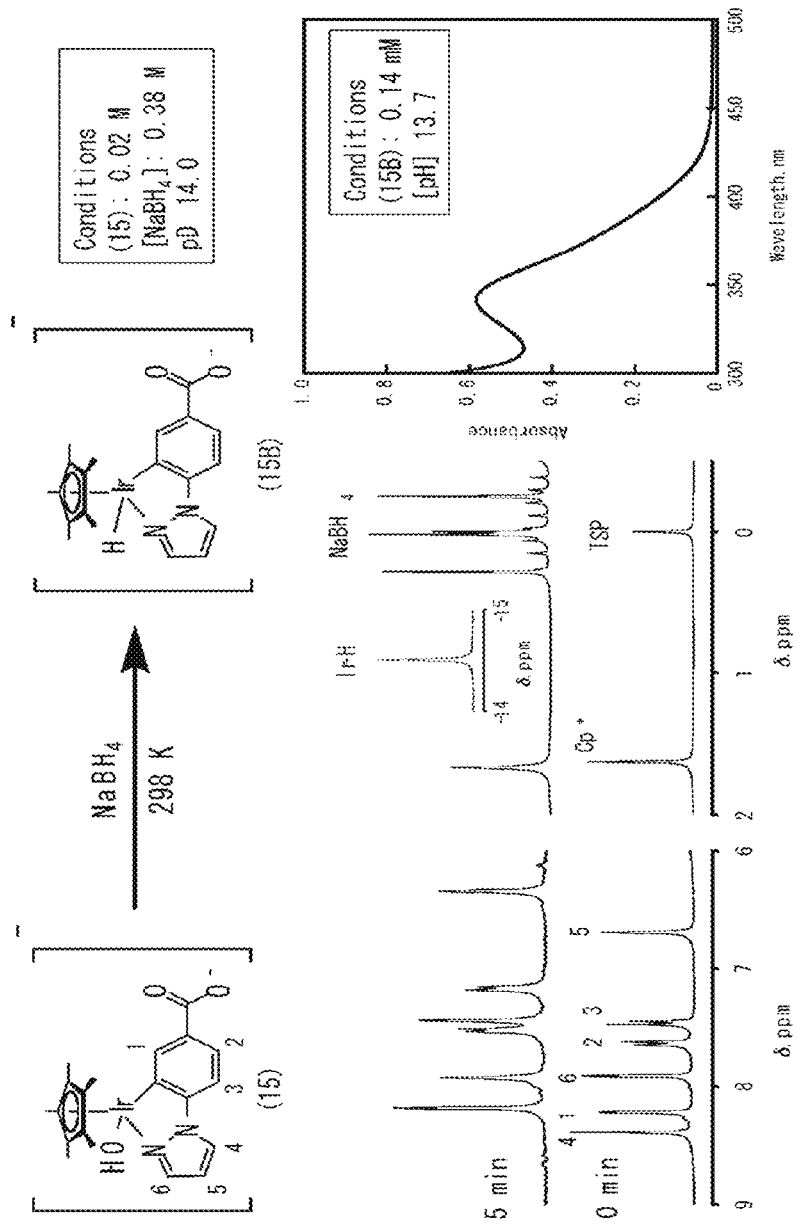
FIG. 25 shows $^1$H-NMR and a UV-Vis. spectrum of an iridium mononuclear hydrido complex, measured in Example 16.

Production of Iridium Mononuclear Hydrido Complex (15B) Using Hydrido Complex as Electron (Hydrido) Source Iridium mononuclear aqua complex (13) sulfate (5.8 mg, 0.01 mmol) and sodium borohydride $NaBH_4$ (7.2 mg, 0.19 mmol) were dissolved in 0.5 ml of deoxygenated heavy water ($D_2O$) at room temperature (25° C. (298 K)), thus providing an aqueous solution (pD=14.0) containing the iridium mononuclear aqua complex (13) (0.02 M) and the sodium borohydride (0.38 M). The pH of the aqueous solution was adjusted using sodium deuteroxide (NaOD, 40 wt %). This aqueous solution was stirred for 5 minutes at room temperature (25° C. (298 K)) in an argon atmosphere to cause a reaction. The reaction was followed by $^1$H-NMR. The results thereof are shown in FIG. 25. In the reaction scheme in the upper row of FIG. 25, an iridium mononuclear hydroxy complex (15) is shown as a starting material. This is because, as described in Examples 1 and 5, it is considered that most of the iridium mononuclear aqua complexes (13) turn to the iridium mononuclear hydroxy complexes (15) under basic conditions. In the $^1$H-NMR data shown in FIG. 25, the lower row is a chart regarding the iridium mononuclear hydroxy complex (15) before the reaction, and the upper row is a chart regarding the same after the reaction (for 5 minutes). As can be seen from FIG. 25, after the reaction, the peaks indicating the generation of an iridium mononuclear hydrido complex (15B), such as the peak of a hydrido ligand, were observed. The graph at the lower right of FIG. 25 is a UV-Vis. spectrum regarding a 0.14 mM aqueous solution (pH=13.7) of iridium mononuclear hydrido complex (15B) sodium salt. In this graph, the horizontal axis indicates the wavelength (nm), and the vertical axis indicates the absorbance.

As described above, in the present example, the iridium mononuclear hydrido complex (15B) sodium salt could be produced (synthesized) using, as an electron (hydrido) source, the hydrido complex ($NaBH_4$) instead of hydrogen gas.

Example 17

Figure 26:
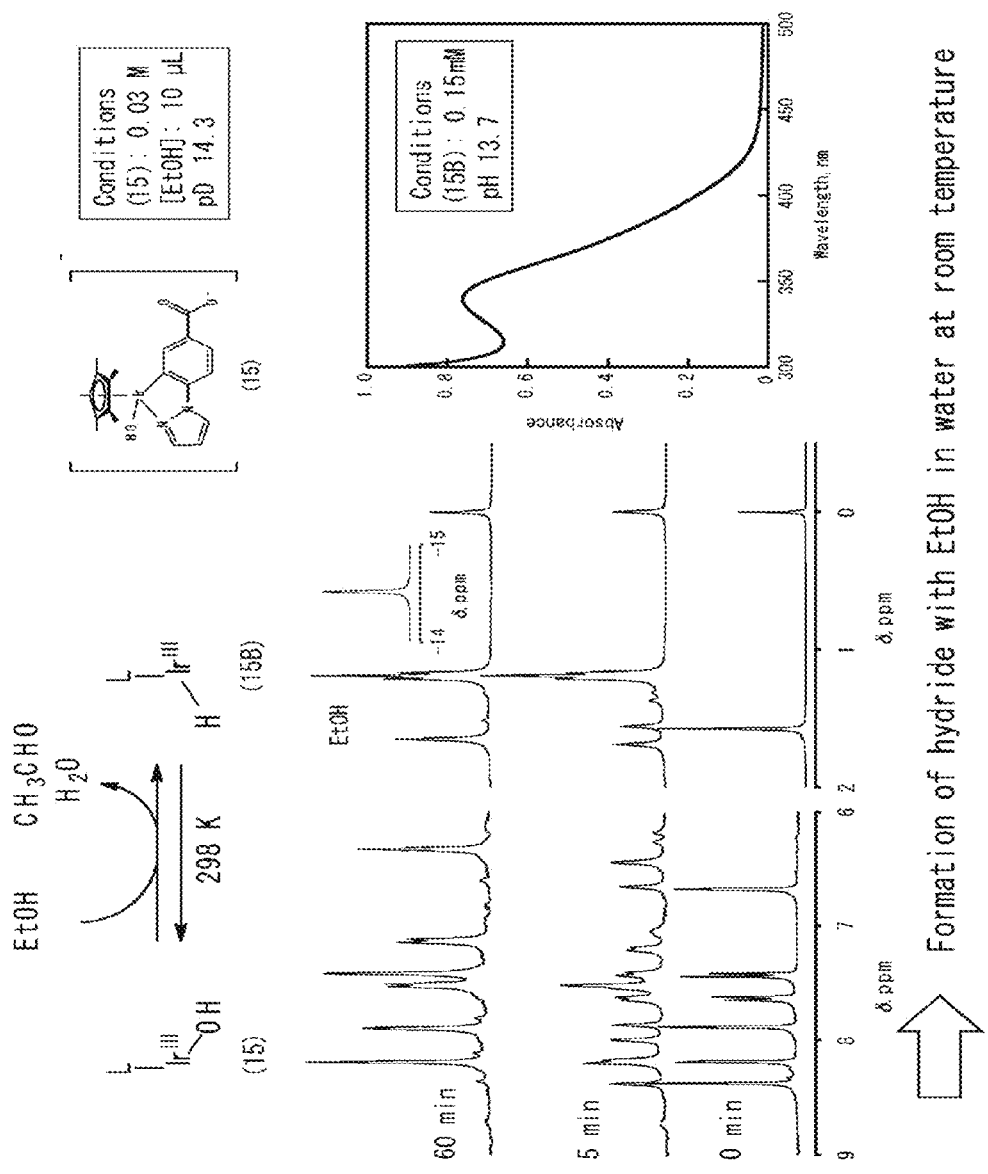
FIG. 26 shows $^1$H-NMR charts following the reaction in Example 17 (oxidation of ethanol), together with a UV-Vis. spectrum of the iridium mononuclear hydrido complex.

Production of Iridium Mononuclear Hydrido Complex (15B) Using Ethanol as Electron (Hydrido) Source and Oxidation of Ethanol Iridium mononuclear aqua complex (13) sulfate (8.7 mg, 0.015 mmol) and ethanol (10 µl) were dissolved in 0.5 ml of deoxygenated heavy water ($D_2O$) at room temperature (25° C. (298 K)), thus providing an aqueous solution (pD=14.3) containing the iridium mononuclear aqua complex (13) (0.03 M) and ethanol. The pH of the aqueous solution was adjusted by adding sodium deuteroxide (NaOD, 40 wt %). This aqueous solution was stirred for 60 minutes at room temperature (25° C. (298 K)) in an argon atmosphere to cause a reaction. The reaction was followed by $^1$H-NMR. The results thereof are shown in FIG. 26. In the reaction scheme in the upper row of FIG. 26, an iridium mononuclear hydroxy complex (15) is shown as a starting material. This is because, as described in Examples 1 and 5, it is considered that most of the iridium mononuclear aqua complexes (13) turn to the iridium mononuclear hydroxy complexes (15) under basic conditions. In the $^1$H-NMR data shown in FIG. 26, the lower row is a chart regarding the iridium mononuclear hydroxy complex (15) before the reaction, the middle row is a chart regarding the same 5 minutes after the start of the reaction, and the upper row is a chart regarding the same 60 minutes after the start of the reaction. As can be seen from FIG. 26, after the reaction, the peaks indicating the generation of an iridium mononuclear hydrido complex (15B), such as the peak of a hydrido ligand, were observed. The graph at the lower right of FIG. 26 is a UV-Vis. spectrum regarding a 0.15 mM aqueous solution (pH=13.7) of iridium mononuclear hydrido complex (15B) sodium salt. In this graph, the horizontal axis indicates the wavelength (nm), and the vertical axis indicates the absorbance.

As described above, in the present example, the iridium mononuclear hydrido complex (15B) could be produced (synthesized) using, as an electron (hydrido) source, alcohol (ethanol) instead of hydrogen gas or a hydrido complex, and also, acetaldehyde could be produced by oxidizing the ethanol.

Examples 18 to 19

Figure 27:
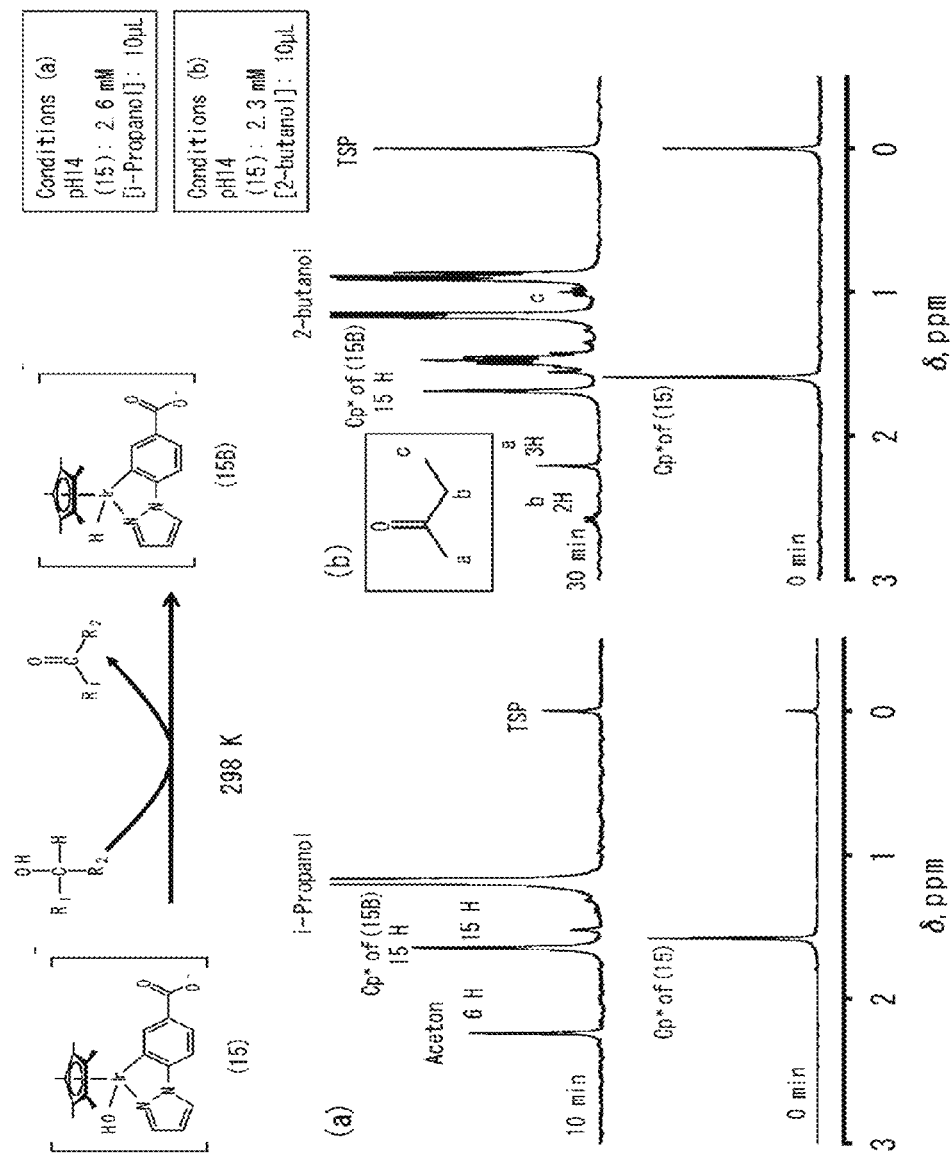
FIG. 27 shows $^1$H-NMR charts following reactions in Examples 18 to 19 (oxidation of 2-propanol or 2-butanol).

Production of Iridium Mononuclear Hydrido Complex (15B) Using 2-Propanol or 2-Butanol as Electron (Hydrido) Source and Oxidation of 2-Propanol or 2-Butanol An iridium mononuclear hydrido complex (15B) was produced using an iridium mononuclear aqua complex (13) and 2-propanol (Example 18). Specifically, first, iridium mononuclear aqua complex (13) sulfate (7.5 mg, 0.013 mmol) and 2-propanol (isopropyl alcohol) (10 µl) were dissolved in 0.5 ml of deoxygenated water at room temperature (25° C. (298 K)), thus preparing an aqueous solution (pH=14) containing the iridium mononuclear aqua complex (13) (0.026 M) and 2-propanol. The pH the aqueous solution was adjusted by adding a 5.0 M sodium hydroxide aqueous solution. This aqueous solution was stirred for 10 minutes at room temperature (25° C. (298 K)) in an argon atmosphere to cause a reaction. The reaction was followed by $^1$H-NMR. The results thereof are shown in FIG. 27. In the reaction scheme in the upper row of FIG. 27, an iridium mononuclear hydroxy complex (15) is shown as a starting material. This is because, as described in Examples 1 and 5, it is considered that most of the iridium mononuclear aqua complexes (13) turn to the iridium mononuclear hydroxy complexes (15) under basic conditions. In the $^1$H-NMR data (a) at the lower left of FIG. 27, the lower row is a chart regarding the iridium mononuclear hydroxy complex (15) before the reaction, and the upper row is a chart regarding the same 10 minutes after the start of the reaction. In FIG. 27, "Cp* of (15)" indicates the peak of methyl hydrogen in a $\eta^5$-pentamethylcyclopentadienyl group of the iridium mononuclear hydroxy complex (15). "Cp* of (15B)" indicates the peak of methyl hydrogen in a $\eta^5$-pentamethylcyclopentadienyl group of the iridium mononuclear hydrido complex (15B). "i-propanol" indicates the peak of methyl hydrogen in 2-propanol. "Acetone" indicates the peak of methyl hydrogen in acetone generated by oxidation of 2-propanol. "TSP" indicates the peak of trimethylsilyl propionate added as a reference material. The numeral such as "15H" or "6H" assigned to each peak indicates the integral ratio (the ratio of the number of protons). As can be seen from FIG. 27, after the reaction, peaks were observed that indicate: the iridium mononuclear hydroxy complex (15) was reduced to be the iridium mononuclear hydrido complex (15B); and 2-propanol was oxidized to generate acetone.

An iridium mononuclear hydrido complex (15B) was produced in the same manner as in Example 18, except that: the concentration of the iridium mononuclear aqua complex (13) was set to 2.3 mM; 10 µl of 2-butanol was used instead of 10 µl of 2-propanol; and the reaction time was set to 30 minutes (Example 19). The results thereof are shown in charts of the $^1$H-NMR date (b) at the lower right of FIG. 27. In these charts, "Cp* of (15)", "Cp* of (15B)", and "TSP" mean the same as those in the charts of the $^1$H-NMR data (a) on the left (Example 18). "2-butanol" indicates the peak of methyl hydrogen in the 2-butanol. "a", "b", and "c" each indicate the peak of methyl or methylene hydrogen, which is indicated with the same numeral in the structural formula of 2-butanone molecule shown in FIG. 27. The numeral such as "15H", "3H", or "2H" assigned to each peak indicates the integral ratio (the ratio of the number of protons). As can be seen from FIG. 27, after the reaction, peaks were observed that indicate: the iridium mononuclear hydroxy complex (15) was reduced to be the iridium mononuclear hydrido complex (15B); and 2-butanol was oxidized to generate 2-butanone.

As described above, in Examples 18 and 19, the iridium mononuclear hydrido complex (15B) could be produced (synthesized) using, as an electron (hydrido) source, an alcohol other than ethanol (2-propanol or 2-butanol) instead of ethanol, and also, aldehyde could be produced by oxidizing the alcohol.

Example 20

Production of Iridium Mononuclear Hydrido Complex (15B) Using Ethanol as Electron (Hydrido) Source and Oxidation of Ethanol (2)

Figure 28:
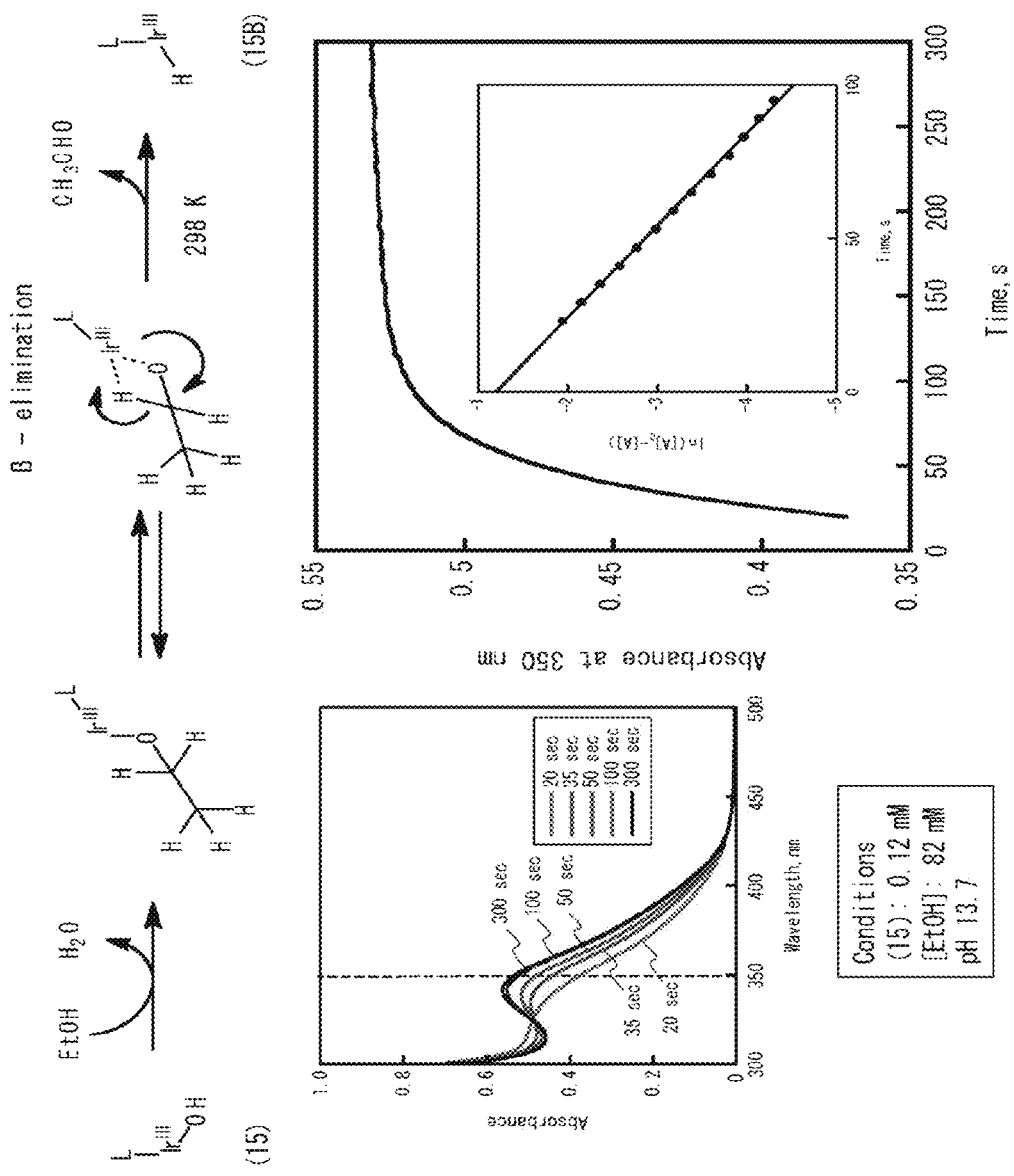
FIG. 28 shows a spectrum following the reaction in Example 20 (oxidation of ethanol) by UV-Vis.

Iridium mononuclear aqua complex (13) sulfate (0.15 mg, 0.25 µmol) and ethanol (100 µl) were dissolved in 2.0 ml of deoxygenated water at room temperature (25° C. (298 K)), thus preparing an aqueous solution (pH=13.7) containing the iridium mononuclear aqua complex (13) (0.12 M) and the ethanol (82 mM). The pH of the aqueous solution was adjusted by adding a 0.5M sodium hydroxide aqueous solution. This aqueous solution was stirred for 300 seconds at room temperature (25° C. (298 K)) in an argon atmosphere to cause a reaction. The reaction was followed by UV-Vis. spectroscopy. The results thereof are shown in FIG. 28. The lower left graph in FIG. 28 shows a UV-Vis. spectrum at the time of following the reaction. The horizontal axis indicates the wavelength (nm), and the vertical axis indicates the absorbance. As can be seen from this graph, the absorbance of the absorption band in the vicinity of 350 nm, which indicates the generation of the iridium mononuclear hydrido complex (15B), increased with time. The lower right graph in FIG. 28 shows the change in absorbance at 350 nm shown in the lower left graph with time. The horizontal axis indicates the reaction time (second), and the vertical axis indicates the absorbance at 350 nm. The inset in the lower right graph is a graph showing the correlation between the reaction time and $\ln([A]_0-[A])$, regarding the absorbance at 350 nm. The horizontal axis indicates the reaction time (second), and the vertical axis indicates $\ln([A]_0-[A])$. $[A]_0$ indicates the absorbance at 350 nm before the start of the reaction (reaction time: 0 seconds), and [A] indicates the absorbance at 350 nm at any given reaction time. ln indicates a natural logarithm. As can be seen from FIG. 28, the reaction for generating the iridium mononuclear hydrido complex (15B) (alternatively, it can be referred to as: an alcohol oxidation reaction, a hydrogen generation reaction, or an aldehyde generation reaction) in the present example was a first-order reaction, and the reaction was almost completed in about 100 seconds after the start of the reaction. The scheme in the upper row of FIG. 28 shows a presumable mechanism of the reaction for generating the iridium mononuclear hydrido complex (15B) in the present example. It is to be noted, however, that the present invention is not limited thereto.

Example 21

Figure 29:
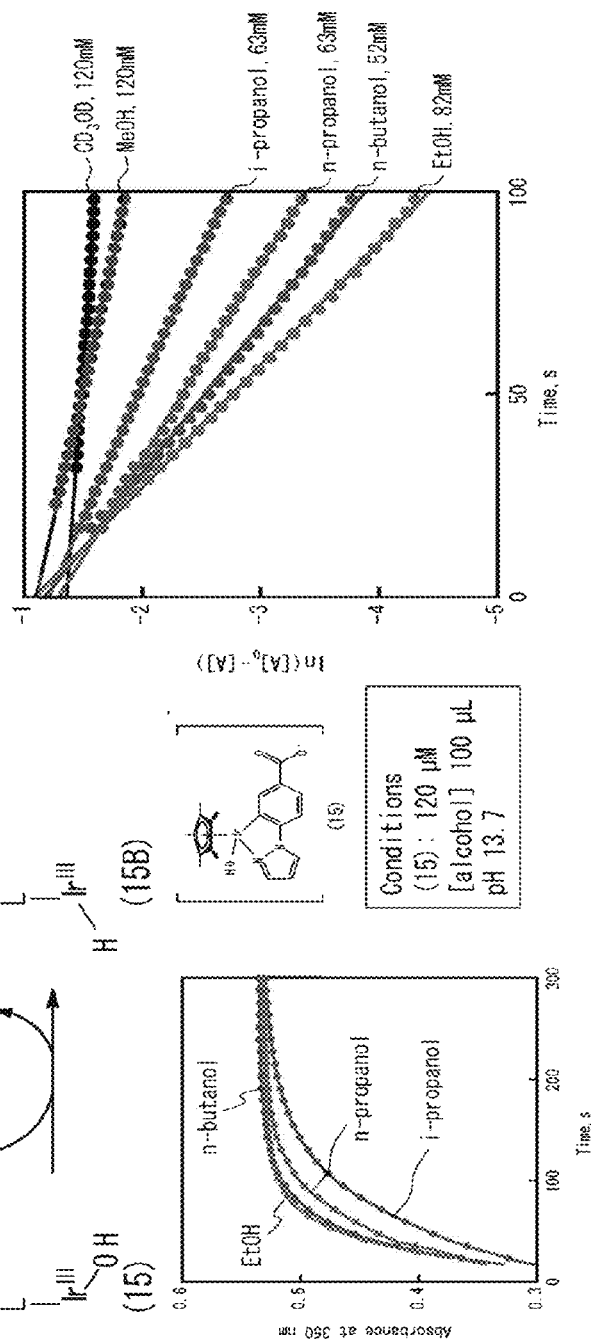
FIG. 29 shows a spectrum following the reaction in Example 21 (oxidation of each of various alcohols) by UV-Vis.

Production of Iridium Mononuclear Hydrido Complex (15B) Using Each of Various Alcohols as Electron (Hydrido) Source and Oxidation of the Alcohols Iridium mononuclear aqua complex (13) sulfate (0.15 mg, 0.25 µmol) and alcohol (100 µl) were dissolved in 2.0 ml of deoxygenated water at room temperature (25° C. (298 K)), thus preparing an aqueous solution (pH=13.7) containing the iridium mononuclear aqua complex (13) (120 µM) and the alcohol. The pH of the aqueous solution was adjusted by adding a 5.0 M sodium hydroxide aqueous solution. This aqueous solution was stirred for 300 seconds at room temperature (25° C. (298 K)) in an argon atmosphere to cause a reaction. As the alcohol, methanol, ethanol, 1-propanol (n-propanol), 2-propanol (1-propanol), or 1-butanol (n-butanol) was used. The reaction was followed by UV-Vis. spectroscopy. The results thereof are shown in FIG. 29. The left graph in FIG. 29 shows a UV-Vis. spectrum at the time of following the reaction. The horizontal axis indicates the wavelength (nm), and the vertical axis indicates the absorbance. As can be seen from this graph, the absorbance of the absorption band in the vicinity of 350 nm, which indicates the generation of the iridium mononuclear hydrido complex (15B), increased with time. The right graph in FIG. 29 shows the correlation between the reaction time and $\ln([A]_0-[A])$, regarding the absorbance at 350 nm. The horizontal axis indicates the reaction time (second), and the vertical axis indicates $\ln([A]_0-[A])$. $[A]_0$ indicates the absorbance at 350 nm before the start of the reaction (reaction time: 0 seconds), and [A] indicates the absorbance at 350 nm at any given reaction time. ln indicates a natural logarithm. As can be seen from FIG. 29, the reaction for generating the iridium mononuclear hydrido complex (15B) (alternatively, it can be referred to as: an alcohol oxidation reaction, a hydrogen generation reaction, or an aldehyde generation reaction) in the present example was a first-order reaction. The reaction rate constant k regarding each alcohol is as shown in the lower row of FIG. 29 together with the chemical structure of the alcohol.

As described above, according to Example 21, the iridium mononuclear hydrido complex (15B) could be produced (synthesized) using any of the various alcohols (aliphatic alcohols) as an electron (hydrido) source, and also, aldehyde could be produced by oxidizing the alcohol.

Example 22

Production of Hydrogen Using Ethanol as Electron (Hydrido) Source

Figure 30:
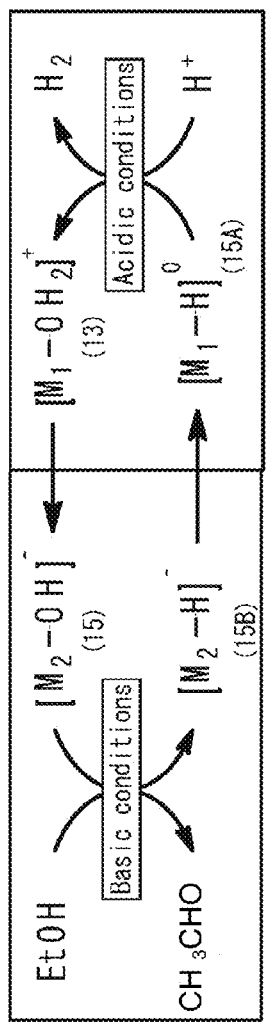
FIG. 30 shows a spectrum following the reaction in Example 22 (production of hydrogen using ethanol as an electron (hydrido) source) by UV-Vis.
Figure 30:
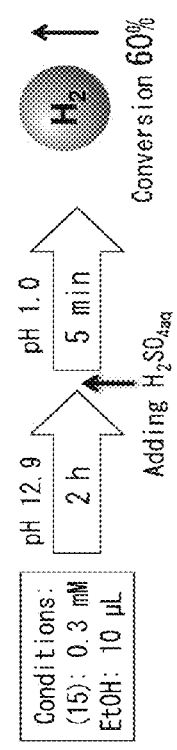
Figure 30:
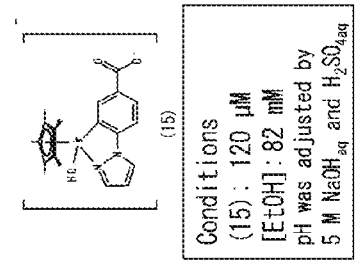
Figure 30:
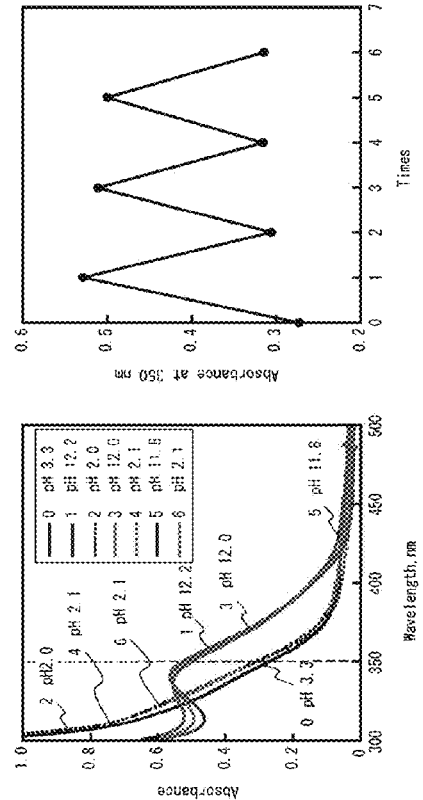

Iridium mononuclear aqua complex (13) sulfate (0.348 mg, 0.6 µmol) and ethanol (10 µl) were dissolved in 2.0 ml of deoxygenated water at room temperature (25° C. (298 K)), thus preparing an aqueous solution (pH=12.9) containing the iridium mononuclear aqua complex (13) (0.3 mM) and ethanol. The pH of the aqueous solution was adjusted by adding a 5.0M sodium hydroxide aqueous solution. This aqueous solution was stirred for 2 hours at room temperature (25° C. (298 K)) in an argon atmosphere to cause a reaction. Thereafter, the pH was adjusted to 1.0 by adding dilute sulfuric acid, and the resultant mixture was stirred for 5 minutes. As a result, hydrogen gas ($H_2$) was obtained with the yield of 60% relative to the ethanol as a raw material. The scheme in the upper row of FIG. 30 shows a presumable reaction mechanism of this reaction. Such a reaction mechanism is presumed based on the facts that, as described above, the iridium mononuclear aqua complex (13) turns to the iridium mononuclear hydroxy complex (15) under basic conditions and that the iridium mononuclear hydroxy complex (15) further turns to the iridium mononuclear hydrido complex (15B) by adding ethanol. It is to be noted, however, that this reaction mechanism merely is an example of a presumable mechanism, and does not limit the present invention by any means.

Furthermore, it was confirmed that this reaction proceeds catalytically. Specifically, first, iridium mononuclear aqua complex (13) sulfate (0.15 mg, 0.25 µmol) and ethanol (100 µl, 82 mM) were dissolved in 2.0 ml of deoxygenated water at room temperature (25° C. (298 K)). The pH of this aqueous solution was adjusted by adding a 5 M sodium hydroxide ($NaOH_{aq}$) aqueous solution and dilute sulfuric acid ($H_2SO4_{aq}$) as appropriate. Specifically, first, the dilute sulfuric acid was added to the aqueous solution to adjust the pH of the aqueous solution to 3.3, thereby causing a reaction (the generation of hydrogen gas) to start. Then, 5 minutes after the start of the reaction, the sodium hydroxide aqueous solution was added to the resultant mixture to adjust the pH of the mixture to 12.2. The resultant mixture was stirred for 10 minutes to cause ethanol and the iridium mononuclear hydroxy complex (15) to react with each other, thereby generating the iridium mononuclear hydrido complex (15B). The dilute sulfuric acid was added thereto to adjust the pH thereof to 2.0, thereby causing the hydrogen gas generation to start again. After allowing the reaction to proceed for 5 minutes, the sodium hydroxide aqueous solution was again added thereto. The above-described pH adjustment for making the aqueous solution acidic and basic alternately was repeated to a total of six times after the start of the reaction. The graph in the middle of the lower row of FIG. 30 shows the correlation between the pH and the UV-Vis. spectrum. In FIG. 30, the horizontal axis indicates the wavelength (nm), and the vertical axis indicates the absorbance. The number placed immediately in front of "pH" indicates the total number of times the above-described pH adjustment by adding the sodium hydroxide and the dilute sulfuric acid was performed. The number placed immediately behind "pH" indicates the pH at that time. As can be seen from this graph, when the pH was on the basic side, the absorbance of the absorption band in the vicinity of 350 nm increased, which suggests the generation of the iridium mononuclear hydrido complex (15B). The graph on the right side of this graph shows the relationship between the total number of times the pH adjustment was performed and the absorbance. In this graph, the horizontal axis indicates the total number of times the pH adjustment was performed, and the vertical axis indicates the absorbance at 350 nm. As can be seen from these graphs, it was confirmed that the reaction for generating the iridium mononuclear hydrido complex (15B) and hydrogen gas proceeds catalytically a plurality of times while repeating the regeneration of the catalyst (the iridium mononuclear complex).

As described above, in Example 22, using ethanol an electron (hydrido) source, i.e., a hydrogen source, a reaction for generating hydrogen gas ($H_2$) by decomposing the ethanol could be carried out catalytically with the iridium mononuclear complex of the present invention as a dehydrogenation catalyst. Although Example 22 is directed to the case where, ethanol was used as an electron (hydrido) source, i.e., a hydrogen source, in this hydrogen gas generation reaction as in Examples 17 and 20, a hydrogen source other than ethanol also may be used. For example, the hydrogen source may be the hydrido complex (e.g., $NaBH_4$) used in Example 16 or may be any of the various alcohols used in Examples 18 to 19 and 21. Also, by using any of the above-described hydrogen sources instead of hydrogen gas in reactions same as those in Examples 3 to 9 (formic acid production and carbon dioxide fixation), carbon dioxide fixation reactions (formic acid production) can be carried out catalytically.

Example 23

Production of NAD by Dehydrogenation Reaction of NADH

Figure 31:
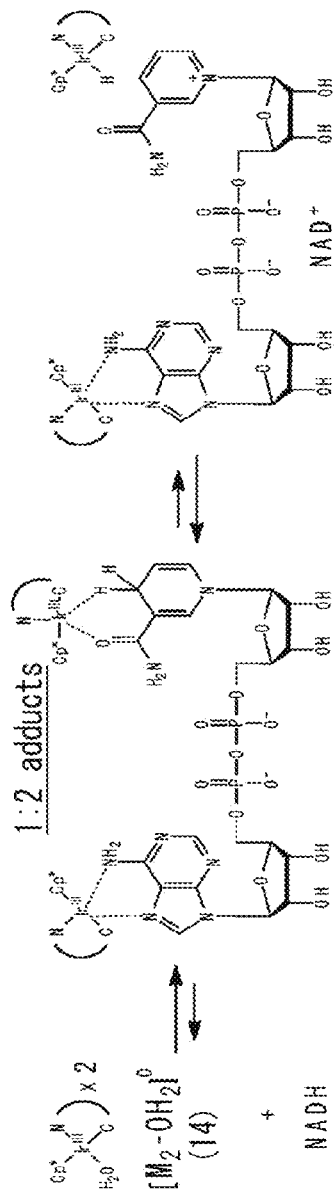
FIG. 31 shows a spectrum following the reaction in Example 23 (oxidation of NADH) by UV-Vis.
Figure 31:
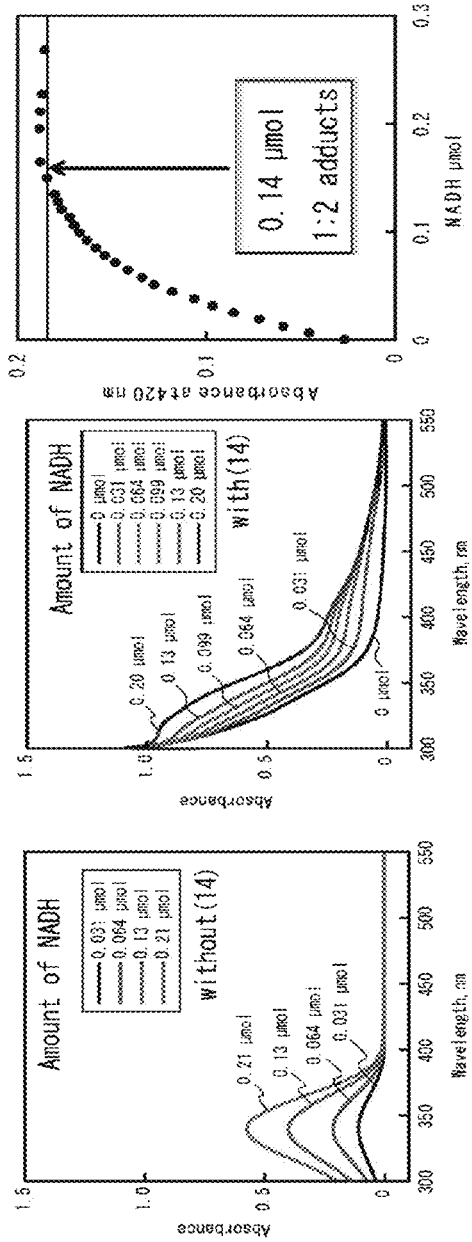

Iridium mononuclear aqua complex (13) sulfate (0.15 mg, 0.26 µmol) and NADH (reduced nicotinamide-adenine dinucleotide) were dissolved in 2 ml of deoxygenated 0.05 M phosphate-buffered aqueous solution at room temperature (25° C. (298 K)), thus preparing an aqueous solution (pH=7.5), containing the iridium mononuclear aqua complex (13) (0.13 mM) and the NADH. As shown in Example 1 and FIG. 19, it is considered that most of the iridium mononuclear aqua complexes (13) turn to the iridium mononuclear hydroxy complexes (14) at near-neutral pH. Furthermore, as a control, an NADH aqueous solution was prepared in the same manner as in the above, except that the iridium mononuclear aqua complex (13) was not added. FIG. 31 shows UV-Vis. spectra of these aqueous solutions. The left graph in the lower row of FIG. 31 shows a UV-Vis. spectrum obtained when the amount of the added NADH (shown in the graph) in the NADH aqueous solution free of the iridium mononuclear aqua complex (13) (the iridium mononuclear hydroxy complex (14)) was varied. The middle graph in the lower row of FIG. 31 shows a UV-Vis. spectrum obtained when the amount of the added NADH (shown in the graph) in the NADH aqueous solution containing the iridium mononuclear aqua complex (13) (the iridium mononuclear hydroxy complex (14)) was varied. In each of these graphs, the horizontal axis indicates the wavelength (nm), and the vertical axis indicates the absorbance. As can be seen from these graphs, the change in UV-Vis. spectrum was observed in the presence of the iridium mononuclear aqua complex (13) (the iridium mononuclear hydroxy complex (14)). The right graph in the lower row of FIG. 31 shows the correlation between the amount of the added NADH and the absorbance at 420 nm in the left and middle graphs in the lower row. In the right graph in the lower row, the horizontal axis indicates the amount of the added NADH (μm), and the vertical axis indicates the absorbance at 420 nm. As can be seen from this graph, the absorbance has reached the saturation value when the amount of the added NADH was 0.14 μm (the amount of substance thereof was about half the amount of substance of the iridium mononuclear aqua complex (13)). From this result, it is presumed that, in this reaction, as shown in the scheme in the upper row of FIG. 31, NAD (oxidized nicotinamide-adenine dinucleotide) as a dehydrogenation reaction product and the iridium mononuclear complex formed a 1:2 adduct. It is to be noted, however, that this presumption is merely illustrative and does not limit the present invention by any means.

Figure 32:
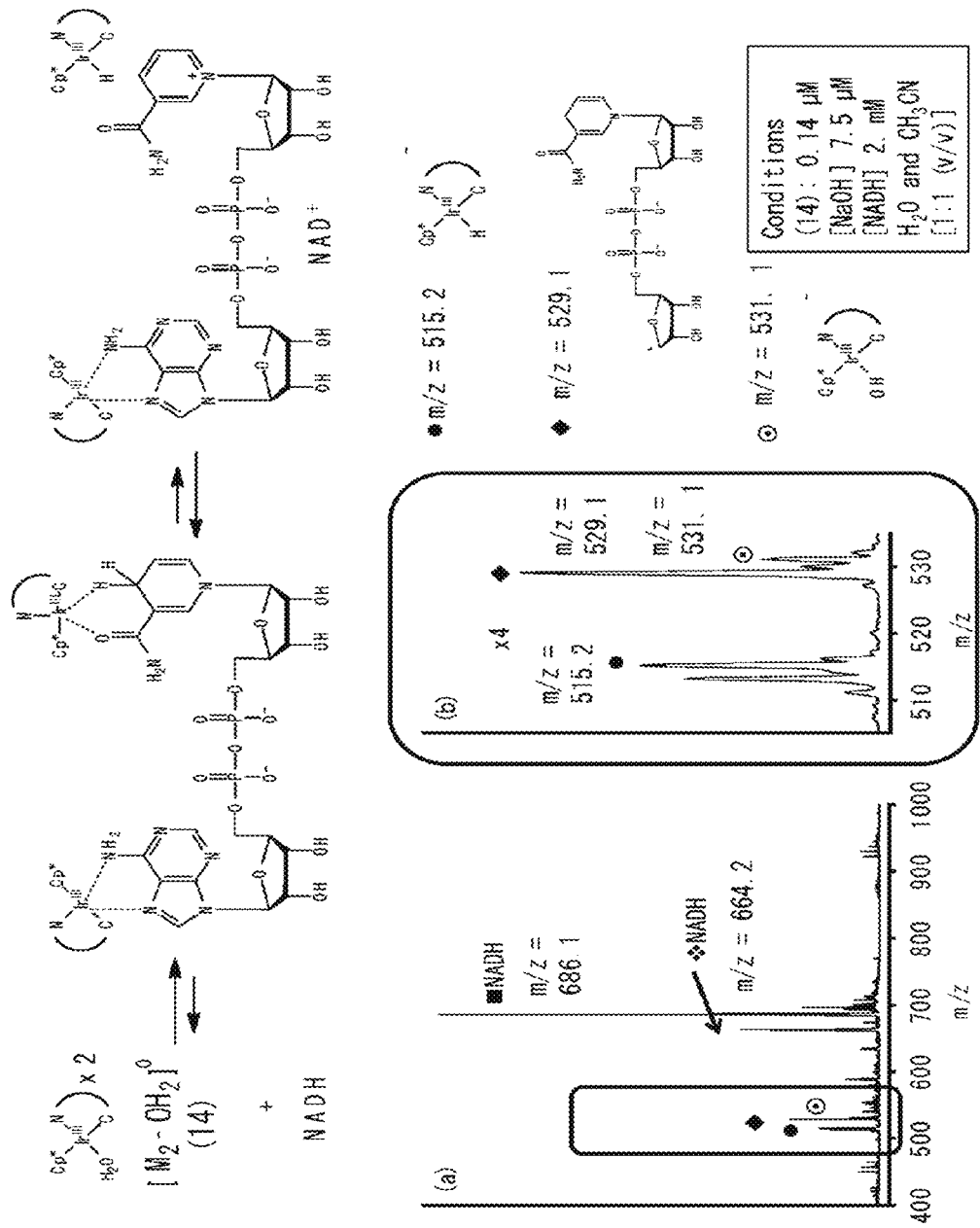
FIG. 32 shows a part of an ESI-MASS spectrum of the reaction product obtained in Example 23 (oxidation of NADH).

The products obtained through the above reaction were identified by mass spectrum analysis (mass spectrometry) and $^1$H-NMR. Specifically, first, NaOH (0.6 μg, 0.015 μmol) was dissolved in 1.0 ml of water, thus preparing a 15 μM NaOH aqueous solution. The same amount of acetonitrile was added thereto, thus preparing a 7.5 μM NaOH solution (water:acetonitrile=1:1 (volume ratio)). Iridium mononuclear aqua complex (13) sulfate (0.16 μg, 0.00028 μmol) and NADH (reduced nicotinamide-adenine dinucleotide) were dissolved therein at room temperature (25° C. (298 K)), thus preparing an aqueous solution containing the iridium mononuclear aqua complex (13) (0.14 μM) and the NADH (2 mM). FIG. 32 shows a mass spectrum (ESI-MASS) of this aqueous solution. As can be seen from this mass spectrum, the peak suggesting the presence of the iridium mononuclear hydrido complex (15B) (m/z=515.2), the peak suggesting the presence of the iridium mononuclear hydroxy complex (14) (m/z=531.1), and the peaks suggesting the presence of the NADH (m/z=529.1, 664.2, and 686.1) were observed.

Figure 33:
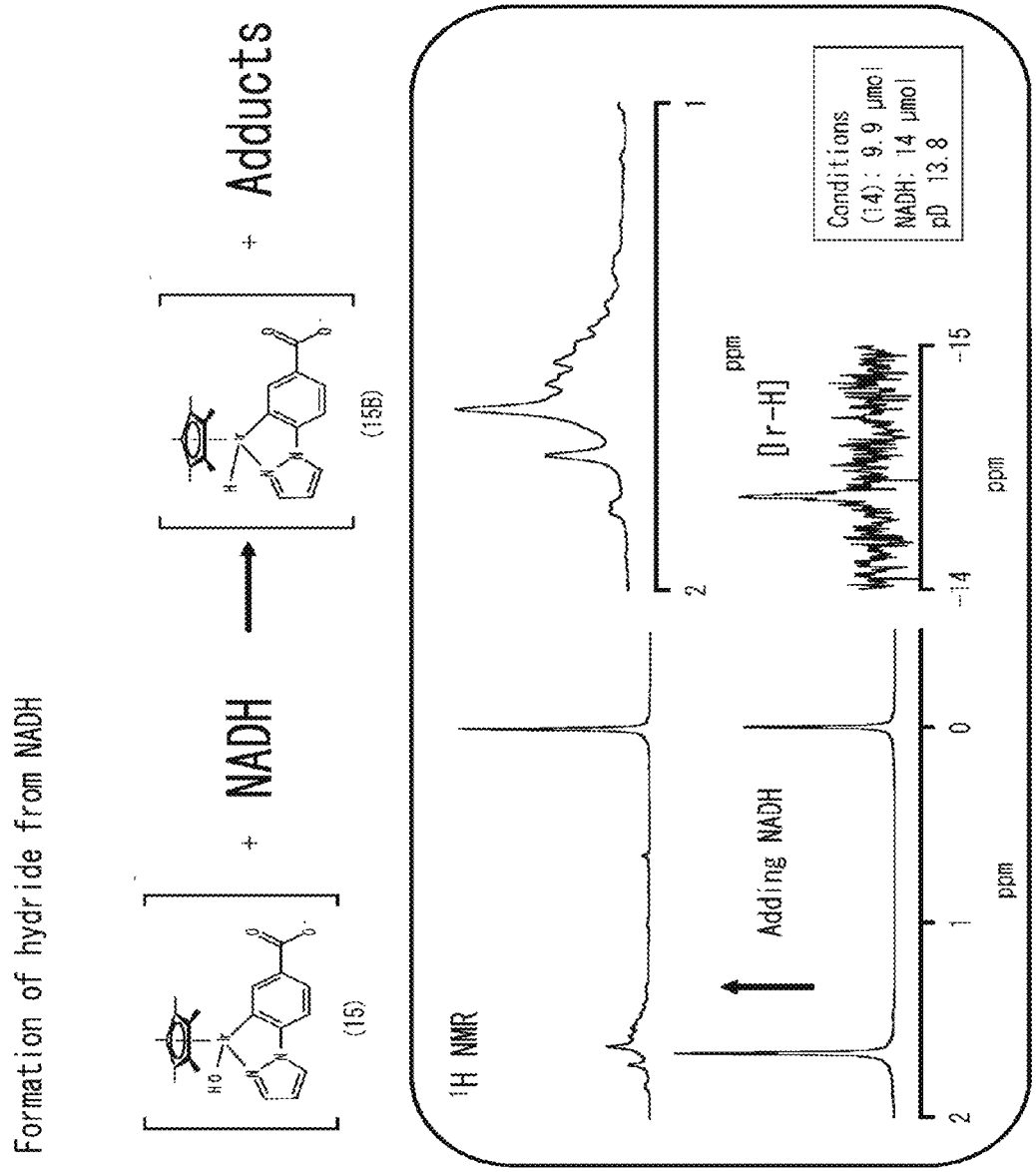
FIG. 33 shows a part of $^1$H-NMR charts of the reaction product obtained in Example 23 (oxidation of NADH).

Furthermore, iridium mononuclear aqua complex (13) sulfate (5.7 mg, 9.9 μmol) was dissolved in 0.5 ml of deoxygenated heavy water ($D_2O$) at room temperature (25° C. (298 K)), and 14 μmol of NADH was further dissolved therein. The pH of this solution was adjusted by adding sodium deuteroxide (NaOD, 40 wt %) (pD=13.8). As a control, a heavy water solution was prepared in the same manner as in the above except that NADH was not added. FIG. 33 shows $^1$H-NMR charts of these solutions. As can be seen from these charts, in the case where NADH was not added, the peak suggesting methyl hydrogen in a $\eta^5$-pentamethylcyclopentadienyl group of the iridium mononuclear hydroxy complex (15) was observed in the vicinity of 1.7 ppm. In contrast, in the case where NADH was added, a broad (wide) peak suggesting the presence of the adduct of NAD (or NADH) and the iridium mononuclear complex was observed in the vicinity of 1.5 to 2 ppm. Also, when NADH was added, the peak indicating the hydrido ligand of the iridium mononuclear aqua complex was observed in the vicinity of −14.3 ppm.

As described above, in Example 23, NAD could be produced by dehydrogenating (oxidizing) NADH by the iridium mononuclear complex of the present invention.

INDUSTRIAL APPLICABILITY

As specially described above, the mononuclear metal complex according to the present invention, a tautomer or stereoisomer thereof, or a salt thereof has high catalytic activity and thus can be used as a hydrogenation reduction catalyst (e.g., a carbon dioxide fixation catalyst or a formic acid production catalyst) that allows efficient reduction of a substance to be reduced (e.g., formic acid). Also, the mononuclear metal complex according to the present invention, a tautomer or stereoisomer thereof, or a salt thereof has high catalytic activity and thus can be used as a hydrogen ($H_2$) production catalyst (e.g., formic acid decomposition catalyst) that allows efficient production of hydrogen ($H_2$). Also, the mononuclear metal complex according to the present invention, a tautomer or stereoisomer thereof, or a salt thereof can have both the function of a hydrogenation reduction catalyst (e.g., a carbon dioxide fixation catalyst or a formic acid production catalyst) and the function of a hydrogen ($H_2$) production catalyst (e.g., a formic acid decomposition catalyst). The mononuclear metal complex having such functions, a tautomer or stereoisomer thereof, or a salt thereof is newly discovered by the inventors of the present invention. The interconversion between these functions can be achieved by, for example, changing the pH of an aqueous solution of the mononuclear metal complex of the present invention, as demonstrated in the examples. Thus, as described above, the mononuclear metal complex according to the present invention allows hydrogen ($H_2$) to be stored in the form of formic acid in an organic solvent-free (containing no organic solvent) aqueous solution at ordinary temperature and ordinary pressure (at room temperature and atmospheric pressure), for example. On the other hand, the mononuclear metal complex of the present invention can decompose formic acid at ordinary temperature (room temperature), so that it allows on-site production of hydrogen ($H_2$) by decomposing formic acid when it is needed. That is, for example, according to the present invention, with the use of a single catalyst, it is possible to clear up the most critical problems that humankind faces today to deal with environmental and energy problems, i.e., problems regarding storage, transport, and supply of hydrogen, as well as carbon dioxide reduction. It is to be noted, however, that the use of the mononuclear metal complex of the present invention is not limited to those described above.

The mononuclear metal complex according to the present invention, a tautomer or stereoisomer thereof, or a salt thereof can exhibit, as a carbon dioxide fixation catalyst with a single function, the world highest TOF in a carbon dioxide fixation reaction in water at room temperature known at the time this application was filed, for example. Therefore, it is possible to produce formic acid at low cost in an energy-saving manner with low environmental load, for example. Furthermore, the mononuclear metal complex according to the present invention, a tautomer or stereoisomer thereof, or a salt thereof can exhibit, as a formic acid decomposition catalyst with a single function, for example, the world highest TOF in a formic acid decomposition reaction in water at room temperature known at the time this application was filed, as described in the above examples. Therefore, according to the present invention, it is possible to produce hydrogen ($H_2$) at low cost in an energy-saving manner with low environmental load, for example.

Although the mononuclear metal complex according to the present invention, a tautomer or stereoisomer thereof, or a salt thereof has the above-described excellent functions, the use of the mononuclear metal complex according to the present invention, a tautomer or stereoisomer thereof, or a salt thereof is not limited to those described above, and they are applicable to any technical field. For example, as described above, carbon dioxide may be replaced with another substance to be reduced, and formic acid may be replaced with another reducing substance or hydrogen source. The use of the mononuclear complex according to the present invention is not limited to the use as a hydrogenation reduction catalyst and a dehydrogenation catalyst, and may be applied to any use.

The invention claimed is:

1. A mononuclear metal complex represented by following formula (4); a tautomer or a stereoisomer of the mononuclear metal complex; or a salt of the mononuclear metal complex, the tautomer, or the stereoisomer thereof:

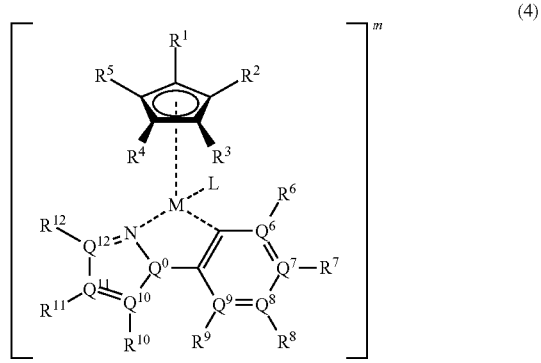

(4)

where:
$R^1$ to $R^5$ are each independently a hydrogen atom or any substituent,
$R^6$ to $R^{12}$ are each independently a hydrogen atom or any substituent, or $R^9$ and $R^{10}$ may together form —CH=CH— where the hydrogen atoms may each independently be substituted with any substituent,
at least one of $R^6$ to $R^9$ is a carboxy group, a sulfo group, a phenolic hydroxyl group, a phosphate group, an amino group, or a hydroxymethyl group the anionic group,
$Q^0$ is C or N,
$Q^6$ to $Q^{12}$ are each independently C or $N^+$,
or at least one pair of $Q^X$ and $R^X$ having same X, where X is any integer from 6 to 12, may together form N, and
M is an atom or ion of a transition metal,
L is any ligand or is not present, and
m is a positive integer, 0, or a negative integer.

2. The mononuclear metal complex according to claim 1, wherein in the mononuclear metal complex of the formula (4) M is iridium, ruthenium, rhodium, cobalt, osmium, nickel, iron, manganese, chromium, cobalt, platinum, or palladium;
   a tautomer or a stereoisomer of the mononuclear metal complex; or
   a salt of the mononuclear metal complex, the tautomer, or the stereoisomer thereof.

3. The mononuclear metal complex according to claim 1, wherein the mononuclear metal complex represented by the formula (4) is an iridium mononuclear metal complex represented by following formula (10);
   a tautomer or a stereoisomer of the mononuclear metal complex; or
   a salt of the mononuclear metal complex, the tautomer, or the stereoisomer thereof:

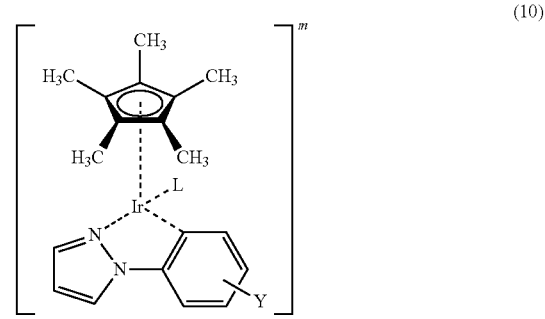

(10)

where:
Ir is an atom or ion of iridium,
Y is a carboxy group, a sulfo group, a phenolic hydroxyl group, a phosphate group, an amino group, or a hydroxymethyl group, and
L and m are same as those in the formula (4).

4. The mononuclear metal complex according to claim 3, wherein the iridium mononuclear metal complex represented by the formula (10) is an iridium mononuclear metal complex represented by following formula (11);
   a tautomer or a stereoisomer of the mononuclear metal complex; or
   a salt of the mononuclear metal complex, the tautomer, or the stereoisomer thereof:

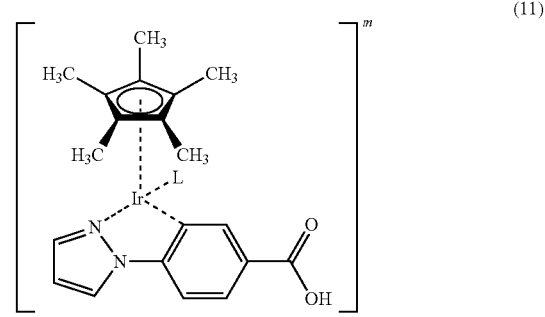

(11)

where:
L, m, and Ir are same as those in the formula (10).

5. The mononuclear metal complex according to claim 3, wherein the iridium mononuclear metal complex represented by the formula (10) is an iridium mononuclear metal complex represented by following formula (12);
   a tautomer or a stereoisomer of the mononuclear metal complex; or
   a salt of the mononuclear metal complex, the tautomer, or the stereoisomer thereof:

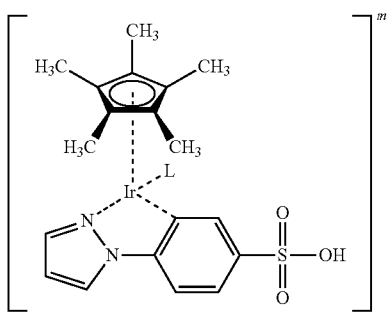
(12)

where:

L, m, and Ir are same as those in the formula (10).

6. The mononuclear metal complex according to claim 4, wherein the iridium mononuclear metal complex represented by the formula (11) is an iridium mononuclear metal complex represented by any one of following formulae (13), (14), (15), (15A), and (15B);

a tautomer or a stereoisomer of the mononuclear metal complex; or a salt of the mononuclear metal complex, the tautomer, or the stereoisomer thereof,

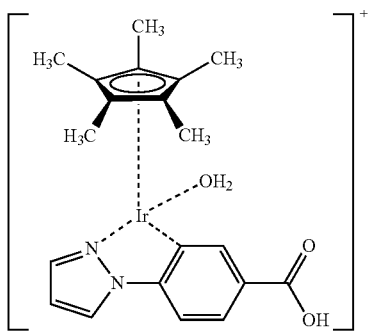
(13)

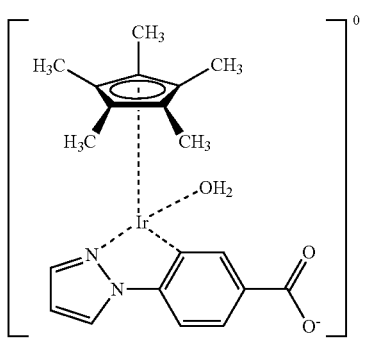
(14)

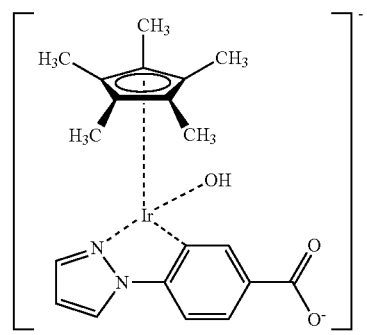
(15)

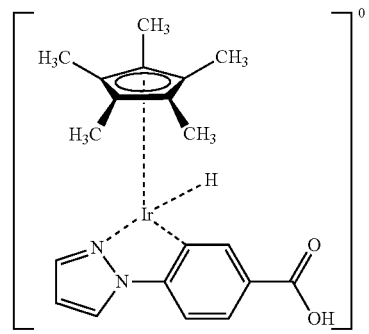
(15A)

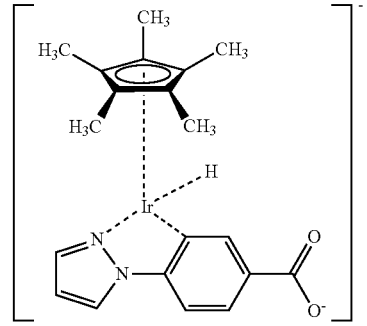
(15B)

7. The mononuclear metal complex according to claim 5, wherein the iridium mononuclear metal complex represented by the formula (12) is an iridium mononuclear metal complex represented by any one of following formulae (16), (17), (18), (18A), and (18B);

a tautomer or a stereoisomer of the mononuclear metal complex; or a salt of the mononuclear metal complex, the tautomer, or the stereoisomer thereof,

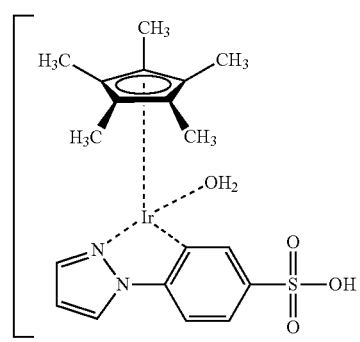
(16)

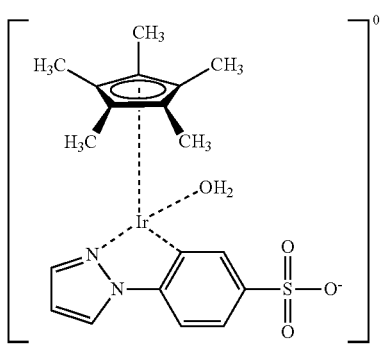

(17)

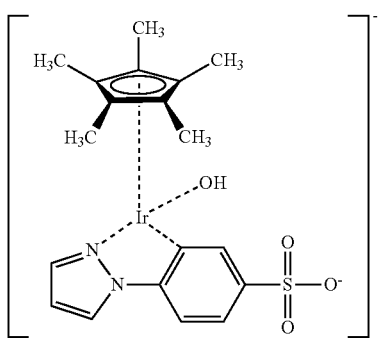

(18)

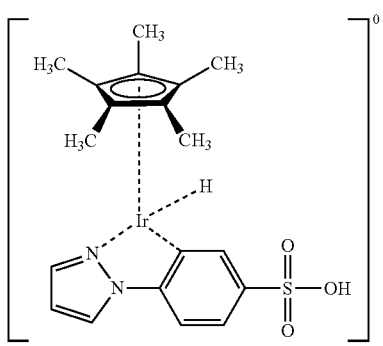

(18A)

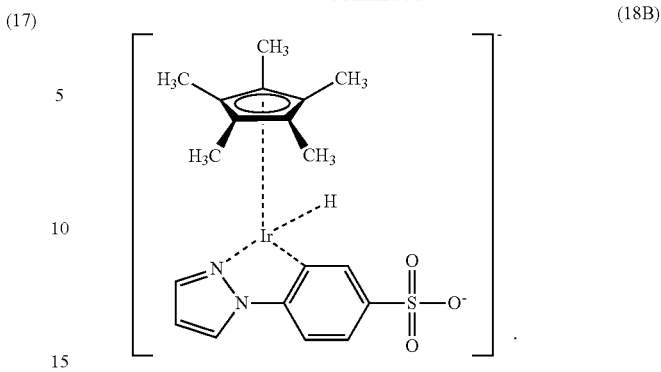

(18B)

8. A catalyst comprising:
the mononuclear metal complex according to claim 1; a tautomer or a stereoisomer of the mononuclear metal complex; or a salt of the mononuclear metal complex, the tautomer, or the stereoisomer thereof.

9. A method for producing a reduction product by a reduction reaction that adds hydrogen to a substance to be reduced, the method comprising a step of:
in a solution or a disperse system that comprises the catalyst according to claim 8, the substance to be reduced, and hydrogen ($H_2$), reducing the substance to be reduced by a reaction between the substance to be reduced and the added hydrogen ($H_2$).

10. A method for producing hydrogen ($H_2$) and an oxidation product by an oxidation reaction that removes hydrogen from a hydrogen source, the method comprising a step of:
in a solution or a disperse system that comprises the catalyst according to claim 8 and the hydrogen source, decomposing the hydrogen source by the oxidation reaction so as to generate the hydrogen ($H_2$) and the oxidation product.

11. A method for producing formic acid by a reaction of fixing carbon dioxide, the method comprising a step of:
in a solution or a disperse system that comprises the catalyst according to claim 8, carbon dioxide or an ion thereof, and hydrogen ($H_2$), fixing the carbon dioxide by a reaction between the carbon dioxide and the added hydrogen ($H_2$) so as to produce the formic acid.

12. A method for producing hydrogen ($H_2$) and carbon dioxide or an ion thereof by a reaction of removing carbon dioxide, the method comprising a step of:
in a solution or a disperse system that comprises the catalyst according to claim 8 and formic acid subjected to the reaction of removing carbon dioxide, decomposing the formic acid by the reaction of removing carbon dioxide so as to generate the hydrogen ($H_2$) and the carbon dioxide or an ion thereof.

\* \* \* \* \*